US 7,067,509 B2

(12) United States Patent
Goodfellow et al.

(10) Patent No.: US 7,067,509 B2
(45) Date of Patent: Jun. 27, 2006

(54) MELANIN-CONCENTRATING HORMONE RECEPTOR ANTAGONISTS AND COMPOSITIONS AND METHODS RELATED THERETO

(75) Inventors: Val Goodfellow, Encinitas, CA (US); Martin Rowbottom, La Jolla, CA (US); Brian P Dyck, San Diego, CA (US); Junko Tamiya, Oceanside, CA (US); Mingzhu Zhang, San Diego, CA (US); Jonathan Grey, San Diego, CA (US); Troy D Vickers, San Diego, CA (US); Mehrak Kiankarimi, San Diego, CA (US); Warren Wade, San Diego, CA (US); Sarah Clough, San Diego, CA (US); Joseph Pontillo, San Diego, CA (US); Dongpei Wu, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 202 days.

(21) Appl. No.: 10/797,487

(22) Filed: Mar. 8, 2004

(65) Prior Publication Data

US 2004/0259931 A1    Dec. 23, 2004

Related U.S. Application Data

(60) Provisional application No. 60/452,709, filed on Mar. 7, 2003.

(51) Int. Cl.
*A61K 31/397* (2006.01)
*A61K 31/401* (2006.01)
*A61K 31/4025* (2006.01)
*C07D 207/14* (2006.01)

(52) U.S. Cl. .............. 514/210.18; 514/422; 548/524; 548/953

(58) Field of Classification Search ............. 548/524, 548/953; 514/422, 210.18
See application file for complete search history.

(56) References Cited

U.S. PATENT DOCUMENTS

| | | | | |
|---|---|---|---|---|
| 4,576,749 | A | * | 3/1986 | Zahler et al. ............. 540/363 |
| 5,652,249 | A | * | 7/1997 | Kimura et al. ............ 514/326 |
| 6,734,176 | B1 | * | 5/2004 | Achard et al. ......... 514/210.01 |
| 2002/0052383 | A1 | | 5/2002 | Bakthavatchalam et al. ............. 514/255.03 |
| 2003/0216380 | A1 | * | 11/2003 | Josien et al. ........... 514/217.03 |

FOREIGN PATENT DOCUMENTS

| | | |
|---|---|---|
| JP | 2001272751 A2 * | 10/2001 |
| WO | WO 01/21169 A1 | 3/2001 |
| WO | WO 01/21577 A2 | 3/2001 |
| WO | WO 01/82925 A1 | 11/2001 |
| WO | WO 01/87834 A1 | 11/2001 |
| WO | WO 01/94368 A1 | 12/2001 |
| WO | WO 02/04433 A2 | 1/2002 |
| WO | WO 02/06245 A1 | 1/2002 |
| WO | WO 02/057233 A1 | 7/2002 |
| WO | WO 02/076929 A1 | 10/2002 |
| WO | WO 2003013527 A1 * | 2/2003 |

OTHER PUBLICATIONS

Whooley, M., and Simon, G., "Managing Depression in Medical Outpatients," New Engl. J. Med., vol. 343(26), pp. 1942-1950 (Dec. 2000), at p. 1946, line 4 (Table 4).*
Nakamura, K., and Tanaka, Y., "Antidepressant-like effects of aniracetam in aged rats and its mode of action," Psychopharmacology, vol. 158(2), pp. 205-212 (Nov. 2001), at Abstract; p. 210, col. 2, lines 58-59 and p. 211, lines 1-2.*
Derwent World Patents Index, English Abstract of JP 2001-226269, Aug. 21, 2001.
Bednarek, M., et al., "Synthesis and Biological Evaluation in Vitro of a Selective, High Potency Peptide Agonist of Human Melanin-concentrating Hormone Action at Human Melanin-Concentrating Hormone Receptor 1," *J. Biol. Chem.* 277(16):13821-6, Apr. 19, 2002.

(Continued)

*Primary Examiner*—Taofiq Solola
*Assistant Examiner*—Anthony J. Paviglianiti
(74) *Attorney, Agent, or Firm*—Seed IP Law Group PLLC

(57) ABSTRACT

Melanin-concentrating hormone (MCH) receptor antagonists are disclosed having utility for the treatment of MCH receptor-based disorders such as obesity. The compounds of this invention have the following structure:

including stereoisomers and pharmaceutically acceptable salts thereof, wherein n, $R_1$, $R_2$, $R_3$, $R_4$, $R_5$, and $R_6$ are as defined herein. Pharmaceutical compositions containing a compound of this invention, as well as methods relating to the use thereof, are also disclosed.

59 Claims, No Drawings

OTHER PUBLICATIONS

Takekawa, S., et al., "T-226296: A Novel, Orally Active and Selective Melanin-concentrating Hormone Receptor Antagonist," *Eur. J. Pharmacol.* 438(3):129-35, Mar. 8, 2002.

* cited by examiner

MELANIN-CONCENTRATING HORMONE RECEPTOR ANTAGONISTS AND COMPOSITIONS AND METHODS RELATED THERETO

CROSS-REFERENCE TO RELATED APPLICATION

This application claims the benefit of U.S. Provisional Patent Application No. 60/452,709 filed Mar. 7, 2003, which provisional application is incorporated herein by reference in its entirety.

BACKGROUND OF THE INVENTION

1. Field of the Invention

This invention generally relates to antagonists of melanin-concentrating hormone receptors, and to compositions and methods related thereto.

2. Description of the Related Art

Melanin-concentrating hormone (MCH) is a neuropeptide that exerts a powerful effect on food intake and body weight regulation (Broberger & Hokfelt, PHYSIOL. BEHAV. 2001 November–December; 74(4–5): 669–82). As a result, this neuropeptide, as well as antagonists to its various receptors, has been investigated for use in therapies relating to eating and body weight regulating disorders.

More specifically, MCH is a cyclic neuropeptide that is over expressed in obese mice. Experiments where MCH was directly injected into lateral ventricles of the brains of rats resulted in increased consumption of food, indicating that MCH has a role in the regulation of body weight (Qu, et al., NATURE 1996 Mar. 21; 380 (6571):243–7). The orexigenic (appetite-stimulating) activity is believed to result from MCH's binding to a melanin-concentrating hormone receptor (MCH-1R) determined to be a 353 amino acid human orphan G-Protein-Coupled Receptor (GPCR) SLC-1 (Chambers et al., NATURE 1999 Jul. 15; 400(6741): 261–5; Saito et al., NATURE 1999 Jul. 15; 4000(6741): 265–9). Mice deficient in MCH-1R have normal body weights, yet are lean and have reduced fat mass; thus, less susceptible to diet-induced obesity (Marsh et al., PROC. NATL. ACAD. SCI. 2002 Mar. 5; 99 (5): 3240–5). A second MCH receptor (MCH-2R) has also been identified (Sailer et al., PROC. NATL. ACAD. SCI. 2001 Jun. 19; 98(13): 7564–9; An et al. PROC. NATL. ACAD. SCI. 2001 Jun. 19; 98(13): 7576–81).

In view of its biological importance, a number of researchers have reported proteins or small molecule antagonists to MCH receptors. For example, Merck Research Laboratories has reported protein agonists consisting of the cyclic core of human MCH that activates both MCH-1R and MCH-2R, and an agonist with selectivity for MCH-1R (Bednarek et al., J BIOL CHEM 2002 Apr. 19; 277(16): 13821–6). Takeda Chemical Industries (Takeda) has disclosed the use of (−)-N-[6-(dimethylamino)-methyl]-5,6,7,8-tetrahydro-2-naphthalenyl]-4′-fluoro-[1,1′-biphenyl]-4-carboxamide and derivatives thereof as selective MCH-1R inhibitors (Kakekawa et al., EUR J PHAMOCOL 2002 Mar. 8; 438(3); 129–35; WO 01/21577). Additional Takeda patent publications directed to MCH antagonists include JP 2001226269; WO 01/21169; WO 01/82925; and WO 01/87834. Synaptic Pharmaceutical Corporation has similarly disclosed MCH receptor antagonists (WO 02/06245), as has Neurogen Corporation (WO 02/04433; U.S. 20020052383 A1).

Accoringly, there remains a need in the art for novel MCH receptor antagonists, including antagonists of MCH-1R and/or MCH-2R, and for compositions and methods related thereto. The present invention fulfils these needs and provides further related advantages.

BRIEF SUMMARY OF THE INVENTION

In brief, this invention is generally directed to compounds that function as antagonists to one or more melanin-concentrating hormone (MCH) receptor(s). This invention is also directed to compositions containing one or more of such compounds in combination with one or more pharmaceutically acceptable carriers, as well as to methods for treating conditions or disorders associated with MCH.

In one embodiment, this invention is directed to compounds that have the following structure (I):

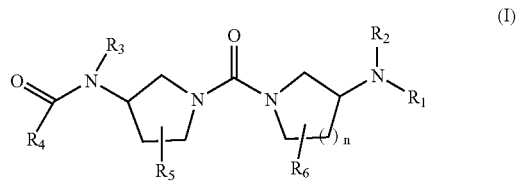

(I)

including stereoisomers, prodrugs, and pharmaceutically acceptable salts thereof, wherein n, $R_1$, $R_2$, $R_3$, $R_4$, $R_5$ and $R_6$ are as defined herein.

The compounds of this invention have utility over a broad range of therapeutic applications, and may be used to treat disorders or illnesses, including (but not limited to) eating disorders, body weight disorders, anxiety, depression and CNS disorders. A representative method of treating such a disorder or illness includes administering an effective amount of a compound of this invention, typically in the form of a pharmaceutical composition, to an animal in need thereof (also referred to herein as a "patient", including a human). Accordingly, in another embodiment, pharmaceutical compositions are disclosed containing one or more compounds of this invention in combination with a pharmaceutically acceptable carrier.

In one embodiment, compounds of this invention may serve as antagonists to either MCH-1R, MCH-2R, or both receptors, or may serve as antagonists to other MCH receptors which have yet to be identified. Such antagonists have beneficial therapeutic effects, especially in the treatment of obesity, and diseases associated with overeating and weight disorders.

These and other aspects of this invention will be apparent upon reference to the following detailed description and attached figures. To that end, certain patent and other documents are cited herein to more specifically set forth various aspects of this invention. Each of these documents is hereby incorporated by reference in its entirety.

DETAILED DESCRIPTION OF THE INVENTION

As mentioned above, the present invention is generally directed to compounds useful as melanin-concentrating hormone (MCH) receptor antagonists. The compounds of this invention have the following structure (I):

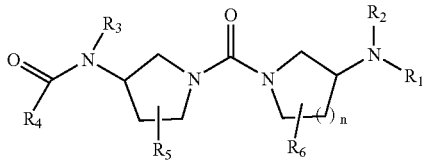

(I)

or a stereoisomer, prodrug or pharmaceutically acceptable salt thereof, wherein:
n is 0 or 1;
$R_1$ is hydrogen, alkyl, substituted alkyl, arylalkyl, substituted arylalkyl, heterocylealkyl, substituted heterocyclealkyl, heterocycle, or substituted heterocycle;
$R_2$ is hydrogen, alkyl, substituted alkyl, —C(O)$R_7$, or —S(O)$_2R_8$; or
$R_1$ and $R_2$ together with the nitrogen to which they are attached form a heterocycle, optionally substituted with one or more $R_9$;
$R_3$ is hydrogen, alkyl, or substituted alkyl;
$R_4$ is alkyl, substituted alkyl, aryl, substituted aryl, heteroaryl, substituted heteroaryl, heterocycle, or substituted heterocycle;
$R_5$ is hydrogen, alkyl, or substituted alkyl;
$R_6$ is hydrogen, alkyl, or substituted alkyl; and
$R_7$ is hydrogen, alkyl, substituted alkyl, hydroxy, alkoxy, aryl, substituted aryl, heterocycle, or substituted heterocycle;
$R_8$ is hydrogen, alkyl, substituted alkyl; and
$R_9$ is alkyl, substituted alkyl, aryl, substituted aryl, hydroxy, or alkoxy.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclohexyl, cycloheptyl, and the like; while unsaturated cyclic alkyls include cyclopentenyl, cyclohexenyl, —CH$_2$cyclohexenyl, and the like. Cyclic alkyls are also referred to herein as a "homocycle" or "homocyclic ring." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"Aryl" means an aromatic carbocyclic moiety such as phenyl or naphthyl.

"Arylalkyl" means an alkyl having at least one alkyl hydrogen atom replaced with an aryl moiety, such as benzyl (i.e., —CH$_2$phenyl), —(CH$_2$)$_2$phenyl, —(CH$_2$)$_3$phenyl, —CH(phenyl)$_2$, and the like. Arylalkyl also includes a bicyclic structure of a cyclic alkyl having two alkyl hydrogen atoms replaced with an aryl moiety, e.g., a cyclic alkyl being fused to a benzene ring, a representative of which is indanyl.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thienyl, benzothienyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, triazolyl, tetrazolyl, oxadiazolyl, benzoxadiazolyl, thiadiazolyl, indazolyl and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocyclic ring") means a 4- to 7-membered monocyclic, or 7- to 10-membered bicyclic, heterocyclic ring which is saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, homopiperidinyl, 1,3-dioxolanyl, 1,3-dioxanyl, 1,4-dioxanyl, piperazinyl, antoinyl, valerolactamyl, oxiranyl, oxetanyl, tetrahydrofuranyl, tetrahydropyranyl, tetrahydropyridinyl, tetrahydroprimidinyl, tetrahydrothienyl, tetrahydrothiopyranyl, tetrahydropyrimidinyl, tetrahydrothienyl, tetrahydrothiopyranyl, and the like.

The term "substituted" as used herein means any of the above groups (i.e., alkyl, aryl, arylalkyl, heteroaryl, heteroarylalkyl, heterocycle and heterocyclealkyl) wherein at least one hydrogen atom is replaced with a substituent. In the case of an oxo substituent ("=O") two hydrogen atoms are replaced. When substituted, "substituents" within the context of this invention include oxo, halogen, hydroxy, cyano, nitro, amino, alkylamino, dialkylamino, alkyl, alkoxy, thioalkyl, sulfonylalkyl, haloalkyl, hydroxyalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$R$_b$, —NR$_a$C(=O)OR$_b$—NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$, —S(=O)$_2$OR$_a$, —CH$_2$S(=O)$_2$R$_a$, —CH$_2$S(=O)$_2$NR$_a$R$_b$, =NS(=O)$_2$R$_a$, —S(=O)$_2$NR$_a$R$_b$ wherein R$_a$ and R$_b$ are the same or different and independently hydrogen, alkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moieties attached through a nitrogen bridge (i.e., —N-alkyl) such as methylamino, ethylamino, dimethylamino, diethylamino, and the like.

"Hydroxyalkyl" means an alkyl substituted with at least one hydroxyl group.

In an embodiment, compounds of this invention have the following structure (II) when n is 1 and structure (III) when n is 0.

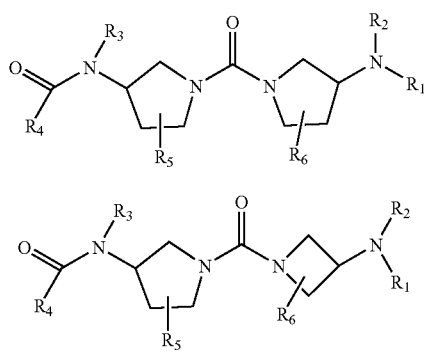

In further embodiments, $R_1$ and $R_2$ of structure (II) and (III) are the same or different and independently hydrogen, alkyl or substituted alkyl, wherein the alkyl moiety, as well as the alkyl portion of substituted alkyl moiety, includes saturated straight chain and saturated branched alkyls, as well as saturated cyclic alkyls such as cyclohexyl. Substituted alkyls include alkyls substituted with one or more substituents as defined above, including (but not limited to) —OR$_a$, —SR$_a$, —C(=O)R$_a$, —S(=O)R$_a$, and —S(=O)$_2$R$_a$ wherein R$_a$ is as defined above and including (but not limited to) alkyl, aryl and heterocycle optionally substituted with a one or more further substituent(s) as defined above. For example, representative substituted $R_1$ and $R_2$ moieties include alkyl substituted with —O(alkyl), —S(alkyl), —C(=O)(alkyl), —C(=O)(O(alkyl)), —S(=O)(alkyl), —S(=O)$_2$(alkyl), —O(aryl), —S(aryl), —C(=O)(aryl), —S(=O)(aryl), —S(=O)$_2$(aryl), —O(heterocycle), —S(heterocycle), —C(=O)(heterocycle), —S(=O)(heterocycle), and —S(=O)$_2$(heterocycle), wherein each of alkyl, aryl and heterocycle may be further substituted with one or more substituents. Alternatively, $R_1$ and $R_2$ together with the nitrogen to which they are attached form a heterocycle, optionally substituted with one or more alkyl, aryl, hydroxy or alkoxy. In the above contexts, $R_4$ can be alkyl, substituted alkyl, aryl, substituted aryl, heterocycle, or substituted heterocycle.

In a more specific embodiment of structures (II) and (III), $R_3$ is hydrogen or lower alkyl such as methyl, $R_5$ and $R_6$ are each hydrogen or lower alkyl. $R_4$ is substituted heteroaryl, substituted aryl and substituted alkyl. More specifically, $R_4$ is substituted heteroaryl such as substituted thienyl, examples of which are shown in Table 1.

TABLE 1

| Structure | Name |
|---|---|
| 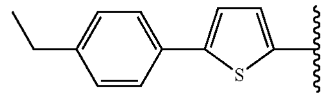 | 2-[5-(4-ethylphenyl)thienyl] |
| 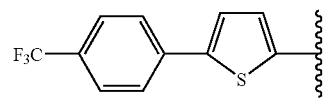 | 2-[5-(4-trifluoromethyl-phenyl)thienyl] |
| 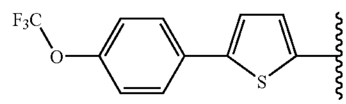 | 2-[5-(4-trifluoromethoxy-phenyl)thienyl] |
| 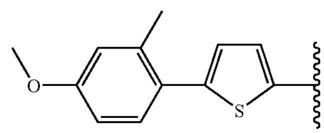 | 2-[5-(2-methyl-4-methoxyphenyl)thienyl] |
| 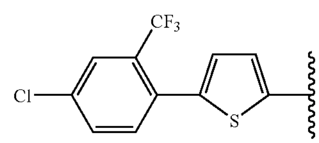 | 2-[5-(2-trifluoromethyl-4-chlorophenyl)thienyl] |
| 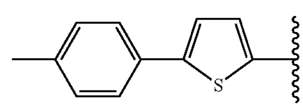 | 2-[5-(4-methylphenyl)-thienyl] |
| 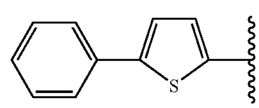 | 2-(5-phenylthienyl) |
| 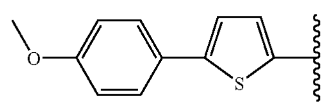 | 2-[5-(4-methoxyphenyl)-thienyl] |
| 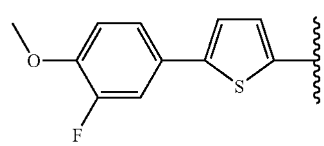 | 2-[5-(3-fluoro-4-methoxyphenyl)thienyl] |
| 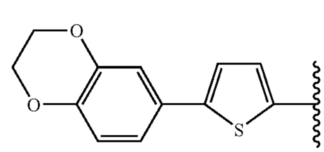 | 2-[5-(6-1,4-benzodioxanyl)thienyl] |
| 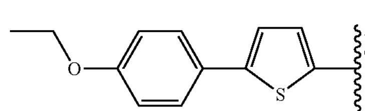 | 2-[5-(4-ethoxyphenyl)thienyl] |

TABLE 1-continued

| Structure | Name |
|---|---|
| (3-fluoro-4-methylphenyl-thienyl structure) | 2-[5-(3-fluoro-4-methylphenyl)thienyl] |
| (2,4-dimethylphenyl-thienyl structure) | 2-[5-(2,4-dimethylphenyl)thienyl] |
| (4-isopropylphenyl-thienyl structure) | 2-[5-(4-isopropylphenyl)thienyl] |

In this context, $R_1$ is hydrogen, cyclic alkyl, substituted cyclic alkyl, heterocycle, substituted heterocycle, heterocyclealkyl, substituted heterocyclealkyl, alkyl, or substituted alkyl. $R_2$ is hydrogen or lower alkyl such as methyl, ethyl or isopropyl. Alternatively, $R_1$ and $R_2$ together with the nitrogen to which they are attached form a heterocycle, optionally substituted with one or more alkyl, aryl, hydroxy or alkoxy. More specifically, particularly with respect to Structure (II), when $R_4$ is heteroaryl such as those illustrated in Table 1, $R_1$ and $R_2$ can be any of the following combinations: $R_1$ and $R_2$ are each hydrogen. $R_2$ is hydrogen or lower alkyl such as methyl or ethyl, $R_1$ is cyclic alkyl or substituted cyclic alkyl such as cyclobutyl, cyclopentyl, cyclohexyl, 4-methylcyclohexyl, 4,4-dimethylcyclohexyl, 4-trifluoromethylcyclohexyl, 2-ethylcyclohexyl, 3,4-dimethylcyclohexyl and cycloheptyl. $R_2$ is hydrogen or lower alkyl such as methyl or ethyl, $R_1$ is heterocycle or substituted heterocycle such as 4-tetrohydropyranyl and 4-(1-benzylpiperidinyl). $R_2$ is hydrogen or lower alkyl such as methyl or ethyl, $R_1$ is heterocyclealkyl or substituted heterocyclealkyl, such as 4-tetrohydropyranylmethyl, 2-(3-tetrahydrofuranyl)ethyl, 2-(4-tetrohydropyranyl)ethyl, 2-(2-1,3-dioxolanyl)ethyl, 2-(2-1,3-dioxanyl)ethyl, 2-tetrahydrofuranylmethyl and 3-tetrahydrofuranylmethyl, the chemical structure and nomenclature of which are shown in Table 2 below. $R_2$ is hydrogen or lower alkyl such as methyl or ethyl, $R_1$ is alkyl or substituted alkyl, such as methyl, ethyl, isopropyl, 3-methylbutyl, 2-butyl, 3-butyl, cyclopropylmethyl, 1-(1-cyclobutyl)ethyl, 2-(1-cyclohexyl)propyl, 2-(3-methyl)butyl, 3-cyclopentylpropyl, 3-cyclohexylpropryl, 3-methoxypropyl, 2-methoxyethyl, 2-methylsulfonylethyl, 2-(1-methoxyethyl), benzyl, and 1-[1-(4-methoxypheny)ethyl]. Alternatively, $R_1$ and $R_2$ together with the nitrogen to which they are attached form a optionally substituted heterocycle such as piperidinyl, pyrrolidinyl, homopiperidinyl, 4-phenylpiperidinyl, 4-propylpiperidinyl, 4-methylpiperidinyl, 2,6-dimethylmorpholinyl, 3-hydroxypyrrolidinyl and 4-hydroxypiperidinyl.

TABLE 2

| Structure | Name |
|---|---|
| (tetrahydropyran-CH2- structure) | 4-tetrohydropyranylmethyl |
| (tetrahydrofuran-CH2CH2- structure) | 2-(3-tetrahydrofuranyl)ethyl |
| (tetrahydropyran-CH2CH2- structure) | 2-(4-tetrohydropyranyl)ethyl |
| (1,3-dioxolanyl-CH2CH2- structure) | 2-(2-1,3-dioxolanyl)ethyl |
| (1,3-dioxanyl-CH2CH2- structure) | 2-(2-1,3-dioxanyl)ethyl |
| (tetrahydrofuran-CH2- 3-position structure) | 3-tetrahydrofuranylmethyl |
| (tetrahydrofuran-CH2- 2-position structure) | 2-tetrahydrofuranylmethyl |

In other more specific embodiments of structures (II) and (III), $R_3$ is hydrogen or lower alkyl such as methyl, $R_5$ and $R_6$ are each hydrogen or lower alkyl. $R_4$ is substituted aryl such as substituted phenyl. Representative substituted phenyls are 4-phenylphenyl, 4-(2-methyl-4-methoxyphenyl)phenyl, 4-(4-ethylphenyl)phenyl, 4-(4-methylphenyl)phenyl, 2-fluoro-4-(4-methoxyphenyl)phenyl, 2-fluoro-4-(4-methylphenyl)phenyl, 2-fluoro-4-(2-fluoro-4-methylphenyl)phenyl, 2-fluoro-4-(4-chlorophenyl)phenyl, (4-methoxyphenyl)phenyl and 2-fluoro-4-(4-trifluoromethoxyphenyl)phenyl. In this context, $R_1$ is hydrogen, cyclic alkyl, substituted cyclic alkyl, heterocycle, substituted heterocycle, heterocyclealkyl, substituted heterocyclealkyl, alkyl, or substituted alkyl. $R_2$ is hydrogen or lower alkyl such as methyl, ethyl or isopropyl. Alternatively, $R_1$ and $R_2$ together with the nitrogen to which they are attached form a heterocycle, optionally substituted with one or more alkyl, aryl, hydroxy or alkoxy. More specifically, particularly with respect to Structure (II), when $R_4$ is substituted phenyl as listed above, $R_1$ and $R_2$ can be any of the following combinations: $R_1$ and $R_2$ are each hydrogen. $R_2$ is hydrogen or lower alkyl such as methyl or ethyl, $R_1$ is cyclic alkyl or substituted cyclic alkyl such as cyclobutyl, cyclopentyl, cyclohexyl, 4-methylcyclohexyl, 4,4-dimethylcyclohexyl, 4-trifluoromethylcyclohexyl, 2-ethylcyclohexyl, 3,4-dimethylcyclohexyl and cycloheptyl. $R_2$ is hydrogen or lower alkyl such as methyl or ethyl, $R_1$ is heterocycle or substituted heterocycle such as 4-tetrohydropyranyl and 4-(1-benzylpiperidinyl). $R_2$ is hydrogen or lower alkyl such as methyl or ethyl, $R_1$ is heterocyclealkyl or substituted heterocyclealkyl, such as 4-tetrohydropyranylmethyl, 2-(3-tetrahydrofuranyl)ethyl, 2-(4-tetrohydropyranyl)ethyl, 2-(2-1,3-dioxolanyl)ethyl, 2-(2-1,3-dioxanyl)ethyl, 2-tetrahydrofuranylmethyl and 3-tetrahydrofuranylmethyl, the chemical structure and nomenclature of which are shown in Table 2 below. $R_2$ is hydrogen or lower alkyl such as methyl or ethyl, $R_1$ is alkyl or substituted alkyl, such as methyl, ethyl, isopropyl, 3-methylbutyl, 2-butyl, 3-butyl, cyclopropylmethyl, 1-(1-cyclobutyl)ethyl, 2-(1-cyclohexyl)propyl, 2-(3-methyl)butyl, 3-cyclopentylpropyl, 3-cyclohexylpropryl, 3-methoxypropyl, 2-methoxyethyl, 2-methylsulfonylethyl, 2-(1-methoxyethyl), benzyl, and 1-[1-(4-methoxypheny)ethyl]. Alternatively, $R_1$ and $R_2$ together with the nitrogen to which they are attached form a optionally substituted heterocycle such as piperidinyl, pyrrolidinyl, homopiperidinyl, 4-phenylpiperidinyl, 4-propylpiperidinyl, 4-methylpiperidinyl, 2,6-dimethylmorpholinyl, 3-hydroxypyrrolidinyl and 4-hydroxypiperidinyl.

In other more specific embodiments of structures (II) and (III), $R_3$ is hydrogen or lower alkyl such as methyl, $R_5$ and $R_6$ are each hydrogen or lower alkyl. $R_4$ is substituted alkyl such as substituted cyclohexyl. In this context, $R_1$ is hydrogen, cyclic alkyl, substituted cyclic alkyl, heterocycle, substituted heterocycle, heterocyclealkyl, substituted heterocyclealkyl, alkyl, or substituted alkyl. $R_2$ is hydrogen or lower alkyl such as methyl, ethyl or isopropyl. Alternatively, $R_1$ and $R_2$ together with the nitrogen to which they are attached form a heterocycle, optionally substituted with one or more alkyl, aryl, hydroxy or alkoxy. More specifically, particularly with respect to Structure (II), when $R_4$ is 4-chlorophenylcyclohexyl, $R_1$ and $R_2$ are the same or different and independently selected from hydrogen or methyl.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Compounds of structure (I) may also possess axial chirality that may result in atropisomers. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The compounds of this invention may be prepared by known organic synthesis techniques, including the methods described in more detail in the Examples. In general, compounds of structure (I) may be made by the following Reaction Scheme 1.

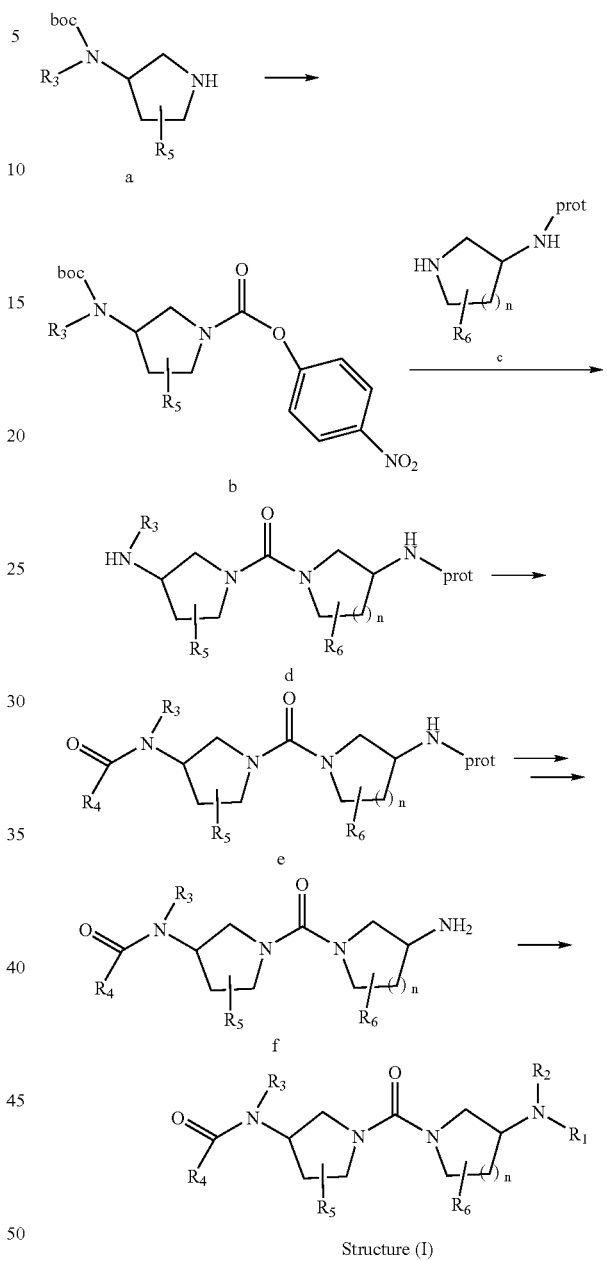

A mixture of p-nitrophenylchlorocarbonate and the appropriately substituted aminopyrrolidine a gives compound b. Compound b and protected heterocycle c in the presence of a base gives urea d after deprotection, which may then be acylated with an acyl-halide to give e. Deprotection gives compound f which may undergo reductive amination with aldehyde or alkylation with an appropriate halide to give compounds of structure (I).

The compounds of this invention may be evaluated for their ability to bind to a MCH receptor by techniques known in this field. For example, a compound may be evaluated for MCH receptor binding by monitoring the displacement of an iodonated peptide ligand, typically human [$^{125}$I]-MCH, from cells expressing individual melanin concentrating hormone receptor subtypes. To this end, whole cells expressing the desired melanin concentrating hormone receptor are subjected to nitrogen cavitation, and the membrane fraction is isolated by differential centrifugation. Stock solutions of test compounds are diluted serially in binding buffer (50 mM HEPES+10 mM MgCl$_2$+2 mM EGTA) and an equal volume mixed with [$^{125}$I]-MCH (0.2 nM final) diluted in binding buffer. Unlabeld MCH is included as a control. Membranes (5–10 µg total protein) are added to each test compound concentration and incubated for 30 minutes at room temperature. Bound radioligand is captured using GF/C glass fiber filter plates treated with 1% PEI and coated with 1% BSA. Free radioligand is removed by three sequential washes with wash buffer (PBS+0.01% Triton X-100). $K_i$ values are determined by data analysis using appropriate software, such as GraphPad Prizm, and data are plotted as counts of radiolabeled MCH bound versus the log concentration of test compound. Preferred compounds have a $K_i$ of less than 5 µM, and more preferably less than 1 µM. For example, the compounds of Example 10 through Example 22 have $K_i$ values of less than 1 µM.

In addition, functional assays of receptor activation have been defined for the MCH receptors based on their coupling to $G_q$ proteins. In response to MCH peptides, the MCH receptors couple to $G_q$ and activate phospholipase C resulting in an increased release of intracellular calcium. Melanin concentrating hormone receptor activity can be measured in HEK293 cells expressing individual melanin concentrating hormone receptors by direct measurement of $Ca^{2+}$ levels. For example, HEK293 cells expressing the desired MCH receptor are seeded into 96-well microtiter Poly-D-Lysine-coated plates at a density of 80,000 cells per well and allowed to adhere overnight with incubation at 37° C. in 5% $CO_2$. Test compounds are diluted in dilution buffer (HBSS+20 mM HEPES+0.1% BSA+2.5 mM Probenecid) and assessed for antagonist activity over a range of concentrations along with a control agonist MCH. Prior to the assay, cells are loaded with the calcium sensitive dye Fluo-4 for 1 hour at 37° C. Cells are then washed three times with assay buffer (dilution buffer without BSA), and brought to a final volume of 150 µl/well in assay buffer. At the time of assay, 50 µl of test compound is added to each well and allowed to incubate for 2 minutes at room temperature. MCH agonist peptide at a concentration of 10 nM is then added, and intracellular calcium release is measured in real-time using a fluorimetric imaging plate reader (FLIPR). $EC_{50}$ values are determined by data analysis using appropriate software such as GraphPad Prizm, and data are plotted as relative fluorescent units produced versus log concentration of compound.

As mentioned above, the compounds of this invention function as antagonists to the MCH receptor 1, and are thereby useful in the treatment of a variety of conditions or diseases including (but not limited to) eating disorders and obesity. The compounds of the present invention may also be used in combination therapy with agents that modify food intake or appetite, and are also included within the scope of this invention. Such agents include, but are not limited to, other MCH receptor ligands, or ligands of the leptin, NPY, melanocortin, serotonin or $B_3$ adrenergic receptors.

In another embodiment, compounds of this invention may be useful as anti-anxiety and/or anti-depression agents through interaction with the MCH receptor. These compounds may also be used in combination therapy with other anti-anxiety agents or anti-psychotics for the treatment of anxiety, depression, schizophrenia, and other CNS diseases.

In a further embodiment, compounds of this invention may be useful as anti-digestive disorder agents and a fertility and sexual function regulator through interaction with the MCH receptor. By using PCR of reverse-transcribed RNA, low levels of MCH gene transcripts were detected in testis, stomach, and intestine of Sprague-Dawley and Wistar rats. (Hervieu, NEUROENDOCRINOLOGY 1995 April; 61(4):348–64). In testis, the MCH transcripts and pro-MCH-derived peptide immunoreactivities were found at the periphery of the seminiferous tubules, suggesting expression in Sertoli cells. In the gastrointestinal (GI) tract, the cells expressing MCH RNA species and pro-MCH-derived peptides were predominantly expressed in the antral portion of the stomach and duodenum. The actual cellular location of expression suggests that MCH and associated peptides may play a role in spermatogenesis and in digestive processes. Further studies demonstrated effect of MCH peptide on water and electrolyte secretions at different levels of the GI tract by using the in situ ligated loop technique. (Hervieu, ENDOCRINOLOGY 1996 February; 137(2):561–71). MCH stimulated water, Na, and K fluxes at the proximal colon level and increased Na and K fluxes in the duodenum. MCH also increased bicarbonate absorption in the jejunum. More over, direct administration of MCH to ventromedial nucleus (VMN) and medial pre-optic area (MPOA) in female rats has been reported to initiate sexual activity (Gonzales et al., PEPTIDES 1996 17(1): 171–7). Further studies suggested that MCH has a stimulatory effect on LH release (Gonzales et al., NEUROENDOCRINOLOGY 1997 October; 66(4):254–62; Murray J., NEUROENDOCRINOL 2000 November; 12(11):1133–9). MCH has also been shown to be involved in release of other gonadotropins (Chiocchio, BIOL REPROD. 2001 May; 64(5): 1466–72). Thus antagonists of MCH may be useful in the development of agents to treat digestive disorders of the stomach and colon and may have a role in modulating fertility and sexual function.

In a further embodiment, compounds of this invention may be useful in treating urinary disorders. In studies of the cardiovascular and metabolic actions of intracerebroventricular (i.c.v.) infusion of MCH, and the pro-MCH derived peptide Neuropeptide-E-I (NEI), in conscious, chronically instrumented sheep, the i.c.v. infusion of MCH or NEI is shown to be capable of producing diuretic, natriuretic and kaliuretic changes in conscious sheep, triggered by a possible increase in plasma volume as indicated by the changes in hematocrit (Parkes, J NEUROENDOCRINOL. 1996 January; 8(1):57–63). These results, together with anatomical data reporting the presence of MCH/NEI in fluid regulatory areas of the brain, indicate that MCH/NEI may be an important peptide involved in the central control of fluid homeostasis in mammals. Hence, antagonists of MCH such as the compounds of the present invention may be used to treat urinary disorders including urinary incontinence, overactive bladder and urge urinary incontinence.

The following methods can be used to evaluate the effect of the treatment of obesity and anxiety in animal test objects:

Deprivation-Induced Feeding

In this acute model, the suppression of deprivation-induced food intake during the light cycle is examined. Male Sprague-Dawley rats are habituated to a palatable diet (Research Diets D12266B) over 3 days prior to testing. Rats are food deprived for ~23 hours before the test. On test day, animals are moved to a testing room, the drug is administered, and food intake is measured hourly up to 6 hours. Vehicle and 3 doses of drug are administered to separate groups of animals (n=8 per group). A two-way (time X dose) analysis of variance with Bonferroni post-hoc comparison is used to determine significant treatment effects.

Effects of Chronic Drug Administration in Diet-Induced Obese Rats

To induce obesity, male Sprague-Dawley rats are fed a medium high fat (32%) diet (Research Diets D12266B) for approximately 12 weeks prior to experimentation. Before drug administration begins, animals are habituated to handling and the oral dosing procedure for 1 week. During this period, food intake (corrected for spillage) and body weight are measured daily. Animals are subsequently divided into groups (n=10 per group), balanced for body weight and food intake. Groups consist of a vehicle control, a positive control (e.g., fenfluramine), and one of 3 drug doses. Treatments are then given orally once or twice daily over 4 weeks. Food intake and body weight are measured daily. At the end of dosing, animals are sacrificed and blood is taken to determine plasma levels of glucose, insulin, leptin, free fatty acids, and corticosterone. Gastrocnemius muscle, inguinal fat pads, and retroperitoneal fat pads are dissected and weighed. Dependent measures are analyzed using analysis of variance and Bonferroni post-hoc comparisons.

Guinea Pig Pup Ultrasonic Vocalization

Separation of guinea pig pups from their mothers and littermates elicits distress vocalizations. Studies have indicated that this behavioral response is sensitive to anxiolytic drugs. In this model of anxiety, guinea pig pups (5–26 days of age) are separated from their mothers and littermates and placed into a circular open field of 45 cm in diameter. The floor is divided into sections with painted lines so that locomotor activity as well as vocalizations can be monitored. A microphone is situated above the open field and connected to an Ultravox system (Noldus, Wageningen); the number of vocalizations emitted by each animal is then counted. Prior to testing, pups are screened for vocalizations. Pups that make fewer than 200 vocalizations during a 5 min isolation test are excluded from the study. Pups fulfilling this criterion are subsequently tested during five sequential tests of 5 minutes each, with 3–4 washout days between each test. Each pup receives vehicle, the positive reference compound and 3 doses of drug in a randomized, balanced design. Analysis of variance is used to determine differences among treatment conditions.

In another embodiment, pharmaceutical compositions containing one or more compounds of this invention are disclosed. For the purposes of administration, the compounds of the present invention may be formulated as pharmaceutical compositions. Pharmaceutical compositions of the present invention comprise a compound of structure (I) and a pharmaceutically acceptable carrier and/or diluent. The compound is present in the composition in an amount that is effective to treat a particular disorder of interest, and preferably with acceptable toxicity to the patient. Typically, the pharmaceutical composition may include a compound of this invention in an amount ranging from 0.1 mg to 250 mg per dosage depending upon the route of administration, and more typically from 1 mg to 60 mg. One skilled in the art can readily determine appropriate concentrations and dosages.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets that contain, in addition to a compound of this invention, dispersing and surface-active agents, binders, and lubricants. One skilled in this art may further formulate the compound in an appropriate manner, and in accordance with accepted practices, such as those disclosed in REMINGTON'S PHARMACEUTICAL SCIENCES, Gennaro, Ed., Mack Publishing Co., Easton, Pa. 1990.

In another embodiment, the present invention provides a method for treating a condition related to an MC receptor. Such methods include administration of a compound of the present invention to a warm-blooded animal in an amount sufficient to treat the condition. In this context, "treat" includes prophylactic administration. Such methods include systemic administration of compound of this invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions that may contain buffers, antioxidants, bacteriostats, and other additives commonly employed in such solutions.

The following examples are provided for purposes of illustration, not limitation.

EXAMPLES

Analytical Procedures

A—Analytical HPLC-MS (LC-MS)

HP 1100 series: equipped with an auto-sampler, an UV detector (220 nM and 254 nM), a MS detector (electrospray);

HPLC column: YMC ODS AQ, S-5, 5μ, 2.0×50 mm cartridge;

HPLC gradients: 1.5 mL/minute, from 10% acetonitrile in water to 90% acetonitrile in water in 2.5 minutes, maintaining 90% for 1 minute.

B—Prep. HPLC-MS

Gilson HPLC-MS equipped with Gilson 215 auto-sampler/fraction collector, an UV detector and a ThermoFinnigan AQA Single QUAD Mass detector (electrospray);

HPLC column: BHK ODS-O/B, 5μ, 30×75 mm

HPLC gradients: 35 mL/minute, 10% acetonitrile in water to 100% acetonitrile in 7 minutes, maintaining 100% acetonitrile for 3 minutes.

C—Analytical HPLC-MS (LC-MS)

HP 1100 series: equipped with an auto-sampler, an UV detector (220 nM and 254 nM), a MS detector (electrospray);

HPLC column: YMC ODS AQ, S-5, 5μ, 2.0×50 mm cartridge;

HPLC gradient: 1.5 mL/minute, from 10% acetonitrile in water to 90% acetonitrile in water in 2.5 minutes, maintaining 90% for 1 minute. Both acetonitrile and water have 0.025% TFA.

D—Analytical HPLC-MS (LC-MS)

HP 1100 series: equipped with an auto-sampler, an UV detector (220 nM and 254 nM), a MS detector (electrospray);

HPLC column: Phenomenex Synergi-Max RP, 2.0×50 mm column;
HPLC gradient: 1.0 mL/minute, from 5% acetonitrile in water to 95% acetonitrile in water in 13.5 minutes, maintaining 95% for 2 minute. Both acetonitrile and water have 0.025% TFA.

E—Analytical HPLC-MS (LC-MS)
HP 1100 series: equipped with an auto-sampler, an UV detector (220 nM and 254 nM), a MS detector (electrospray);
HPLC column: XTerra MS, $C_{18}$, 5μ, 3.0×250 mm cartridge;
HPLC gradient: 1.0 mL/minute, from 5% acetonitrile in water to 90% acetonitrile in water in 47.50 minutes, maintaining 99% for 8.04 minutes. Both acetonitrile and water have 0.025% TFA.

F—Analytical HPLC-MS (LC/MS)
Gilson 333/334 series: equipped with a Gilson 215 Liquid-Handler, a Gilson UV/VIS-156 UV detector (220 nM and 254 nM) and Finnigan AQA Mass Spec (ElectroSpray);
HPLC column: BHK Alpha, C-18, 5μ, 120A, 4.6×150 mm cartridge (PN: OB511546);
HPLC gradient: 3.6 mL/minute, maintaining 10% acetonitrile in water for 1 minute. Increasing from 10% acetonitrile in water to 90% acetonitrile in water over 12 minutes. Then increasing to 99% in 0.1 minutes and maintaining for 1.5 minutes. Both acetonitrile and water have 0.05% TFA.

G—Analytical HPLC-MS (SFC-MS)
HP 1100 series: equipped with an auto-sampler, an UV detector (220 nM and 254 nM), a MS detector (electrospray) and FCM 1200 $CO_2$ pump module;
HPLC column: Berger Pyridine, PYR 60A, 6μ, 4.6×150 mm column;
HPLC gradient: 4.0 mL/minute, 120 bar; from 10% methanol in supercritical $CO_2$ to 60% methanol in supercritical $CO_2$ in 1.67 minutes, maintaining 60% for 1 minute. Methanol has 1.5% water. Backpressure regulated at 140 bar.

H—Analytical HPLC (HPLC)
Shimadzu SIL-10A series: equipped with an auto-sampler and UV detector (220 nM and 254 nM);
HPLC column: ZORBAX SB-C18, 5μ, 4.6×250 mm cartridge (PN: 880975-902);
HPLC gradient: 2.0 mL/minute, maintaining 5% acetonitrile in water for 4 minutes then to 10% acetonitrile in 0.1 min and 10% acetonitrile in water to 95% acetonitrile in water in 46 minutes, then increasing to 99% in 0.1 minutes and maintaining for 10.8 minutes. Both acetonitrile and water have 0.025% TFA.

I—Analytical HPLC (HPLC)
HP 1100 series: equipped with an auto-sampler and UV detector (220 nM and 254 nM);
HPLC column: Waters Symetry, C-8, 5μ, 4.6×150 mm cartridge (PN: WAT045995);
HPLC gradient: 2.8 mL/minute, maintaining 5% acetonitrile in water for 1 minute. Increasing to 10% acetonitrile in water in 0.1 minutes. Then increasing to 90% acetonitrile in water in 15 minutes. Then increasing to 99% in 0.1 minutes and maintaining for 2.4 minutes. Both acetonitrile and water have 0.05% TFA.

Abbreviations:
Boc-Phe-CHO: (S)-(tertbutoxycarbonylamino)-3-phenyl-propional
BOC: tert-butoxycarbonyl
DCM: dichloromethane
DMF: dimethylformamide
DMSO: dimethylsulfoxide
EDC: 1-(3-dimethylaminopropyl)-3-ethylcarbodiimide hydrochloride
FMOC: N-(9-fluorenylmethoxycarbonyl)
HOBt: 1-hydroxybenzotriazole hydrate
HBTU: O-(1H-Benzotriazol-1-yl)-N,N,N',N'-tetramethyluroniumhexafluorophosphate
$NaBH(OAc)_3$: Sodium Triacetoxyborohydride
Pd—C: Palladium (10%) on Carbon
TFA: Trifluoroacetic acid
Rt: Retention time Example 1

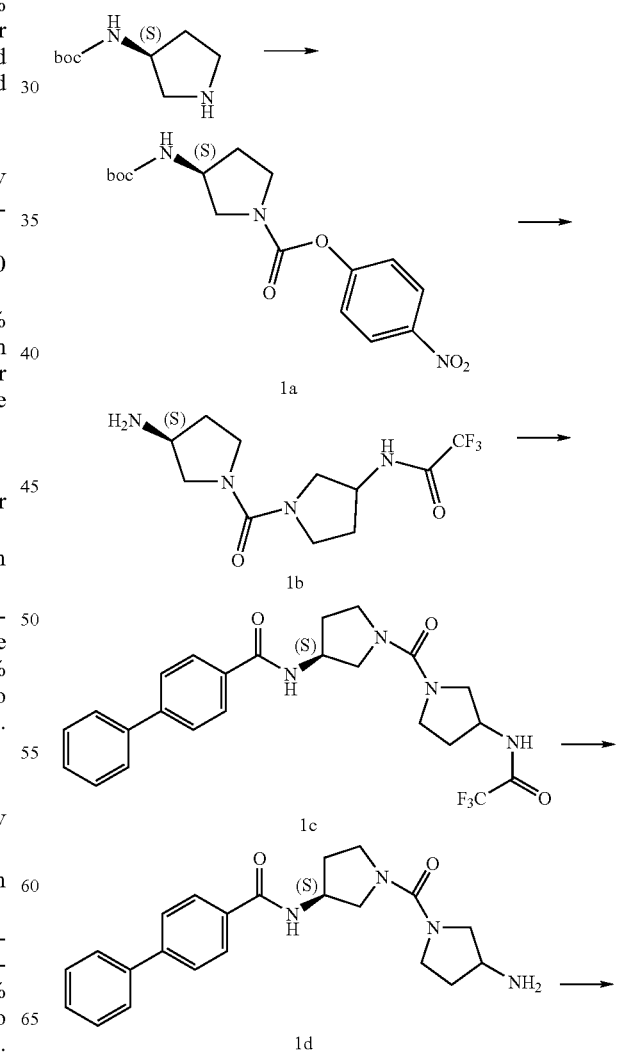

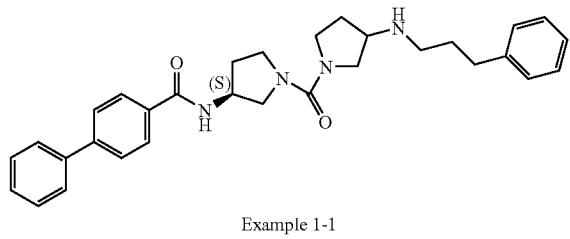

Example 1-1

Step 1A:

To a stirred solution of 4-nitrophenyl chloroformate (2.21 g, 11.0 mmol) in tetrahydrofuran (10 mL) at 0° C. under nitrogen was added triethylamine (3.0 mL, 22.0 mmol) followed by a solution of (S)-(−)-3-tert-butoxycarbonylaminopyrrolidine (2.0 g, 10.7 mmol) in tetrahydrofuran (10 mL). After warming to room temperature, the reaction mixture was stirred for 2 hours. The suspension was filtered (to remove triethylamine hydrochloride salt) and the filtrate was concentrated in vacuo to yield a yellow oil. The oil was dissolved in ethyl acetate and sequentially washed with aqueous hydrochloric acid solution (0.5 M) and brine. After drying (MgSO$_4$), concentration in vacuo afforded 3.59 g (95%) of 1a as a cream solid. $^1$H-NMR (300 MHz, CDCl$_3$) δ 8.24–8.27 (m, 2 H), 7.30–7.35 (m, 2 H), 4.69 (m, 1 H), 4.29 (m, 1 H), 3.57–3.79 (m, 2 H), 3.34–3.49 (m, 2 H), 2.20 (m, 1 H), 1.92 (m, 1 H), 1.47 (s, 9 H); LC-MS 252.0 (MH$^+$—C$_5$H$_8$O$_2$).

Step 1B:

A solution of pyrrolidine 1a (3.59 g, 10.2 mmol), (RS)-(3)-(trifluoroacetamido)pyrrolidine hydrochloride (2.68 g, 12.2 mmol) and triethylamine (2.84 mL, 20.4 mmol) in dimethylformamide (30 mL) was heated in a sealed tube at 90° C. for 2 hours. After cooling to room temperature the reaction mixture was added to water (200 mL). The resulting organic suspension was extracted into ethyl acetate and sequentially washed with aqueous hydrochloric acid solution (0.5 M), water, saturated aqueous sodium bicarbonate solution, brine, and then was dried (MgSO$_4$). Concentration in vacuo afforded a cream solid. The solid was redissolved in a mixture of dichloromethane (30 mL) and trifluoroacetic acid (10 mL) and stirred at room temperature for 2 hours. Concentration in vacuo afforded 4.16 g of 1b as an orange oil. LC-MS 295.0 (MH$^+$).

Step 1C:

To a stirred solution of pyrrolidine 1b (4.16 g, 10.2 mmol) and triethylamine (4.20 mL, 30.0 mmol) in dichloromethane (20 mL) at room temperature under an inert atmosphere was added a solution of 4-biphenylcarbonylchloride (2.17 g, 10.2 mmol) in dichloromethane (10 mL) dropwise. The solution was stirred for 15 hours then washed sequentially with water, aqueous hydrochloric acid solution (0.5 M), saturated aqueous sodium bicarbonate solution, brine, and dried with MgSO$_4$. Concentration in vacuo gave an oil which was purified by flash column chromatography (gradient elution with 100% ethyl acetate to 10% methanol in ethyl acetate) to afford 1.40 g (30%) of 1c as a yellow oil. LC-MS 475.2 (MH$^+$)

Step 1D:

A stirred solution of pyrrolidine 1c (1.40 g, 3.0 mmol) and potassium carbonate (2.04 g, 14.8 mmol) in a mixture of methanol (30 mL) and water (1 mL), was refluxed for 15 hours. After cooling to room temperature the mixture was concentrated in vacuo to give a solid which was suspended in saturated aqueous sodium bicarbonate solution (30 mL) and stirred for 10 minutes. The solid residue was filtered and dried to afford 599 mg (54%) of 1d. $^1$H-NMR (300 MHz, Methanol-d$_4$) δ 7.90–7.92 (m, 2 H), 7.70–7.73 (m, 2 H), 7.65–7.68 (m, 2 H), 7.44–7.49 (m, 2 H), 7.37 (m, 1 H), 4.55 (ddd, J=12.3, 6.0, 6.0 Hz, 1 H), 3.77 (ddd, J=10.5, 6.0, 4.8 Hz, 1 H), 3.41–3.68 (m, 7 H), 3.14 (dd, J=9.9, 5.1 Hz, 1 H), 2.23 (ddd, J=12.9, 12.9, 6.9 Hz, 1 H), 2.01–2.12 (m, 2 H), 1.71 (ddd, J=13.5, 13.5, 6.9 Hz, 1 H); LC-MS 379.2 (MH$^+$).

Step 1E:

A solution of pyrrolidine 1d (25 mg, 0.066 mmol), 3-phenylpropionaldehyde (0.40 mmol) and acetic acid (0.10 mL, 1.74 mmol) in methanol (1 mL) was stirred at room temperature for 3 hours. Sodium borohydride (30 mg, 0.79 mmol) was added in one portion and the reaction mixture was stirred for 12 hours. The reaction solution was purified directly by Preparative HPLC-MS to afford 5 mg of Example 1-1, as the trifluoroacetate salt. LC-MS 497.2 (MH$^+$)

| Ex. | R$_1$ | R$_2$ | MW | MH$^+$ |
|---|---|---|---|---|
| 1-1 | –CH$_2$CH$_2$CH$_2$–phenyl | H | 496.65 | 497.2 |
| 1-2 | –CH$_2$–cyclohexyl | H | 460.62 | 461.3 |
| 1-3 | –CH$_2$–cyclohexyl | H | 474.64 | 475.2 |
| 1-4 | –CH$_2$–benzyl | H | 468.60 | 469.2 |
| 1-5 | –CH$_2$–cyclobutyl | H | 432.57 | 433.2 |
| 1-6 | –CH$_2$–cyclopropyl | H | 432.57 | 433.2 |

-continued

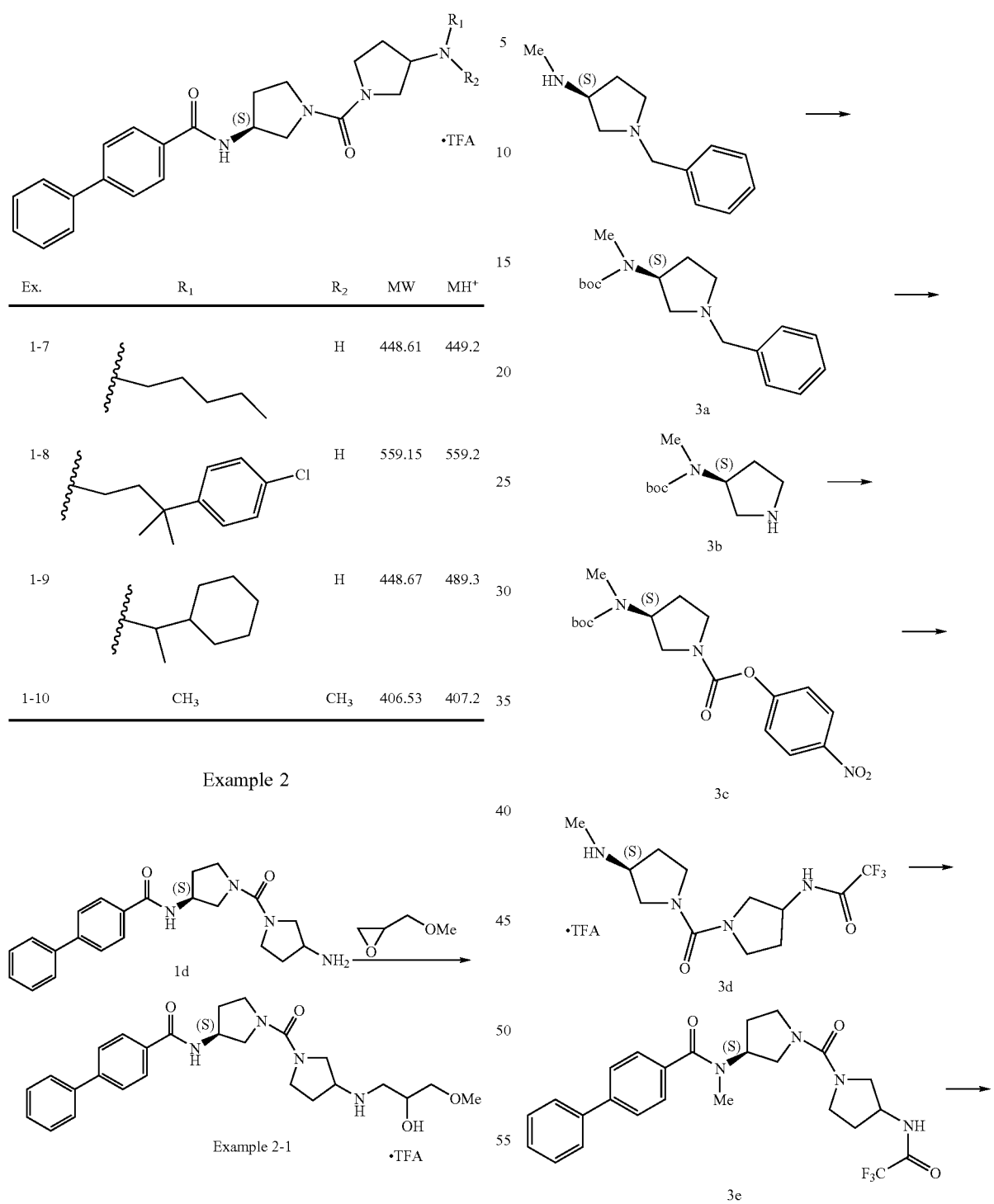

| Ex. | R₁ | R₂ | MW | MH⁺ |
|---|---|---|---|---|
| 1-7 | (pentyl chain) | H | 448.61 | 449.2 |
| 1-8 | (CH₂CH₂C(CH₃)₂-4-chlorophenyl) | H | 559.15 | 559.2 |
| 1-9 | (1-cyclohexylethyl) | H | 448.67 | 489.3 |
| 1-10 | CH₃ | CH₃ | 406.53 | 407.2 |

Example 2

Step 2A:

A mixture of pyrrolidine 1d (25 mg, 0.066 mmol), glycidyl methyl ether (7 mg, 0.079 mmol) and potassium carbonate (50 mg, 0.36 mmol) in dimethylformamide (1 mL), was heated in a sealed tube at 90° C. for 12 hours. The reaction mixture was filtered and the filtrate was purified directly by Preparative HPLC-MS to afford 5 mg (13%) of Example 2-1 as a colorless oil. LC-MS 467.2 (MH⁺).

Example 3

-continued

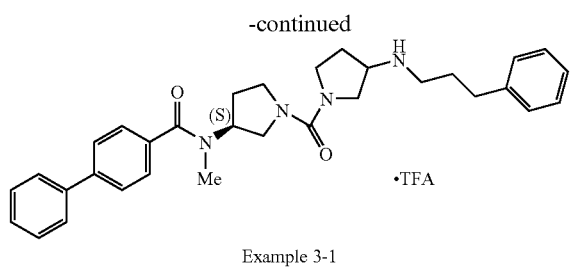

Example 3-1

Step 3A:

To a stirred solution of (S)-(+)-3-(methylamino)-1-benzylpyrrolidine (1.54 g, 8.1 mmol) and triethylamine (2.23 mL, 16.0 mmol) in dichloromethane (30 mL) at room temperature and under an inert atmosphere, was added a solution of di-tert-butyl dicarbonate (1.86 g, 8.5 mmol) in dichloromethane (20 mL), dropwise. The solution was stirred for 2 hours then concentrated in vacuo, to afford 2.35 g of 3a as a yellow oil. $^1$H-NMR (300 MHz, CDCl$_3$) δ 7.21–7.32 (m, 5 H), 3.65 (d, J=12.9 Hz, 1 H), 3.50 (d, J=12.9 Hz, 1 H), 2.82 (s, 3 H), 2.78 (m, 1 H), 2.47–2.59 (m, 2 H), 2.34 (m, 1 H), 2.13 (m, 1 H), 1.64–1.80 (m, 2H), 1.44 (s, 9H); LC-MS 291.1 (MH$^+$), 235.1 (MH$^+$—C$_4$H$_8$).

Step 3B:

Pyrrolidine 3a (7.10 g, 0.0245 mol) was combined with 10% palladium on carbon (50% water) (7.84 g, 0.00370 mol) and ammonium formate (9.20 g, 0.147 mol) in ethanol (300 mL) and was heated to reflux for 110 minutes. The mixture was cooled and filtered through celite and washed with additional ethanol. The filtrate was dried with magnesium sulfate and concentrated to afford 3.70 g (76%) of 3b as a clear gum. LC-MS 200 (MH+).

Step 3C:

To a stirred solution of 4-nitrophenyl chloroformate (1.65 g, 8.2 mmol) in tetrahydrofuran (10 mL) at 0° C. and under an inert atmosphere, was added triethylamine (2.28 mL, 16.4 mmol) followed by a solution of amine 3b (1.64 g, 8.2 mmol) in tetrahydrofuran (10 mL). After allowing to warm to room temperature, the reaction mixture was stirred for 2 hours. The suspension was filtered (to remove triethylamine hydrochloride salt) and the filtrate was concentrated in vacuo to yield a yellow oil. The oil was redissolved in ethyl acetate and sequentially washed with aqueous hydrochloric acid solution (0.5 M) and brine. Drying over MgSO$_4$ followed by concentration in vacuo afforded 2.02 g (68%) of 3c as a cream solid. LC-MS 266.0 (MH$^+$—C$_5$H$_8$O$_2$).

Step 3D:

A solution of pyrrolidine 3c (2.02 g, 5.5 mmol), (RS)-(3)-(trifluoroacetamido)pyrrolidine hydrochloride (1.45 g, 6.6 mmol) and triethylamine (1.53 mL, 11.0 mmol) in dimethylformamide (30 mL) was heated in a sealed tube at 90° C. for 2 hours. After cooling-to room temperature, the reaction mixture was added to water (200 mL). The resulting organic suspension was extracted into ethyl acetate and sequentially washed with aqueous hydrochloric acid solution (0.5 M), water, saturated aqueous sodium bicarbonate solution, and brine. The organic layer was dried (MgSO$_4$) and concentration in vacuo afforded a cream solid. The solid was redissolved in a mixture of dichloromethane (30 mL) and trifluoroacetic acid (10 mL) and stirred at room temperature for 1 hour. Concentration in vacuo afforded 2.30 g of 3d as a cream solid. LC-MS 309.0 (MH$^+$)

Step 3E:

To a stirred solution of pyrrolidine salt 3d (2.30 g, 5.5 mmol) and triethylamine (5.56 mL, 40 mmol) in dichloromethane (20 mL) at room temperature under an inert atmosphere was added dropwise a solution of 4-biphenylcarbonylchloride (1.73 g, 8.0 mmol) in dichloromethane (10 mL). The solution was stirred for 15 hours then washed sequentially with water, aqueous hydrochloric acid solution (0.5 M), saturated aqueous sodium bicarbonate solution, brine, and then was dried (MgSO$_4$). Concentration in vacuo gave an oil which was purified by flash column chromatography (gradient elution with 100% ethyl acetate to 10% methanol in ethyl acetate) to afford 1.50 g (58%) of 3e as a yellow oil. LC-MS 489.2 (MH$^+$).

Step 3F:

A stirred solution of pyrrolidine 3e (1.50 g, 3.1 mmol) and potassium carbonate (2.04 g, 14.8 mmol) in a mixture of methanol (30 mL) and water (1 mL), was heated to reflux for 15 hours. After cooling to room temperature the mixture was concentrated in vacuo to give a solid which was suspended in saturated aqueous sodium bicarbonate solution (30 mL) and stirred for 10 minutes. The solid residue was filtered and dried in vacuo to afford 300 mg (25%) of 3f. $^1$H-NMR (300 MHz, Methanol-d$_4$) δ 7.37–7.75 (m, 9 H), 3.30–3.70 (m, 9 H); 3.17 (m. 1 H), 3.03 (s, 3 H), 2.00–2.30 (m, 3 H), 1.75 (m, 1 H); LC-MS 393.2 (MH$^+$).

Step 3G:

A solution of pyrrolidine 3f (30 mg, 0.08 mmol), 3-phenylpropionaldehyde (0.30 mmol) and acetic acid (0.10 mL, 1.74 mmol) in methanol (1 mL) was stirred at room temperature for 3 hours. Sodium borohydride (150 mg, 3.95 mmol) was added in one portion and the reaction mixture was stirred for a further 12 hours. The reaction solution was purified directly by Preparative HPLC-MS to afford 12 mg of Example 3-1, as the trifluoroacetate salt. LC-MS 511.2 (MH$^+$).

Using the appropriate starting materials, the following compounds were prepared according to the procedures above.

| Ex. | R$_1$ | R$_2$ | MW | MH$^+$ |
|---|---|---|---|---|
| 3-1 | (3-phenylpropyl) | H | 510.68 | 511.2 |
| 3-2 | (cyclohexylmethyl) | H | 474.64 | 475.2 |

-continued

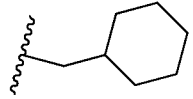

| Ex. | R₁ | R₂ | MW | MH⁺ |
|---|---|---|---|---|
| 3-3 | 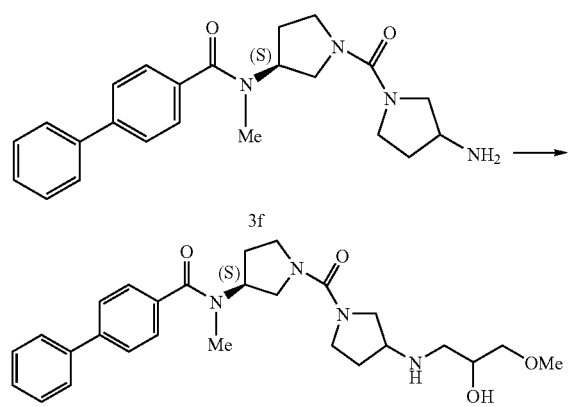 | H | 488.67 | 489.3 |
| 3-4 | 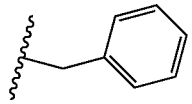 | H | 482.63 | 483.2 |
| 3-5 | 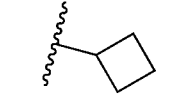 | H | 446.59 | 447.2 |
| 3-6 |  | H | 446.59 | 447.2 |
| 3-7 | 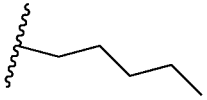 | H | 462.63 | 463.2 |
| 3-8 | CH₃ | CH₃ | 420.55 | 421.2 |

Example 4

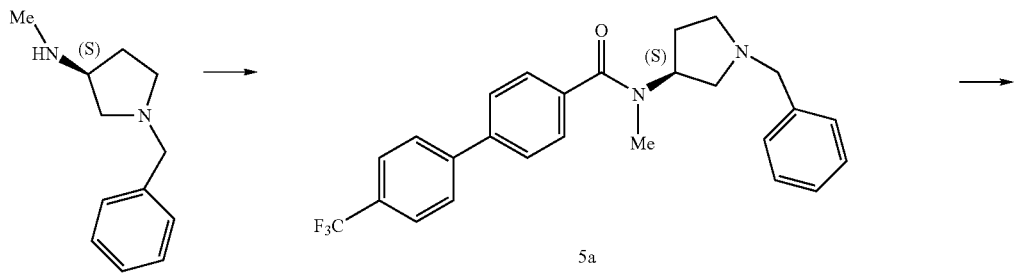

Step 4A:
A mixture of pyrrolidine 3f (25 mg, 0.06 mmol), glycidyl methyl ether (0.08 mmol) and potassium carbonate (50 mg, 0.36 mmol) in dimethylformamide (1 mL), was heated in a sealed tube at 90° C. for 12 hours. The reaction mixture was filtered and the filtrate was purified directly by Preparative HPLC-MS to afford 3 mg of Example 4-1, as the trifluoroacetate salt. LC-MS 481.2 (MH⁺)

Using the appropriate starting materials, the following compounds were prepared according to the procedures above.

| Ex. | R | MW | MH⁺ |
|---|---|---|---|
| 4-1 | CH₃ | 480.61 | 481.2 |
| 4-2 | Ph | 542.68 | 543.2 |

Example 5

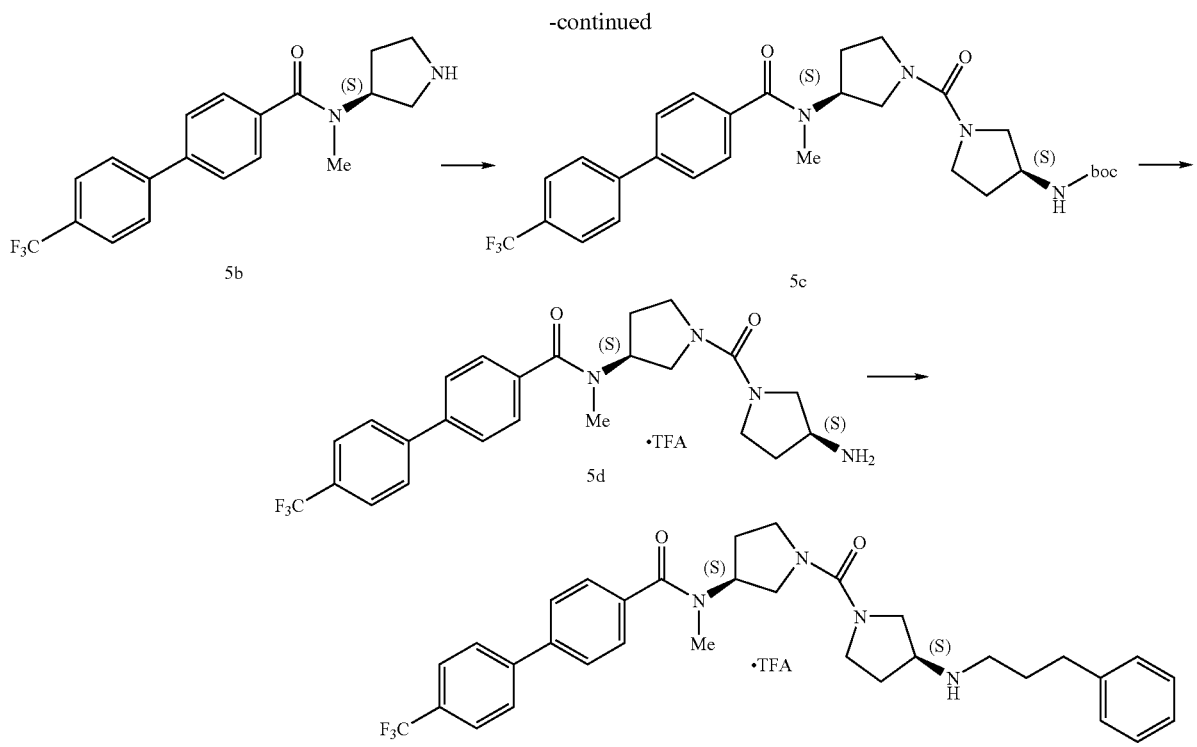

Example 5-1

Step 5A:

To a stirred solution of (S)-(+)-1-benzyl-3-(methylamino) pyrrolidine (335 mg, 1.76 mmol) and triethylamine (0.56 mL, 4.0 mmol) in dichloromethane (20 mL) at room temperature and under an inert atmosphere, was added dropwise a solution of 4-(4-trifluoromethylphenyl)benzoyl chloride (prepared from 4-(4-trifluoromethylphenyl)benzoic acid and thionyl chloride) (500 mg, 1.76 mmol) in dichloromethane (10 mL). The solution was stirred for 48 hours then concentrated in vacuo to give a yellow oil. The oil was redissolved in ethyl acetate and sequentially washed with water, brine, and dried with MgSO$_4$. Concentration in vacuo afforded 767 mg of compound 5a as a yellow oil. LC-MS 439.1 (MH$^+$).

Step 5B:

Palladium hydroxide (20% palladium on activated carbon, 60% moisture content) (250 mg) was added to a solution of N-benzyl amine 5a (767 mg, 1.76 mmol) in methanol (30 mL). The resulting mixture was agitated at room temperature under 45 psi of hydrogen gas for 2.5 hours. The suspension was filtered (to remove palladium residues) and the filtrate was concentrated in vacuo to afford 383 mg (63%) of 5b as a yellow oil. $^1$H-NMR (300 MHz, CDCl$_3$) δ 7.63–7.74 (m, 6 H), 7.51 (d, J=8.1 Hz, 2 H), 2.50–3.40 (m, 7 H), 3.04 (s, 3 H), 1.98 (m, 1 H); LC-MS 349.2 (MH$^+$).

Step 5C:

In a sealed tube, a stirred solution of pyrrolidine 5b (192 mg, 0.55 mmol), pyrrolidine 1a (193 mg, 0.55 mmol), triethylamine (0.50 mL, 3.6 mmol), and N,N-dimethyl-4-aminopyridine (50 mg, 0.41 mmol) in dimethylformamide (20 mL), was heated at 100° C. under an inert atmosphere for 12 hours. After cooling to room temperature, the mixture was added to water. The resulting organic suspension was extracted into ethyl acetate and sequentially washed with water, aqueous hydrochloric acid solution (0.5 M), saturated aqueous sodium bicarbonate solution, brine, and dried with MgSO$_4$. Concentration in vacuo gave an oil which was purified by flash column chromatography (gradient elution with 100% ethyl acetate to 5% methanol in ethyl acetate) to afford 81 mg of compound 5c as a colorless oil. $^1$H-NMR (300 MHz, CDCl$_3$) δ 7.64–7.75 (m, 6 H), 7.50 (d, J=8.1 Hz, 2 H), 4.64 (brm, 1 H), 4.13 (brm, 1 H), 3.40–3.62 (m, 7 H), 3.24 (dd, J=10.5, 5.7 Hz, 1 H), 3.01 (s, 3 H), 2.05–2.20 (m, 3 H), 1.72–1.84 (m, 2 H), 1.44 (s, 9 H); LC-MS 561.1 (MH$^+$).

Step 5D:

A solution of pyrrolidine 5c (81 mg, 0.14 mmol) in a mixture of dichloromethane (5 mL) and trifluoroacetic acid (2 mL) was stirred at room temperature for 1 hour. Concentration in vacuo afforded 83 mg of 5d as a yellow oil. LC-MS 461.3 (MH$^+$).

Step 5E:

A solution of pyrrolidine 5d (40 mg, 0.071 mmol), 3-phenylpropionaldehyde (0.075 mmol) and triethylamine (1.44 mmol) in methanol (1 mL) was stirred at room temperature for 3 hours. Sodium borohydride (100 mg, 2.63 mmol) was added in one portion and the reaction mixture was stirred for a further 12 hours. The reaction solution was purified directly by Preparative HPLC-MS to afford Example 5-1 as the trifluoroacetate salt (5 mg of a colorless oil). LC-MS 579.5 (MH$^+$).

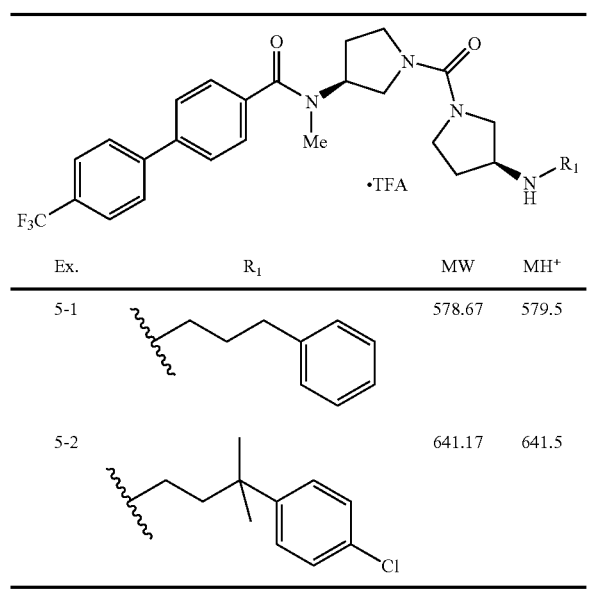

| Ex. | R₁ | MW | MH⁺ |
|---|---|---|---|
| 5-1 | ~~~CH₂CH₂CH₂-phenyl | 578.67 | 579.5 |
| 5-2 | ~~~CH₂CH₂C(CH₃)₂-(4-Cl-phenyl) | 641.17 | 641.5 |

Example 6

Step 6A:

Using (R)-(−)-1-benzyl-3-(methylamino)pyrrolidine (335 mg, 1.76 mmol) as starting material and following the procedure of Step 27A, 770 mg of compound 6a was isolated as a yellow oil. LC-MS 439.0 (MH⁺).

Step 6B:

Starting with compound 6a (770 mg, 1.76 mmol) and following the procedure described in Step 27B, yielded 469 mg (77%) of 6b as a yellow oil. $^1$H-NMR (300 MHz, CDCl$_3$) δ 7.63–7.74 (m, 6 H), 7.51 (d, J=8.1 Hz, 2 H), 2.50–3.40 (m, 7 H), 3.04 (s, 3 H), 1.98 (brs, 1 H); LC-MS 349.0 (MH⁺).

Step 6C:

Prepared from 6b (235 mg, 0.68 mmol) and 1a (238 mg, 0.68 mmol) according to the procedure described in Step 27C, yielded 135 mg (36%) of 6c as a colorless oil. $^1$H-NMR (300 MHz, CDCl$_3$) δ 7.64–7.75 (m, 6 H), 7.51 (d, J=8.1 Hz, 2 H), 4.64 (brm, 1 H), 4.19 (brm, 1 H), 3.36–3.66 (m, 7 H), 3.22 (m, 1 H), 3.01 (s, 3 H), 2.01–2.10 (m, 4 H), 1.86 (m, 1 H), 1.44 (s, 9 H); LC-MS 561.3 (MH⁺).

Step 6D:

A solution of pyrrolidine 6c (135 mg, 0.24 mmol) in a mixture of dichloromethane (5 mL) and trifluoroacetic acid (2 mL) was stirred at room temperature for 1 hour. Concentration in vacuo afforded 137 mg of 6d as a yellow oil. LC-MS 461.3 (MH⁺).

Step 6E:

A solution of pyrrolidine 6d (40 mg, 0.071 mmol), 3-phenylpropionaldehyde (0.075 mmol) and triethylamine (1.44 mmol) in methanol (1 mL) was stirred at room temperature for 3 hours. Sodium borohydride (100 mg, 2.63 mmol) was added in one portion and the reaction mixture was stirred for a further 12 hours. The reaction solution was purified directly by Preparative HPLC-MS to afford Example 6-1 as the trifluoroacetate salt (4 mg of a colorless oil). LC-MS 579.5 (MH⁺).

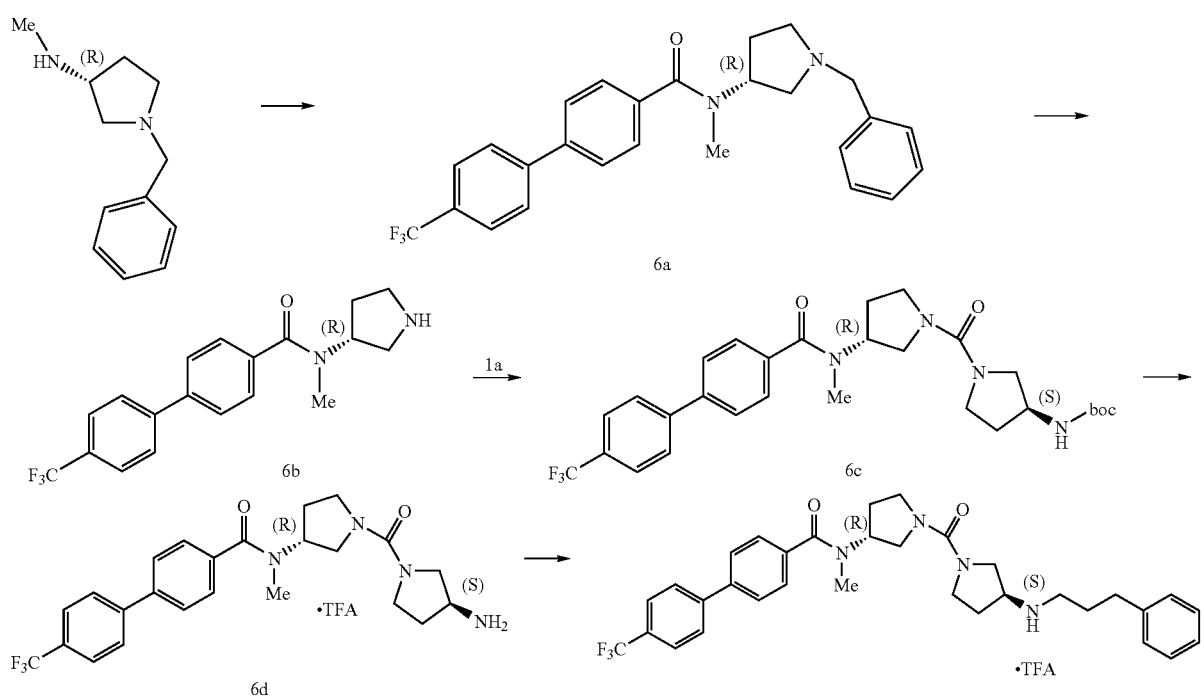

Example 6-1

Using the appropriate starting materials, the following compounds were prepared according to the procedures described above.
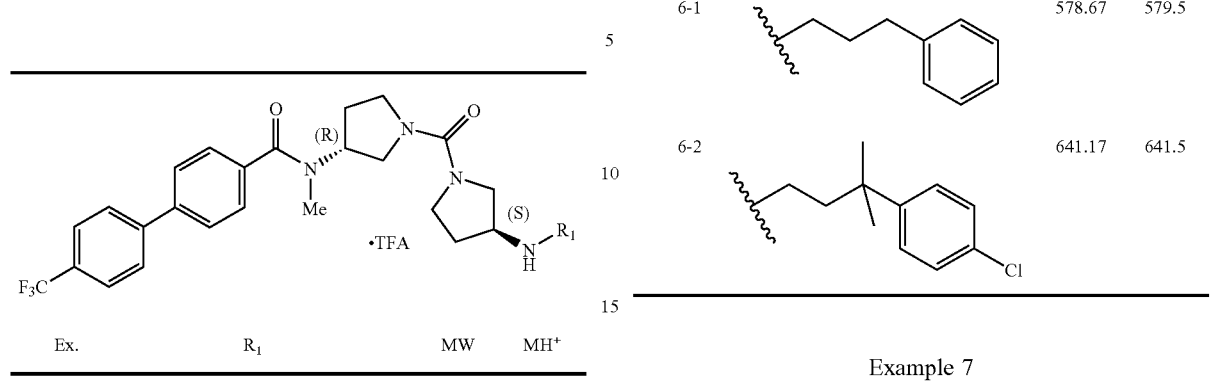
| Ex. | R₁ | MW | MH⁺ |
|---|---|---|---|
| 6-1 | (3-phenylpropyl) | 578.67 | 579.5 |
| 6-2 | (2-(4-chlorophenyl)-2-methylpropyl with methyl branch) | 641.17 | 641.5 |
Example 7
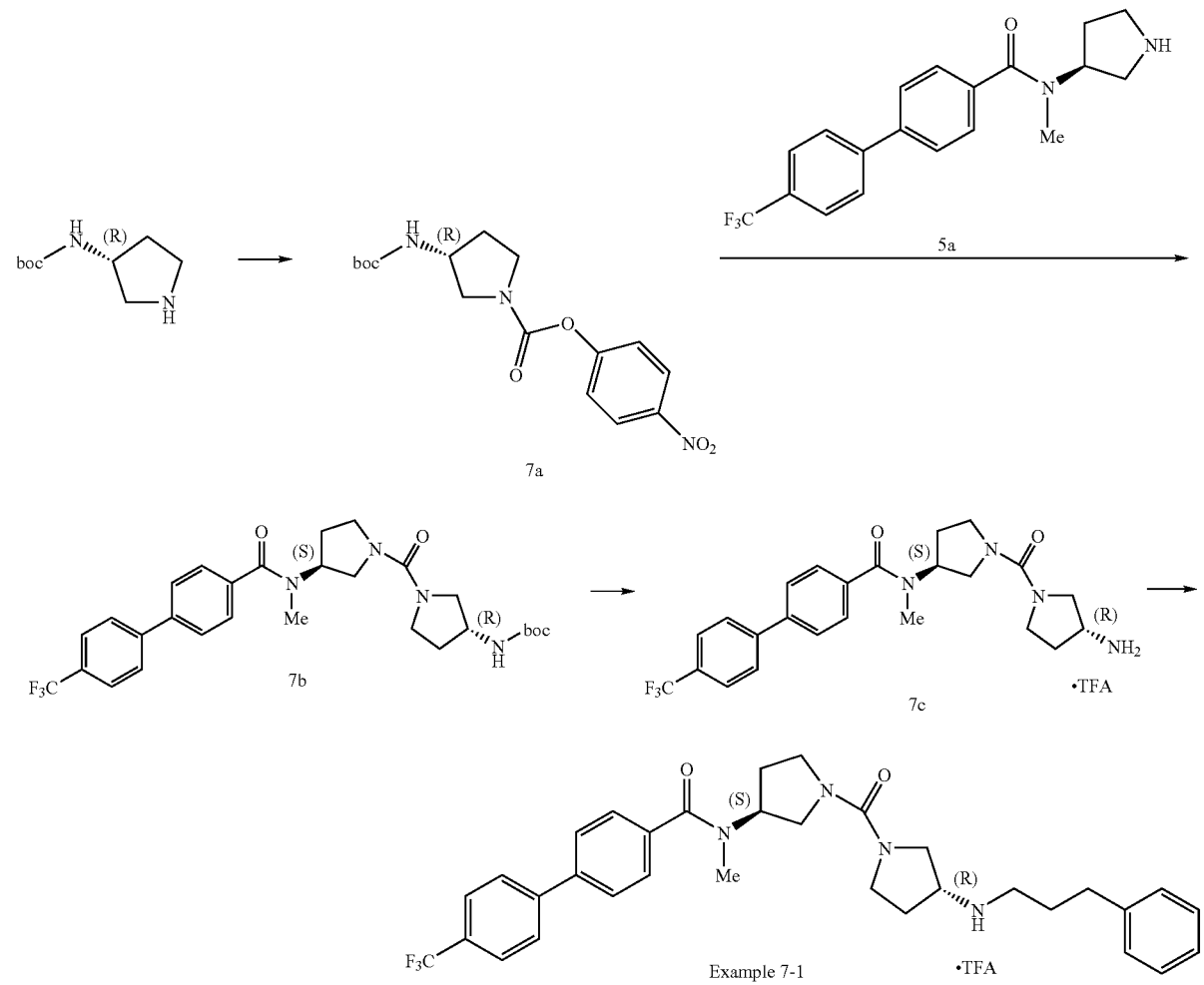

Step 7A:

Prepared from (R)-(+)-3-tert-butoxycarbonylaminopyrrolidine (855 mg, 4.59 mmol) according to the procedure described in Step 12A, 1.33 g (83%) of compound 7a was isolated as a cream colored solid. $^1$H-NMR (300 MHz, CDCl$_3$) δ 8.24–8.27 (m, 2 H), 7.30–7.35 (m, 2 H), 4.69 (m, 1 H), 4.29 (m, 1 H), 3.57–3.79 (m, 2 H), 3.34–3.49 (m, 2 H), 2.20 (m, 1 H), 1.92 (m, 1 H), 1.47 (s, 9 H); LC-MS 252.2 (MH$^+$—C$_5$H$_8$O$_2$).

Step 7B:

Prepared from 5a (192 mg, 0.55 mmol) and 7a (193 mg, 0.55 mmol) according to the procedure described in Step 27C, 116 mg (38%) of compound 7b was isolated as a colorless oil: $^1$H-NMR (300 MHz, CDCl$_3$) δ 7.64–7.75 (m, 6 H), 7.51 (d, J=8.1 Hz, 2 H), 4.64 (brm, 1 H), 4.19 (brm, 1 H), 3.36–3.66 (m, 7 H), 3.22 (m, 1 H), 3.01 (s, 3 H), 2.01–2.10 (m, 4 H), 1.86 (m, 1 H), 1.45 (s, 9 H); LC-MS 561.1 (MH$^+$).

Step 7C:

A solution of compound 7b (116 mg, 0.21 mmol) in trifluoroacetic acid (2 mL) and dichloromethane (5 mL) was stirred for 1 hour. The reaction mixture was concentrated in vacuo to afford 115 mg (96%) of 7c as a colorless oil. LC-MS 461.3 (MH$^+$).

Step 7D:

A solution of pyrrolidine 7c (40 mg, 0.071 mmol), 3-phenylpropionaldehyde (0.075 mmol) and triethylamine (1.44 mmol) in methanol (1 mL) was stirred at room temperature for 3 hours. Sodium borohydride (100 mg, 2.63 mmol) was added in one portion and the reaction mixture was stirred for a further 12 hours. The reaction solution was purified directly by Preparative HPLC-MS to afford Example 7-1 as the trifluoroacetate salt (6 mg of a colorless oil). LC-MS 579.5 (MH$^+$).

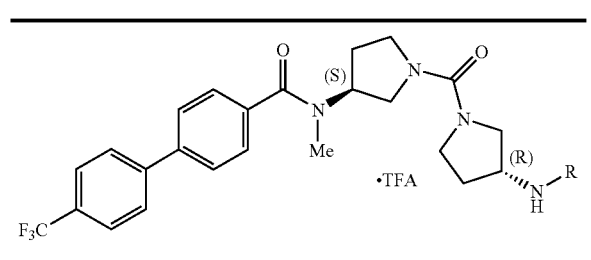

| Ex. | R$_1$ | MW | MH$^+$ |
|---|---|---|---|
| 7-1 | (3-phenylpropyl) | 578.67 | 579.5 |
| 7-2 | (3-(4-chlorophenyl)-3-methylbutyl) | 641.17 | 641.5 |
| 7-3 | (cyclohexylmethyl) | 556.67 | 557.3 |

Example 8

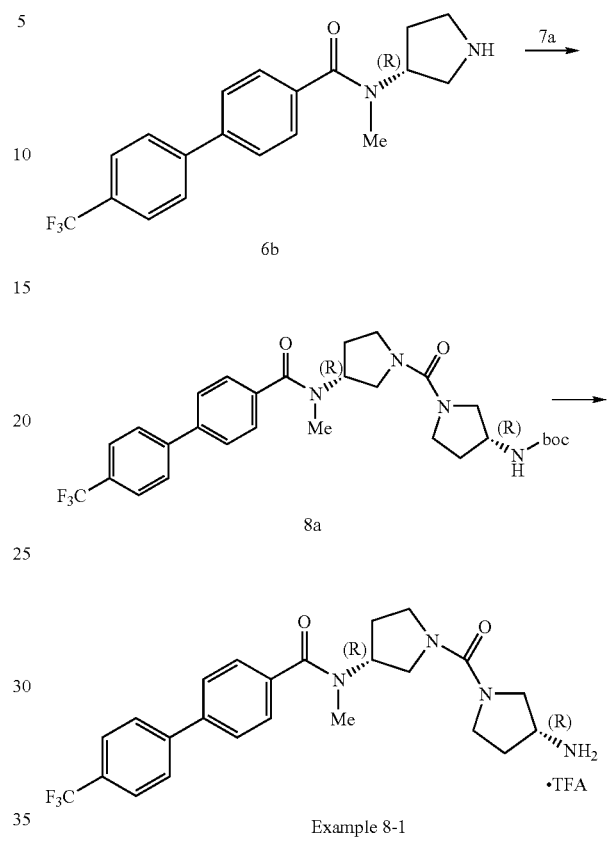

Step 8A:

Prepared from compounds 6b (235 mg, 0.68 mmol) and 7a (238 mg, 0.68 mmol), according to the procedure described for Step 27C resulted in 158 mg (42%) of compound 8a as a colorless oil. $^1$H-NMR (300 MHz, CDCl$_3$) δ 7.64–7.75 (m, 6 H), 7.50 (d, J=8.1 Hz, 2 H), 4.64 (brm, 1 H), 4.13 (brm, 1 H), 3.40–3.62 (m, 7 H), 3.24 (dd, J=9.9, 5.7 Hz, 1 H), 3.01 (s, 3 H), 2.05–2.20 (m, 3 H), 1.72–1.84 (m, 2 H), 1.44 (s, 9 H); LC-MS 561.1 (MH$^+$).

Step 8B:

A solution of compound 8a (158 mg, 0.28 mmol) in trifluoroacetic acid (2 mL) and dichloromethane (5 mL) was stirred for 1 hour. The reaction mixture was concentrated in vacuo to afford 160 mg of compound 8b as a colorless oil. LC-MS 461.3 (MH$^+$)

Step 8C:

A solution of pyrrolidine 8b (40 mg, 0.071 mmol), 3-phenylpropionaldehyde (0.075 mmol) and triethylamine (1.44 mmol) in methanol (1 mL) was stirred at room temperature for 3 hours. Sodium borohydride (100 mg, 2.63 mmol) was added in one portion and the reaction mixture was stirred for a further 12 hours. The reaction solution was purified directly by Preparative HPLC-MS to afford Example 8-1 as the trifluoroacetate salt (6 mg of a colorless oil). LC-MS 579.5 (MH$^+$).

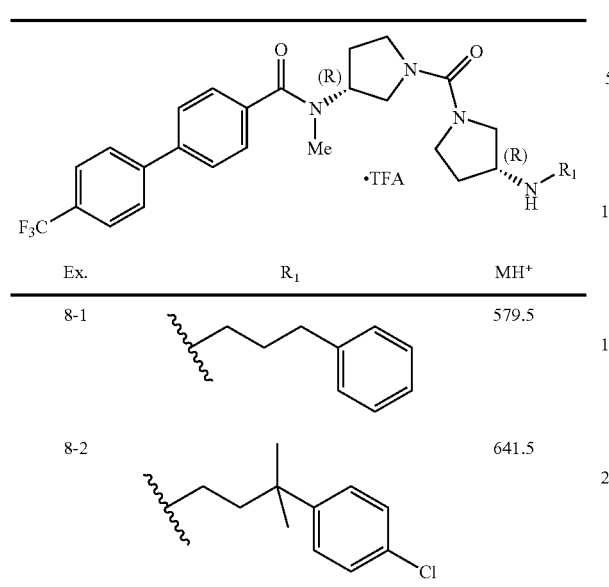

Example 9

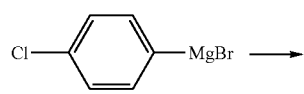

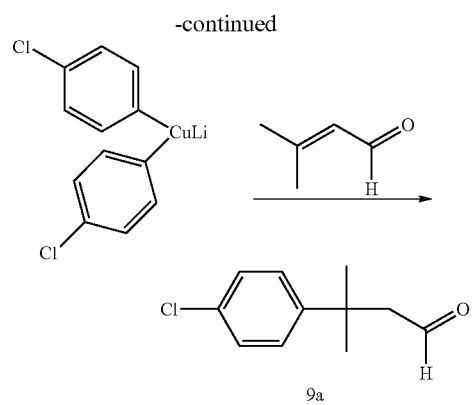

Step 9A:

Lithium thienylcyanocuprate (16 mL, 0.25M in THF, 4 mmol) was cooled to −78° C. and a solution of p-Cl-phenylmagnesium bromide (4 mL, 1 M in ether, 4 mmol) was added dropwise and the solution was stirred for 1 hr at −78° C. 3-Methyl butenal (0.38 mL, 4 mmol) was added dropwise and the mix stirred for 3 hours at −78° C. The reaction was quenched with a 5% ammonium chloride solution and the mixture was stirred 30 minutes. The layers were separated and the aqueous layer was extracted with methylene chloride. The organic layer was dried, concentrated, and the residue purified by column chromatography using 5% ethyl acetate in hexane to compound 9a (410 mg).

Example 10

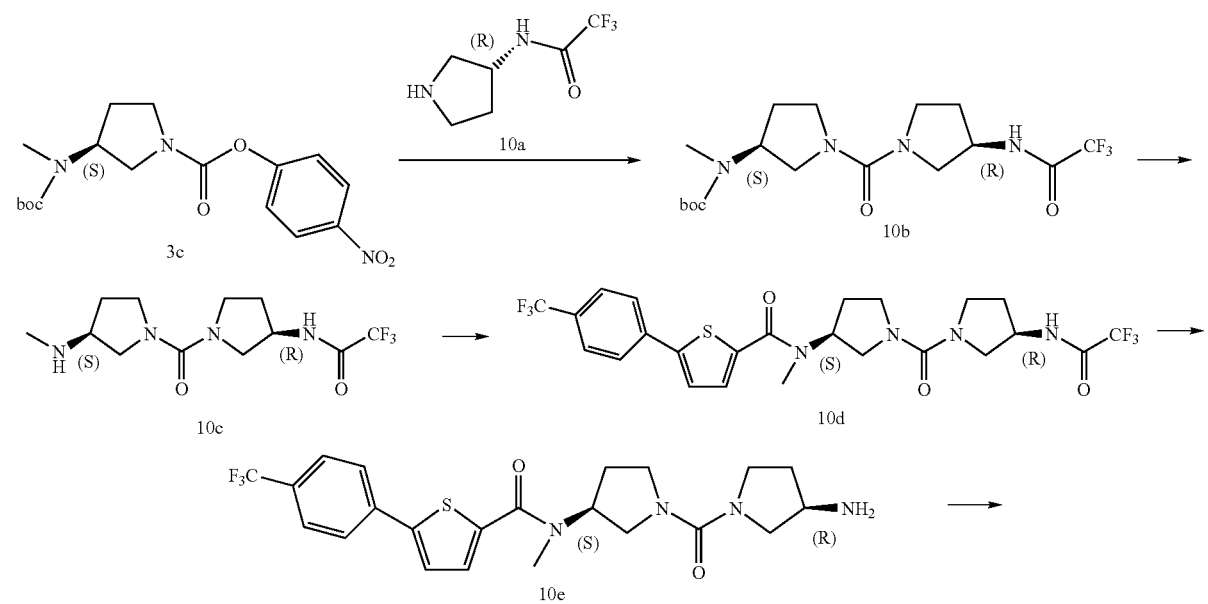

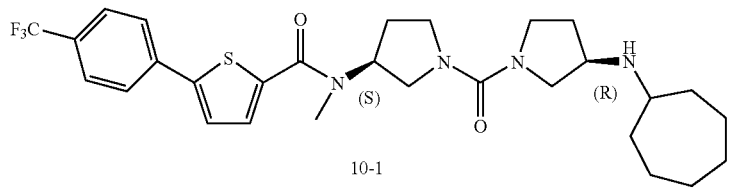

10-1

Step 10A:

To a stirred solution of (R)-3-amino-1-benzylpyrrolidine (TCI, 10.0 g, 56.8 mmol) and triethylamine (8.5 mL, 57 mmol) in dry methanol (30 mL) under nitrogen was added, dropwise over 15 min, ethyl trifluoroacetate (8.5 mL, 71 mmol). The solution was stirred overnight then concentrated. The residue was dissolved in dichloromethane (300 mL), washed with saturated aqueous sodium bicarbonate (100 mL), dried over magnesium sulfate, and concentrated in vacuo to afford the trifluoroacetate intermediate as a cream solid (15.2 g, 100%). The crude material was used directly in the next step. To a mixture of a sample of the intermediate (8.00 g, 29 mmol) and 10% palladium on activated carbon (50% water, Degussa Type E101 NE/W, Aldrich) (6.15 g, 2.9 mmol) in absolute ethanol (250 mL) was added ammonium formate (9.14 g, 145 mol). A reflux condenser open to the atmosphere was attached, and the vigorously stirring mixture was immersed in a pre-heated oil bath (95° C.), and refluxed for 1 h. The mixture was cooled, filtered over Celite, and washed with ethanol. The filtrate was evaporated, dissolved in dichloromethane, dried over magnesium sulfate and concentrated to afford 10a as a yellow, viscous oil (5.30 g, 100%). This was used directly in the next step. APCI MS m/z: 182.9 (MH$^+$).

Step 10B:

A solution of the pyrrolidine 3c (9.76 g, 26.8 mmol), (R)-(3)-(trifluoroacetamido)pyrrolidine (10a, 5.42 g, 30 mmol, available as the free base prepared in step 10A, or as the hydrochloride salt from TCI) and triethylamine (7.5 mL, 54 mmol) in dimethylformamide (100 mL) was heated and stirred in a sealed tube at 90° C. for 2.5 hours. After cooling to room temperature, the reaction mixture was diluted with ethyl acetate (150 mL) and was washed with 0.4 M aqueous sodium hydroxide (4×50 mL). The combined aqueous layers were re-extracted with ethyl acetate (2×75 mL). The combined organics were washed with brine (150 mL), dried (magnesium sulfate) and concentrated. The residue was purified by silica gel column chromatography (gradient of 30% dry acetone/hexane to 60% dry acetone/hexane) to give 10b as a pale yellow foam (7.2 g, 66%). Trituration with MTBE, followed by evaporation of the solvent, gave an amorphous powder. $^1$H-NMR (300 MHz, CDCl$_3$) δ 4.62–4.76 (m, 1H), 4.46–4.52 (m, 1H), 3.38–3.68 (m, 8H), 3.22–3.29 (m, 1H), 2.80 (s, 3H), 2.13–2.20 (m, 1H), 1.94–2.06 (m, 3H), 1.47 (s, 9H), APCI MS m/z: 409.0 (MH$^+$).

Step 10C:

Compound 10b (1.1 g) was dissolved in a mixture of 10 mL of dichloromethane and 10 mL of TFA. The resulting solution was stirred for one hour. Evaporation gave a yellow oil 10c which was used directly used in Step 10D. APCI MS m/z: 309.1 (MH$^+$).

Step 10D:

Compound 10c (0.82 g, 2.7 mmol) and 4'-trifluoromethyl-5-phenylthiophene-2-carboxylic acid (0.8 g, 2.9 mmol) were dissolved in 25 mL of dichloromethane and treated with 1-hydroxybenzotriazole hydrate (0.73 g, 5.4 mmol) and triethylamine (1.12 mL, 8.1 mmol). EDCI (0.566 g, 2.9 mmol) was added and the reaction was stirred overnight. The volatiles were evaporated and the residue was partitioned between ethyl acetate and 1N sodium hydroxide. The organic solvent was removed and the residue was purified by silica gel chromatography eluting with 5% methanol in dichloromethane to yield 1.08 g (72%) of white glassy 10d. $^1$H-NMR (300 MHz, CDCl$_3$) δ 7.80–7.17 (m, 7 H), 5.08–5.02 (m, 1 H), 4.51 (b, 1 H), 3.71–3.42 (m, 8 H), 3.18 (s, 3 H), 2.20–2.00 (m, 4 H), APCI MS m/z: 563.1 (MH$^+$).

Step 10E:

Compound 10d (1.05 g, 1.87 mmol) was dissolved in a mixture of 12.5 mL of methanol and 1.25 mL of water. Potassium carbonate (1.29 g, 9.3 mmol) was added and the resulting mixture was heated at 70° C. overnight. Evaporation removed the volatiles and the residue was washed with dichloromethane/isopropanol 3/1. Evaporation of the solvents gave 10e as a yellow oil (1.15 g, 2.47 mmol, 132%). APCI MS m/z: 467.5 (MH$^+$).

Step 10F:

To a solution of 10e (22 mg, 0.05 mmol) in 0.8 mL of methanol was added cycloheptanone (28 μL, 0.24 mmol) followed by addition of Na(OAc)$_3$BH (15 mg, 0.24 mmol), and the reaction was stirred overnight. Purification by preparative LC-MS gave 10.1 mg (37%) of Example 10-1. $^1$H-NMR (300 MHz, CDCl$_3$) δ 7.73–7.31 (m, 6 H), 5.05–5.00 (m, 1 H), 4.06–3.38 (m, 9 H), 3.16 (s, 3 H), 2.31–2.06 (m, 5 H), 1.74–1.47 (m, 12 H), APCI MS m/z: 563.4 (MH$^+$).

Using the appropriate starting materials, the following compounds were prepared according to the procedures described above.

| Ex. | R4 | NR1R2 | MW | MH+ | Rt | HPLC |
|---|---|---|---|---|---|---|
| 10-1 | 4-(trifluoromethyl)phenyl-thiophene | cycloheptyl-NH- | 462.7 | 463.4 | 6.4 | D |
| 10-2 | 3-fluoro-4'-methyl-biphenyl | cyclopropylmethyl-NH- | 478.6 | 479.4 | 4.6 | D |
| 10-3 | 3-fluoro-4'-methyl-biphenyl | tetrahydropyran-4-yl-NH- | 508.6 | 509.4 | 4.6 | D |
| 10-4 | 3-fluoro-4'-methyl-biphenyl | 4,4-dimethylcyclohexyl-NH- | 534.7 | 535.5 | 5.1 | D |
| 10-5 | 3,3'-difluoro-4'-methyl-biphenyl | N(CH3)2 | 470.6 | 471.3 | 4.4 | D |
| 10-6 | 3,3'-difluoro-4'-methyl-biphenyl | cyclopropylmethyl-NH- | 496.6 | 497.4 | 4.8 | D |
| 10-7 | 3,3'-difluoro-4'-methyl-biphenyl | tetrahydropyran-4-yl-NH- | 526.6 | 527.4 | 4.6 | D |
| 10-8 | 3,3'-difluoro-4'-methyl-biphenyl-thiophene | 4,4-dimethylcyclohexyl-NH- | 552.7 | 553.5 | 5.1 | D |
| 10-9 | 3,3'-difluoro-4'-methyl-biphenyl | sec-pentyl-NH- | 512.6 | 513.4 | 4.9 | D |

-continued
| Ex. | R₄ | NR₁R₂ | MW | MH⁺ | Rt | HPLC |
|---|---|---|---|---|---|---|
| 10-10 | 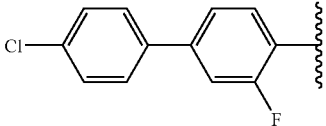 |  | 473.0 | 473.3 | 4.6 | D |
| 10-11 | 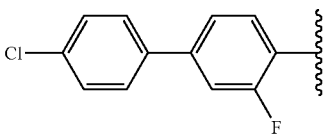 | 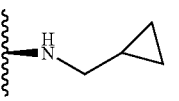 | 499.0 | 499.4 | 4.9 | D |
| 10-12 | 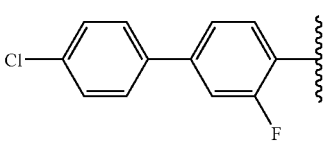 | 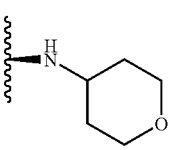 | 529.1 | 529.4 | 4.7 | D |
| 10-13 | 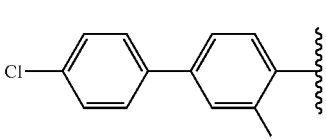 | 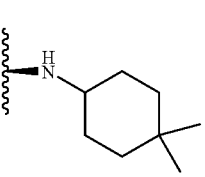 | 555.1 | 555.4 | 5.1 | D |
| 10-14 | 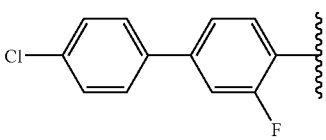 | 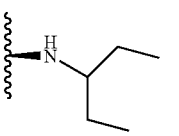 | 515.1 | 515.0 | 4.9 | D |
| 10-15 | 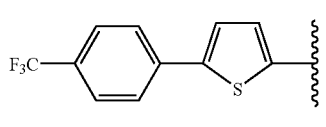 | 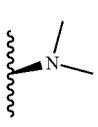 | 494.6 | 494.7 | 1.8 | G |
| 10-16 | 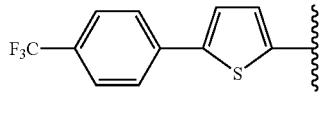 | 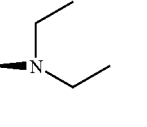 | 522.6 | 523.0 | 5.0 | D |
| 10-17 | 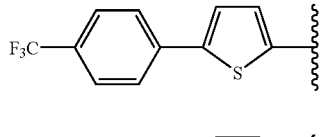 | 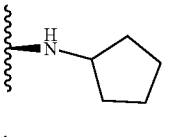 | 534.6 | 534.7 | 1.7 | G |
| 10-18 | 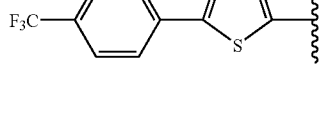 | 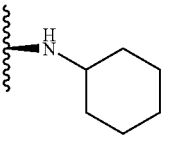 | 548.7 | 549.0 | 5.1 | D |
| 10-19 | 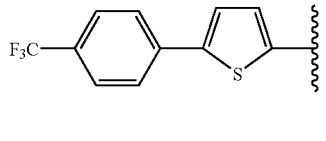 | 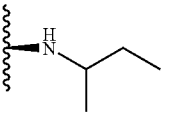 | 522.6 | 522.8 | 1.6 | G |
| 10-20 | 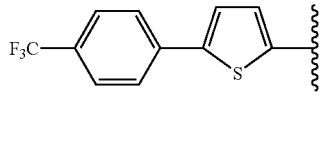 | 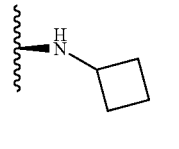 | 520.6 | 521.3 | 6.0 | D |

-continued

| Ex. | R₄ | NR₁R₂ | MW | MH⁺ | Rt | HPLC |
|---|---|---|---|---|---|---|
| 10-21 | F₃C-phenyl-thiophene | NH-CH(CH₃)-cyclobutyl | 548.7 | 549.4 | 6.4 | D |
| 10-22 | F₃C-phenyl-thiophene | NH-(2-ethylcyclohexyl) | 576.7 | 576.0 | 6.8 | D |
| 10-23 | F₃C-phenyl-thiophene | NH-(3,5-dimethylcyclohexyl) | 576.7 | 576.0 | 7.0 | D |
| 10-24 | F₃C-phenyl-thiophene | NH-CH(CH₃)-CH₂-cyclohexyl | 590.8 | 591.2 | 7.2 | D |
| 10-25 | F₃C-phenyl-thiophene | NH-(4-CF₃-cyclohexyl) | 616.7 | 617.3 | 6.8 | D |
| 10-26 | F₃C-phenyl-thiophene | NH-(1-benzylpiperidin-4-yl) | 639.8 | 640.0 | 5.0 | D |
| 10-27 | F₃C-phenyl-thiophene | NH-CH(CH₂OH)₂ | 540.6 | 541.2 | 5.3 | D |
| 10-28 | 4-methoxy-3-methylbiphenyl | NH-(tetrahydropyran-4-yl) | 520.7 | 520.8 | 1.6 | G |
| 10-29 | 4-ethylbiphenyl | NH-(tetrahydropyran-4-yl) | 504.7 | 504.0 | 1.6 | G |
| 10-30 | 4-methoxy-3-methylphenyl-thiophene | NH-cyclobutyl | 496.7 | 496.8 | 1.6 | G |

-continued

| Ex. | R₄ | NR₁R₂ | MW | MH⁺ | Rt | HPLC |
|---|---|---|---|---|---|---|
| 10-31 | 4-methoxy-2-methylbiphenyl | NH-cyclobutyl | 490.6 | 491.0 | 5.1 | D |
| 10-32 | 4-ethylbiphenyl | NH-cyclobutyl | 474.6 | 475.1 | 5.7 | D |
| 10-33 | 5-(4-ethylphenyl)thiophen-2-yl | NH-cyclobutyl | 480.7 | 481.2 | 5.6 | D |
| 10-34 | 4-methoxy-2-methylbiphenyl | NH-CH(CH₂OH)₂ | 510.6 | 511.3 | 4.5 | D |
| 10-35 | 4-ethylbiphenyl | NH-CH(CH₂OH)₂ | 494.6 | 495.2 | 5.1 | D |
| 10-36 | 5-(4-methoxy-2-methylphenyl)thiophen-2-yl | NH-CH(CH₂OH)₂ | 516.7 | 517.2 | 4.6 | D |
| 10-37 | 5-(4-ethylphenyl)thiophen-2-yl | NH-iPr | 468.7 | 469.2 | 21.2 | E |
| 10-38 | 5-(4-methoxy-2-methylphenyl)thiophen-2-yl | NH-iPr | 512.7 | 513.3 | 5.3 | D |
| 10-39 | 5-(4-methoxy-2-methylphenyl)thiophen-2-yl | NH-cyclopentyl | 510.7 | 511.2 | 5.2 | D |
| 10-40 | 5-(4-methoxy-2-methylphenyl)thiophen-2-yl | NH-cycloheptyl | 538.8 | 539.3 | 5.7 | D |
| 10-41 | 4-methoxy-2-methylbiphenyl | NH-iPr | 478.6 | 479.2 | 4.7 | D |

-continued
| Ex. | R₄ | NR₁R₂ | MW | MH⁺ | Rt | HPLC |
|---|---|---|---|---|---|---|
| 10-42 | 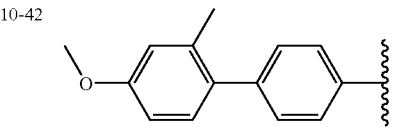 | 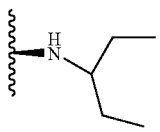 | 506.7 | 507.3 | 5.2 | D |
| 10-43 | 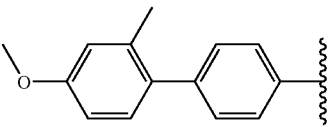 | 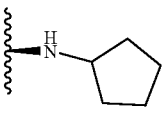 | 504.7 | 505.3 | 5.1 | D |
| 10-44 | 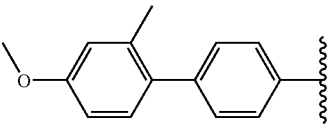 | 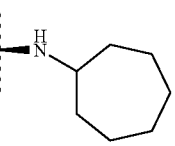 | 532.7 | 533.3 | 5.5 | D |
| 10-45 | 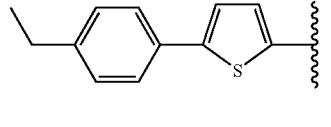 | 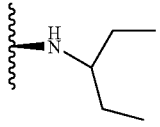 | 496.7 | 497.3 | 5.9 | D |
| 10-46 | 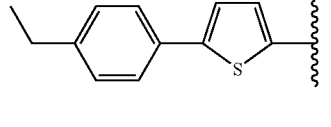 | 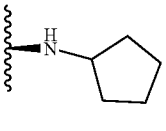 | 494.7 | 495.4 | 5.8 | D |
| 10-47 | 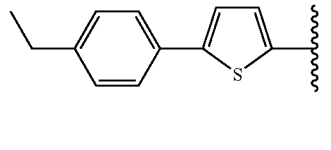 | 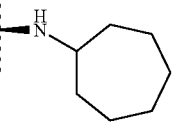 | 522.8 | 523.3 | 6.2 | D |
| 10-48 | 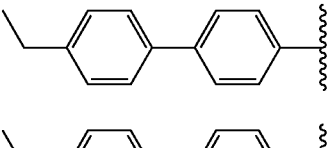 | 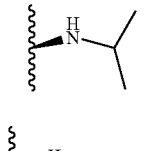 | 462.6 | 463.3 | 5.3 | D |
| 10-49 | 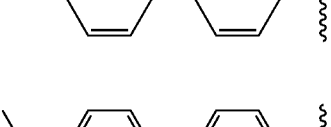 | 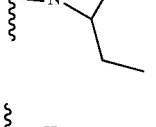 | 490.7 | 491.3 | 5.7 | D |
| 10-50 | 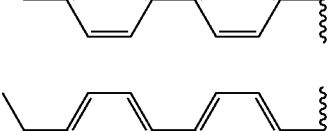 | 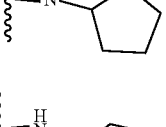 | 488.7 | 489.3 | 5.6 | D |
| 10-51 | 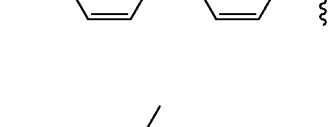 | 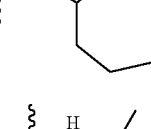 | 516.7 | 517.3 | 6.1 | D |
| 10-52 | 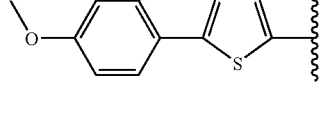 | 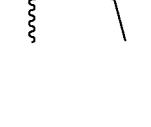 | 484.7 | 485.2 | 4.9 | D |

| Ex. | R₄ | NR₁R₂ | MW | MH⁺ | Rt | HPLC |
|---|---|---|---|---|---|---|
| 10-53 | 4-methylphenyl-thiophene | NH-isopropyl | 454.6 | 455.1 | 5.1 | D |
| 10-54 | 4-methylphenyl-thiophene | NH-cyclobutyl | 466.6 | 467.0 | 5.2 | D |
| 10-55 | 4-methylbiphenyl | NH-isopropyl | 448.6 | 449.2 | 5.0 | D |
| 10-56 | 4-methylbiphenyl | NH-cyclobutyl | 460.6 | 461.0 | 5.1 | D |
| 10-57 | 4-methylbiphenyl | NH-tetrahydropyran-4-yl | 490.6 | 491.3 | 4.9 | D |
| 10-58 | 4-trifluoromethoxy-3'-fluorobiphenyl | N(CH₃)₂ | 522.5 | 523.0 | 4.7 | D |
| 10-59 | 4-trifluoromethoxy-3'-fluorobiphenyl | NH-tetrahydropyran-4-yl | 578.6 | 579.0 | 4.8 | D |
| 10-60 | 4-trifluoromethoxy-3'-fluorobiphenyl | NH-pentan-3-yl | 564.6 | 565.0 | 4.9 | D |
| 10-61 | 4-methoxy-3'-fluorobiphenyl | NH-4,4-dimethylcyclohexyl | 550.7 | 551.1 | 4.9 | D |
| 10-62 | 4-methoxy-3'-fluorobiphenyl | NH-pentan-3-yl | 510.7 | 511.1 | 4.5 | D |
| 10-63 | 4-methoxy-3'-fluorobiphenyl | N(CH₂-cyclopropyl)₂ | 548.7 | 549.1 | 4.7 | D |

-continued

| Ex. | R₄ | NR₁R₂ | MW | MH⁺ | Rt | HPLC |
|---|---|---|---|---|---|---|
| 10-64 | 4-ethylphenyl-thiophene | NH₂ | 426.6 | 427.2 | 5.2 | D |
| 10-65 | 4-ethylbiphenyl | NH₂ | 420.6 | 421.1 | 5.0 | D |
| 10-66 | 4-methoxy-2-methylphenyl-thiophene | NH₂ | 442.6 | 443.2 | 4.6 | D |
| 10-67 | 4-methoxy-2-methylbiphenyl | NH₂ | 436.6 | 437.3 | 4.5 | D |
| 10-68 | 4-methylbiphenyl | NH-cyclopentyl | 474.65 | 475.3 | 5.2 | D |
| 10-69 | 4-methylphenyl-thiophene | NH-cyclopentyl | 480.67 | 481.2 | 5.3 | D |

$$R_4 \overset{O}{\underset{|}{C}} - N(CH_3) - \overset{(S)}{\underset{}{pyrrolidine}} - C(O) - \overset{(S)}{\underset{}{pyrrolidine}} - NR_1R_2$$

| Ex. | R₄ | NR₁R₂ | MW | MH⁺ | Rt | HPLC |
|---|---|---|---|---|---|---|
| 10-70 | 4-(CF₃)phenyl-thiophene | NH-CH₂CH₂CH(CH₃)₂ | 536.7 | 537.1 | 5.0 | D |
| 10-71 | 4-(CF₃)phenyl-thiophene | NH-CH₂-cyclohexyl | 562.7 | 563.1 | 5.6 | D |
| 10-72 | 4-(CF₃)phenyl-thiophene | NH-(tetrahydropyran-4-yl) | 550.6 | 551.0 | 5.1 | D |
| 10-73 | 4-(CF₃)phenyl-thiophene | NH-(4,4-dimethylcyclohexyl) | 576.7 | 577.1 | 5.7 | D |
| 10-74 | 4-(CF₃)phenyl-thiophene | NH-(CH₂)₃-phenyl | 584.7 | 585.1 | 5.7 | D |

-continued

| Ex. | R4 | NR1R2 | MW | MH+ | Rt | HPLC |
|---|---|---|---|---|---|---|
| 10-75 | F3C-phenyl-thiophene | cyclopentyl-NH | 534.6 | 534.7 | 1.8 | G |
| 10-76 | F3C-phenyl-thiophene | NH-CH2CH2CH2-cyclopentyl | 576.7 | 576.7 | 1.7 | G |

Example 11

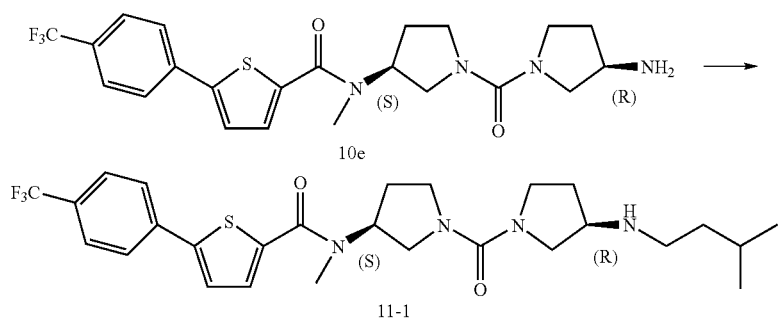

Step 11A:

To a solution of 10e (22 mg, 0.05 mmol) in 0.8 mL of methanol was added isovaleraldehyde (5.3 µL, 0.05 mmol) followed by BH3-Pyridine (8M, 12 µL, 0.10 mmol). The mixture was stirred for one hour, then purified by preparative LC-MS to give 9.8 mg (38%) of Example 11-1. ¹H-NMR (300 MHz, CDCl3) δ 7.73–7.32 (m, 6 H), 5.04–4.99 (m, 1 H), 3.76–3.342 (m, 9 H), 3.16 (s, 3 H), 3.02–2.93 (m, 2H), 2.29–2.10 (m, 4 H), 1.69–1.55 (m, 7 H), APCI MS m/z: 537.1 (MH⁺).

Using the appropriate starting materials, the following compounds were prepared according to the procedures described above.

| Ex. | R4 | NR1R2 | MW | MH+ | Rt | HPLC |
|---|---|---|---|---|---|---|
| 11-1 | F3C-phenyl-thiophene | NH-CH2CH2CH(CH3)2 | 536.66 | 537.1 | 6.4 | D |
| 11-2 | F3C-phenyl-thiophene | NH-CH2-cyclopropyl | 520.62 | 520.7 | 1.7 | G |

-continued
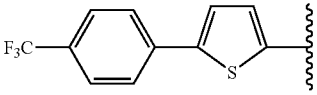
| Ex. | R₄ | NR₁R₂ | MW | MH⁺ | Rt | HPLC |
|---|---|---|---|---|---|---|
| 11-3 | 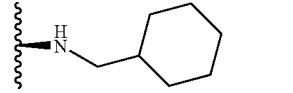 | 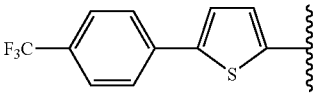 | 562.70 | 563.2 | 6.6 | D |
| 11-4 | 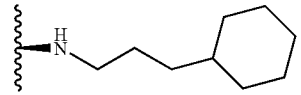 | 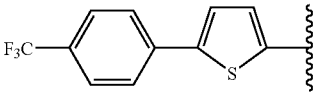 | 590.75 | 591.2 | 7.4 | D |
| 11-5 | 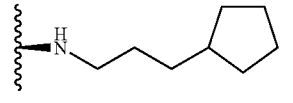 | 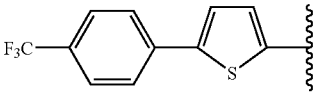 | 576.72 | 576.7 | 1.6 | G |
| 11-6 | 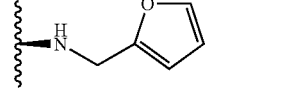 | 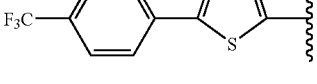 | 546.61 | 547.0 | 5.2 | D |
| 11-7 | 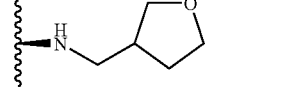 | 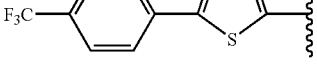 | 550.64 | 551.2 | 5.1 | D |
| 11-8 | 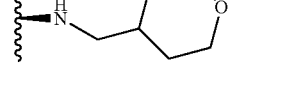 | 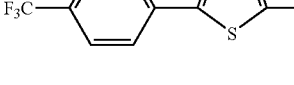 | 564.67 | 565.2 | 5.1 | D |
| 11-9 | 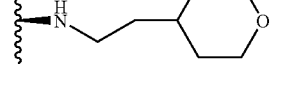 | 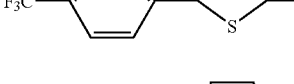 | 578.70 | 579.0 | 5.2 | D |
| 11-10 | 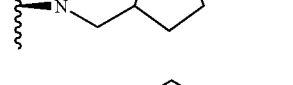 | 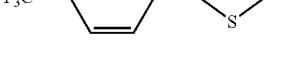 | 564.67 | 565.2 | 5.4 | D |
| 11-11 | 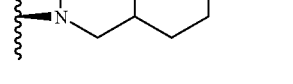 | 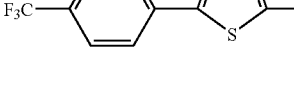 | 578.70 | 579.2 | 5.4 | D |
| 11-12 | 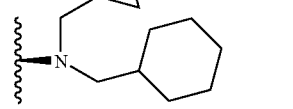 | 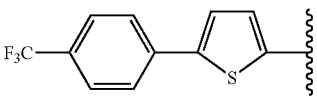 | 618.76 | 619.0 | 5.0 | D |
| 11-13 |  | | 606.75 | 607.0 | 5.1 | D |

-continued
| Ex. | R₄ | NR₁R₂ | MW | MH⁺ | Rt | HPLC |
|---|---|---|---|---|---|---|
| 11-14 | 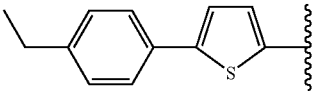 |  | 454.64 | 454.8 | 1.8 | G |
| 11-15 | 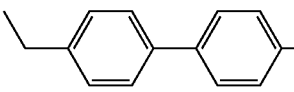 | 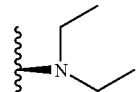 | 476.66 | 476.9 | 1.6 | G |
| 11-16 | 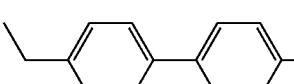 | 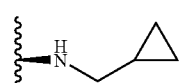 | 474.65 | 475.0 | 5.3 | D |
| 11-17 | 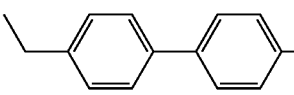 | 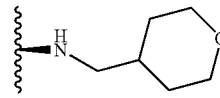 | 518.70 | 518.8 | 1.6 | G |
| 11-18 | 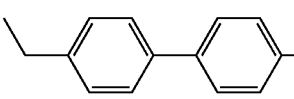 | 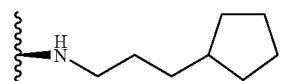 | 530.75 | 531.3 | 6.1 | D |
| 11-19 | 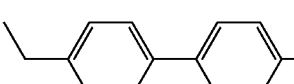 | 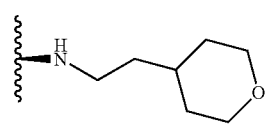 | 532.72 | 532.8 | 1.6 | G |
| 11-20 | 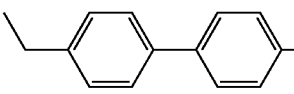 | 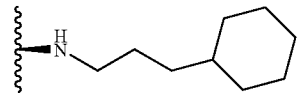 | 544.78 | 545.4 | 6.3 | D |
| 11-21 | 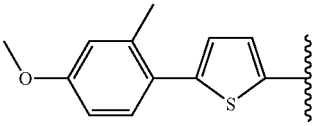 |  | 470.63 | 471.0 | 4.8 | D |
| 11-22 | 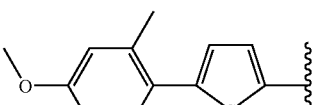 |  | 498.69 | 498.8 | 1.6 | G |
| 11-23 | 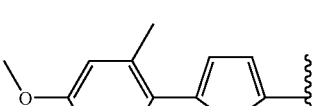 | 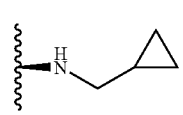 | 496.67 | 497.0 | 5.1 | D |
| 11-24 | 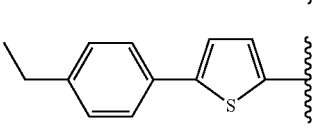 | 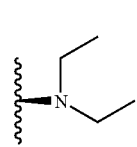 | 482.69 | 482.8 | 1.6 | G |

-continued

| Ex. | R₄ | NR₁R₂ | MW | MH⁺ | Rt | HPLC |
|---|---|---|---|---|---|---|
| 11-25 | methoxy-methylphenyl-thiophene | NH-CH₂-tetrahydropyran | 540.72 | 540.8 | 1.6 | G |
| 11-26 | methoxy-methylphenyl-thiophene | NH-(CH₂)₃-cyclopentyl | 552.78 | 553.3 | 5.8 | D |
| 11-27 | methoxy-methylphenyl-thiophene | NH-CH₂CH₂-tetrahydropyran | 554.75 | 554.8 | 1.6 | G |
| 11-28 | methoxy-methylphenyl-thiophene | NH-(CH₂)₃-cyclohexyl | 566.81 | 567.0 | 6.0 | D |
| 11-29 | methoxy-methylbiphenyl | N(Et)₂ | 492.66 | 493.1 | 4.8 | D |
| 11-30 | methoxy-methylbiphenyl | NH-CH₂-cyclopropyl | 490.64 | 490.8 | 1.5 | G |
| 11-31 | methoxy-methylbiphenyl | NH-CH₂-tetrahydropyran | 534.70 | 534.8 | 1.6 | G |
| 11-32 | ethylphenyl-thiophene | NH-CH₂-cyclopropyl | 480.67 | 481.0 | 1.6 | G |
| 11-33 | methoxy-methylbiphenyl | NH-CH₂CH₂-tetrahydropyran | 548.72 | 548.8 | 1.6 | G |
| 11-34 | methoxy-methylbiphenyl | NH-(CH₂)₃-cyclohexyl | 560.78 | 561.1 | 6.2 | D |

-continued

| Ex. | R₄ | NR₁R₂ | MW | MH⁺ | Rt | HPLC |
|---|---|---|---|---|---|---|
| 11-35 | 4-ethylphenyl-thiophene | -NH-CH₂-(tetrahydropyran-4-yl) | 524.73 | 524.8 | 1.7 | G |
| 11-36 | 4-ethylphenyl-thiophene | -NH-(CH₂)₃-cyclopentyl | 536.78 | 537.1 | 6.1 | D |
| 11-37 | 4-ethylphenyl-thiophene | -NH-CH₂CH₂-(tetrahydropyran-4-yl) | 538.75 | 538.8 | 1.6 | G |
| 11-38 | 4-ethylphenyl-thiophene | -NH-(CH₂)₃-cyclohexyl | 550.81 | 551.1 | 6.5 | D |
| 11-39 | 4-ethylbiphenyl | -N(CH₃)₂ | 448.61 | 448.9 | 1.7 | G |
| 11-40 | 4-methoxy-2-methylbiphenyl | -N(CH₃)₂ | 464.61 | 465.2 | 4.6 | D |
| 11-41 | 4-ethylbiphenyl | -N[(CH₂)₃-cyclopentyl]₂ | 640.95 | 641.5 | 8.2 | D |
| 11-42 | 4-methoxy-2-methylphenyl-thiophene | -N[(CH₂)₃-cyclopentyl]₂ | 662.98 | 663.4 | 7.9 | D |
| 11-43 | 4-ethylphenyl-thiophene | -N[(CH₂)₃-cyclopentyl]₂ | 646.98 | 647.4 | 8.3 | D |
| 11-44 | 4-methylphenyl-thiophene | -N(CH₃)₂ | 440.61 | 441.0 | 5.0 | D |

-continued

| Ex. | R₄ | NR₁R₂ | MW | MH⁺ | Rt | HPLC |
|---|---|---|---|---|---|---|
| 11-45 | 4-methylphenyl-thiophene | N(CH₂-cyclopropyl)₂ | 520.74 | 521.0 | 5.6 | D |
| 11-46 | 4-methylphenyl-thiophene | NH-CH₂-tetrahydropyran | 510.70 | 511.0 | 5.1 | D |
| 11-47 | 4-methylbiphenyl | N(CH₃)₂ | 434.58 | 435.1 | 4.8 | D |
| 11-48 | 4-methylbiphenyl | NH-CH₂-tetrahydropyran | 504.67 | 505.2 | 5.0 | D |
| 11-49 | 4-methylphenyl-thiophene | NH-CH₂-cyclopropyl | 466.65 | 467.3 | 5.2 | D |
| 11-50 | 4-methylbiphenyl | NH-CH₂-cyclopropyl | 460.62 | 461.0 | 5.1 | D |
| 11-51 | 4-methylbiphenyl | N(CH₂-cyclopropyl)₂ | 514.71 | 515.1 | 5.6 | D |
| 11-52 | 4-methoxy-2-methylphenyl-thiophene | N(CH₃)-tetrahydropyran | 540.72 | 541.3 | 5.6 | F |
| 11-53 | 4-methylbiphenyl | NH-isobutyl | 462.63 | 463.3 | 5.2 | D |

Example 12

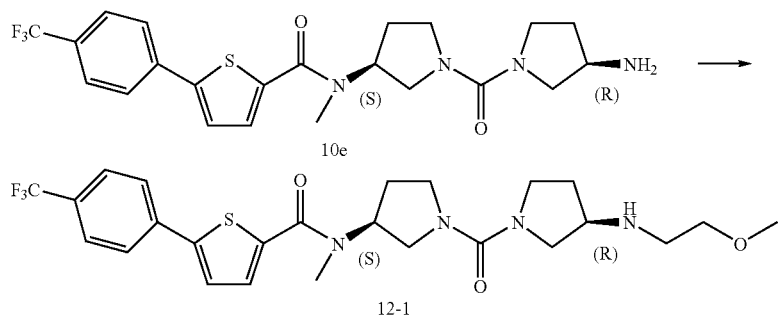

Step 12A:

To a solution of 10d (18 mg, 0.04 mmol) in 0.8 mL of DMF were added 2-methoxyethylbromide (4 μL, 0.04 mmol), 4-methyl-morpholine (17 μL, 0.15 mmol) and sodium iodide (17 mg, 0.12 mmol). The reaction was heated at 80° C. overnight, then purified by preparative LC-MS to give 5.7 mg (28%) of Example 12-1. APCI MS m/z: 525.2 (MH$^+$).

Using the appropriate starting materials, the following compounds were prepared according to the procedures described above. In place of 4-methyl-morpholine, other base such as potassium carbonate or sodium hydride has also been used. When $R_1$ is 2-ethylsulfonylethyl and $R_2$ is methyl, no base is needed.

| Ex. | R$_4$ | NR$_1$R$_2$ | MW | MH$^+$ | Rt | HPLC |
|---|---|---|---|---|---|---|
| 12-1 | F$_3$C-phenyl-thiophene | HN-CH$_2$CH$_2$-OCH$_3$ | 524.61 | 535.2 | 5.5 | D |
| 12-2 | F$_3$C-phenyl-thiophene | HN-(CH$_2$)$_4$-C(O)OEt | 594.69 | 594.7 | 1.6 | G |
| 12-3 | F$_3$C-phenyl-thiophene | HN-CH$_2$CH$_2$-OH | 510.58 | 510.7 | 1.7 | G |
| 12-4 | F$_3$C-phenyl-thiophene | HN-CH$_2$CH$_2$CH$_2$-OCH$_3$ | 538.63 | 539.2 | 5.6 | D |
| 12-5 | F$_3$C-phenyl-thiophene | HN-CH$_2$CH$_2$-S(O)$_2$-Ph | 634.74 | 635.0 | 5.3 | D |

-continued

| Ex. | R₄ | NR₁R₂ | MW | MH⁺ | Rt | HPLC |
|---|---|---|---|---|---|---|
| 12-6 | 4-(trifluoromethyl)phenyl-thiophene | -NH-CH₂CH₂-SO₂-CH₂CH₃ | 586.70 | 587.2 | 5.6 | D |
| 12-7 | 4-ethylphenyl-thiophene | -NH-CH₂CH₂-OCH₃ | 484.66 | 485.2 | 5.4 | D |
| 12-8 | 4-methoxy-2-methylphenyl-thiophene | -NH-CH₂CH₂CH₂-OCH₃ | 514.69 | 515.0 | 5.3 | D |
| 12-9 | 4'-methoxy-2'-methylbiphenyl | -NH-CH₂CH₂-OCH₃ | 494.63 | 495.1 | 5.0 | D |
| 12-10 | 4'-methoxy-2'-methylbiphenyl | -NH-CH₂CH₂CH₂-OCH₃ | 508.66 | 509.1 | 5.0 | D |
| 12-11 | 4-ethylphenyl-thiophene | -NH-CH₂CH₂CH₂-OCH₃ | 498.69 | 499.0 | 5.8 | D |
| 12-12 | 4'-ethyl-2'-methylbiphenyl | -NH-CH₂CH₂-OCH₃ | 478.63 | 479.1 | 5.6 | D |
| 12-13 | 4'-ethyl-2'-methylbiphenyl | -NH-CH₂CH₂CH₂-OCH₃ | 492.66 | 493.1 | 5.7 | D |
| 12-14 | 4-methoxy-2-methylphenyl-thiophene | -NH-CH₂CH₂-OCH₃ | 500.66 | 501.0 | 5.2 | D |
| 12-15 | 4-methoxy-2-methylphenyl-thiophene | -NH-CH₂CH₂-(1,3-dioxolan-2-yl) | 542.70 | 543.2 | 5.0 | D |

-continued

| Ex. | R₄ | NR₁R₂ | MW | MH⁺ | Rt | HPLC |
|---|---|---|---|---|---|---|
| 12-16 | 4-methoxy-2-methylphenyl-thiophene | NH-CH₂CH₂-(1,3-dioxane) | 556.72 | 557.3 | 5.1 | D |
| 12-17 | 4-methoxy-2-methylbiphenyl | NH-CH₂CH₂-(1,3-dioxolane) | 536.67 | 537.3 | 4.8 | D |
| 12-18 | 4-methoxy-2-methylbiphenyl | NH-CH₂CH₂-(1,3-dioxane) | 550.70 | 551.3 | 4.9 | D |
| 12-19 | 4-methylphenyl-thiophene | NH-CH₂CH₂-(1,3-dioxolane) | 526.70 | 527.2 | 5.5 | D |
| 12-20 | 4-methylphenyl-thiophene | NH-CH₂CH₂-(1,3-dioxane) | 540.72 | 541.3 | 5.6 | D |
| 12-21 | 4-ethyl-2-methylbiphenyl | NH-CH₂CH₂-(1,3-dioxolane) | 520.67 | 521.1 | 5.4 | D |
| 12-22 | 4-ethyl-2-methylbiphenyl | NH-CH₂CH₂-(1,3-dioxane) | 534.70 | 535.3 | 5.5 | D |
| 12-23 | 4-methylphenyl-thiophene | NH-CH₂CH₂CH₂-OCH₃ | 484.66 | 485.0 | 5.1 | D |
| 12-24 | 4-methylbiphenyl | NH-CH₂CH₂CH₂-OCH₃ | 478.63 | 479.0 | 5.0 | D |
| 12-25 | 4-methoxy-2-methylphenyl-thiophene | N(CH₂-cyclopropyl)(tetrahydropyran-4-yl) | 580.79 | 581.3 | 6.0 | F |

-continued

| Ex. | R₄ | NR₁R₂ | MW | MH⁺ | Rt | HPLC |
|---|---|---|---|---|---|---|
| 12-26 | 4-methoxy-2-methylphenyl-thiophene | N(methallyl)(tetrahydropyran-4-yl) | 580.79 | 581.3 | 6.1 | F |
| 12-27 | 4-methoxy-2-methylphenyl-thiophene | N(SO₂Me)(tetrahydropyran-4-yl) | 604.79 | 605.2 | 7.3 | F |
| 12-28 | 4-methoxy-2-methylbiphenyl | NH-CH₂CH₂-OMe | 508.66 | 509.1 | 4.8 | D |
| 12-29 | 4-methoxy-2-methylbiphenyl | NH-CH₂CH₂CH₂-OMe | 522.69 | 523.1 | 4.8 | D |
| 12-30 | 4-methoxy-2-methylbiphenyl | N(Me)-CH₂CH₂-(1,3-dioxan-2-yl) | 564.72 | 565.0 | 4.9 | D |
| 12-31 | 4-methoxy-2-methylbiphenyl | N(Me)-CH₂CH₂-(1,3-dioxolan-2-yl) | 550.70 | 550.8 | 1.6 | G |
| 12-32 | 4-methoxy-2-methylphenyl-thiophene | NH-CH₂CH₂-OMe | 514.69 | 514.8 | 1.6 | G |
| 12-33 | 4-methoxy-2-methylphenyl-thiophene | NH-CH₂CH₂CH₂-OMe | 528.71 | 528.8 | 1.6 | G |
| 12-34 | 4-methoxy-2-methylphenyl-thiophene | N(Me)-CH₂CH₂-(1,3-dioxolan-2-yl) | 556.72 | 556.8 | 1.6 | G |

-continued

| Ex. | R4 | NR1R2 | MW | MH+ | Rt | HPLC |
|---|---|---|---|---|---|---|
| 12-35 | 4-methoxy-2-methylphenyl-thiophene | N-methyl-2-(1,3-dioxan-2-yl)ethyl | 570.75 | 570.8 | 1.6 | G |
| 12-36 | 4-methylphenyl-thiophene | NH-CH2CH2-OMe | 498.69 | 498.8 | 1.6 | G |
| 12-37 | 4-methylphenyl-thiophene | NH-CH2CH2CH2-OMe | 512.71 | 512.8 | 1.6 | G |
| 12-38 | 4-methylphenyl-thiophene | N-methyl-(1,3-dioxolan-2-yl)methyl | 540.72 | 540.8 | 1.6 | G |
| 12-39 | 4-methylphenyl-thiophene | N-methyl-2-(1,3-dioxan-2-yl)ethyl | 554.75 | 554.8 | 1.6 | G |
| 12-40 | 4-ethyl-2-methylbiphenyl | NH-CH2CH2-OMe | 492.66 | 493.0 | 4.8 | D |
| 12-41 | 4-ethyl-2-methylbiphenyl | NH-CH2CH2CH2-OMe | 506.69 | 507.1 | 4.9 | D |
| 12-42 | 4-ethyl-2-methylbiphenyl | N-methyl-(1,3-dioxolan-2-yl)methyl | 534.70 | 535.0 | 4.9 | D |
| 12-43 | 4-ethyl-2-methylbiphenyl | N-methyl-2-(1,3-dioxan-2-yl)ethyl | 548.72 | 549.1 | 4.8 | D |
| 12-44 | 4-methoxy-2-methylphenyl-thiophene | N-ethyl-(tetrahydropyran-4-yl) | 554.75 | 555.3 | 5.8 | F |

-continued

| Ex. | R₄ | NR₁R₂ | MW | MH⁺ | Rt | HPLC |
|---|---|---|---|---|---|---|
| 12-45 | 4-methoxy-2-methylphenyl-thiophene | N(allyl)(tetrahydropyran-4-yl) | 566.76 | 567.3 | 5.8 | F |
| 12-46 | 4-methoxy-2-methylphenyl-thiophene | N(2-hydroxyethyl)(tetrahydropyran-4-yl) | 570.75 | 571.3 | 5.5 | F |
| 12-47 | 4-ethyl-2-methylbiphenyl | N(Me)(CH₂CH₂SO₂Et) | 554.75 | 555.0 | 4.9 | D |
| 12-48 | 4-methoxy-2-methylbiphenyl | N(Me)(CH₂CH₂SO₂Et) | 570.75 | 571.0 | 4.7 | D |
| 12-49 | 4-methylphenyl-thiophene | N(Me)(CH₂CH₂SO₂Et) | 580.78 | 561.0 | 4.9 | D |
| 12-50 | 4-methoxy-2-methylphenyl-thiophene | N(Me)(CH₂CH₂SO₂Et) | 576.78 | 577.0 | 4.7 | D |
| 12-51 | 4-(trifluoromethyl)phenyl-thiophene | NH(CH₂CH₂-1,3-dioxolan-2-yl) | 566.64 | 566.9 | 5.2 | D |
| 12-52 | 4-(trifluoromethyl)phenyl-thiophene | NH(CH₂CH₂-1,3-dioxan-2-yl) | 580.67 | 581.0 | 5.2 | D |

Example 13

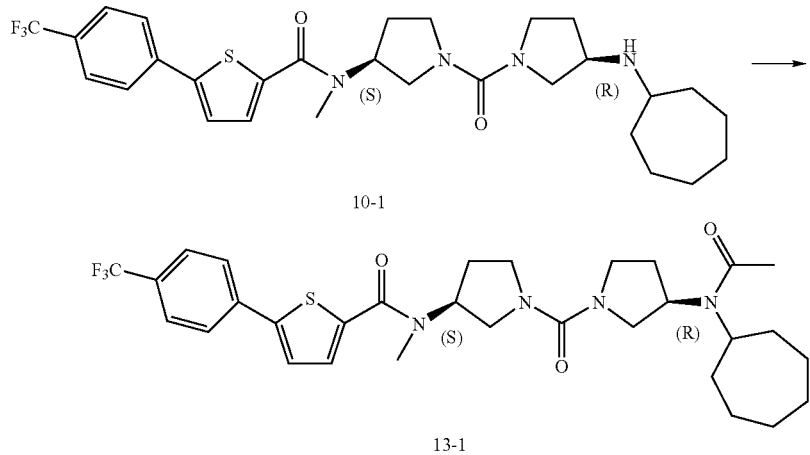

Step 13A:

To a solution of 10-1 (18 mg) in 0.8 mL of DMA was added acetyl chloride and catalytic amount of DMAP. The reaction mixture was heated overnight at 80° C. and was purified by preparative LC-MS to give 11.0 mg (64%) of example 13-1. APCI MS m/z: 605.2 (MH⁺).

Using the appropriate starting materials, the following compounds were prepared according to the procedures described above.

| Ex. | R₄ | NR₁R₂ | MW | MH⁺ | Rt | HPLC |
|---|---|---|---|---|---|---|
| 13-1 | F₃C-phenyl-thiophene | acetyl-cycloheptyl-N | 604.7 | 605.0 | 8.5 | D |
| 13-2 | F₃C-phenyl-thiophene | acetyl-isobutyl-N | 578.7 | 579.2 | 7.9 | D |
| 13-3 | F₃C-phenyl-thiophene | ethoxycarbonyl-(tetrahydropyran-4-ylmethyl)-N | 636.7 | 637.3 | 7.8 | D |
| 13-4 | F₃C-phenyl-thiophene | methylsulfonyl-(tetrahydropyran-4-ylmethyl)-N | 642.8 | 643.2 | 7.3 | D |

-continued
| Ex. | R₄ | NR₁R₂ | MW | MH⁺ | Rt | HPLC |
|---|---|---|---|---|---|---|
| 13-5 | methoxy-methylphenyl-thiophene | acetyl-tetrahydropyran-amine | 568.7 | 568.7 | 1.5 | G |
| 13-6 | methoxy-methylphenyl-thiophene | ethoxycarbonyl-tetrahydropyran-amine | 598.8 | 598.7 | 1.5 | G |
Example 14
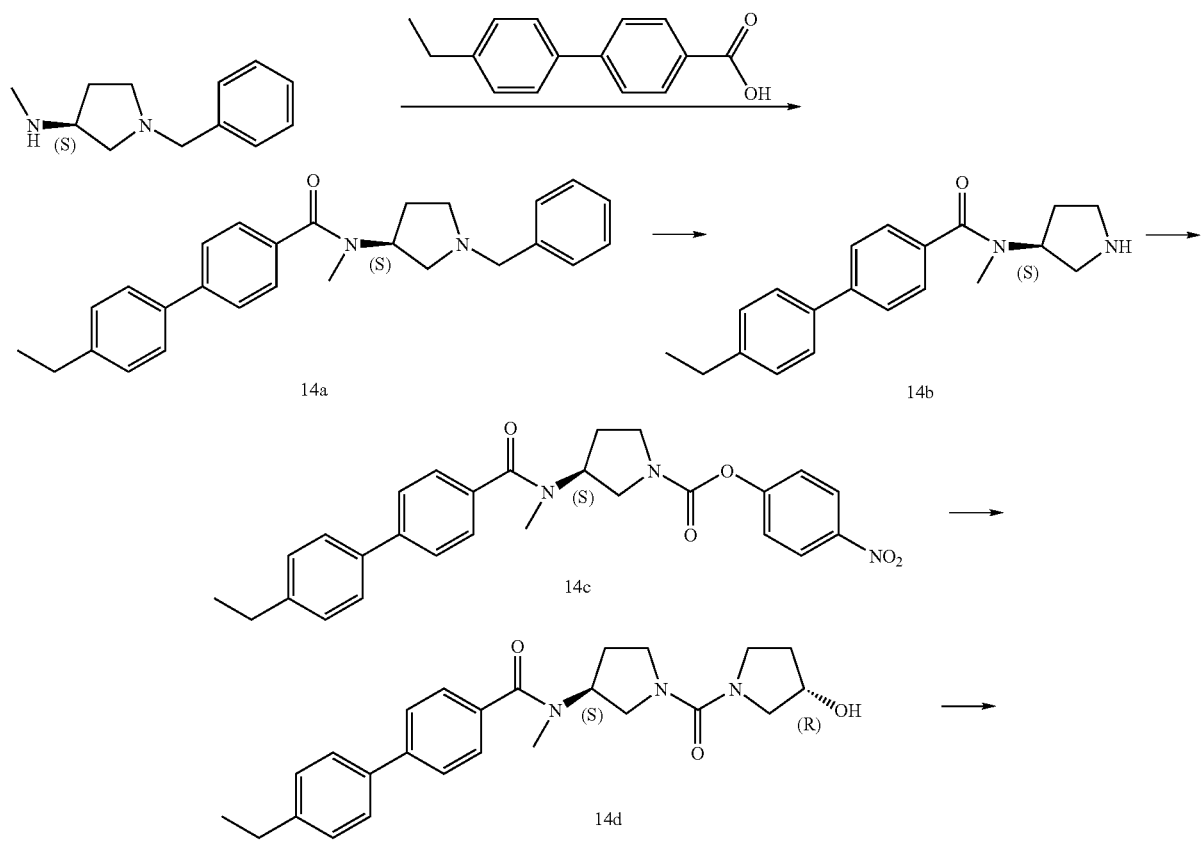

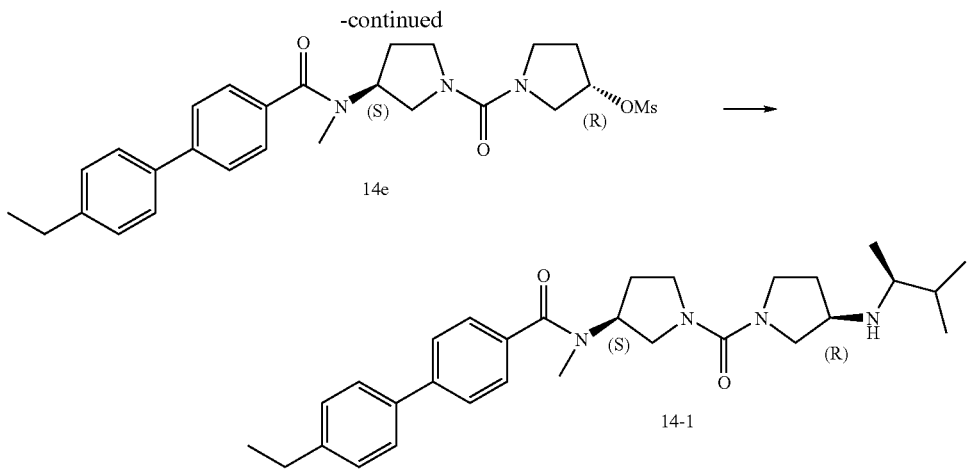

Step 14A:

(S)-3-Amino-1-benzylpyrrolidine (1.0 g, 5.25 mmol) was dissolved in DMF (25 mL) and then 4-(4-ethylphenyl)benzoic acid (1.42 g, 6.3 mmol), HOBT (0.85 g, 6.3 mmol), diisopropylethylamine (1.69 g, 13.1 mmol) and HBTU (2.4 g, 6.3 mmol) were added in that order. The solution was stirred at room temperature overnight. After removing the volatiles, the crude reaction mixture was filtered through a pad of silica gel using 9:1 ethyl acetate/ethanol as eluent. Compound 14a was obtained as an amber oil (4.4 g). APCI MS m/z: 399.2 (MH$^+$).

Step 14B:

The sample of 14a was dissolved in ethanol (25 mL) and placed in a 100° C. bath. The solution was brought to reflux and treated with ammonium formate (1.99 g, 31.5 mmol) and palladium on carbon (60% weight, 277 mg, 0.26 mmol). After 2 hours of vigorous reflux, the reaction mixture was allowed to cool to room temperature and filtered through a pad of Celite, washing with ethanol (150 mL). After evaporation of volatiles, crude 14b was obtained as a thick golden oil (3.5 g), which was used without further manipulation. APCI MS m/z: 309.2 (MH$^+$).

Step 14C:

The amine 14b was dissolved in anhydrous THF (25 mL) and cooled in an ice bath. The p-nitrophenyl chloroformate (1.16 g, 5.77 mmol) was added carefully in portions. The cold bath was then removed and the reaction allowed to proceed at room temperature overnight. An additional equivalent of p-nitrophenyl chloroformate and 3 equivalents of triethylamine were then added. After half an hour, the reaction mixture was partitioned between saturated bicarbonate solution and dichloromethane (1:1, 50 mL). The organic layer was separated and washed with a solution of 0.5N sodium hydroxide (25 mL). After drying and evaporation, the residue was coevaporated with ethyl acetate to give 14c as a light yellow powder (3.58 g). APCI MS m/z: 474.2 (MH$^+$).

Step 14D:

The carbamate 14c (1.79 g, 3.8 mmol) was suspended in anhydrous DMF (15 mL) and treated first with triethylamine (2.1 mL, 15.1 mmol) and then S-3-hydroxypyrrolidine hydrochloride (0.56 g, 4.54 mmol). The mixture was placed in an 80° C. oil bath and heated for 4 hours. After cooling, the solvent was evaporated under reduced pressure and the residue partitioned between dichloromethane (50 mL) and a solution of 0.5 N sodium hydroxide. The organic layer was washed with additional 0.5 N sodium hydroxide (2×30 mL) and dried over magnesium sulfate. Evaporation and silica gel chromatography with 4–8% methanol in dichloromethane resulted in 14d as an off-white solid (420 mg, 32% yield over 4 steps). $^1$H NMR (300 MHz, CDCl$_3$) δ 7.62 (d, J=8.1 Hz, 2H), 7.53 (d, J=8.1 Hz, 2H), 7.45 (d, J=8.1 Hz, 2H), 7.30 (d, J=8.1 Hz, 2H), 4.44–4.46 (m, 1H), 3.40–3.69 (m, 8H), 3.00 (s, 3H), 2.71 (q, J=7.5 Hz, 2H), 1.88–2.11 (m, 5H), 1.28 (t, J=7.5 Hz, 3H). APCI MS m/z: 422.2 (MH$^+$).

Step 14E:

A solution of alcohol 14d (211 mg, 0.50 mmol) in anhydrous dichloromethane (2.5 mL) was treated with triethylamine (0.14 mL, 1.0 mmol) and cooled to −40° C. under an atmosphere of nitrogen. Methanesulfonyl chloride (0.04 mL, 0.55 mmol) was added and the mixture was maintained at this low temperature. After 1 hour, saturated sodium bicarbonate solution (5 mL) was added and the mixture was allowed to warm to room temperature. The organic layer was separated and the aqueous layer was extracted with dichloromethane (2×5 mL). The combined organic layers were dried and evaporated to give the desired mesylate 14e as an off-white foam (223 mg, 89% yield). $^1$H NMR (300 MHz, CDCl$_3$) δ 7.63 (d, J=8.1 Hz, 2H), 7.53 (d, J=8.1 Hz, 2H), 7.46 (d, J=8.1 Hz, 2H), 7.30 (d, J=8.1 Hz, 2H), 5.24–5.27 (m, 1H), 3.38–3.78 (m, 8H), 3.06 (s, 3H), 3.01 (s, 3H), 2.71 (q, J=7.5 Hz, 2H), 2.09–2.32 (m, 4H), 1.28 (t, J=7.5 Hz, 3H). APCI MS m/z: 500.0 (MH$^+$).

Step 14F:

A solution of 14e (22 mg, 0.04 mmol) in N,N-dimethylacetamide (0.5 mL) was treated with 100 μL of (S)-2,3-dimethylbutylamine and the reaction vessel heated at 60° C. overnight and at 90° C. for another 6 hrs. The reaction mixture was then diluted to 1.0 mL with methanol and purified by preparative HPLC/MS to yield 12 mg (50%) of Example 14-1. $^1$H NMR (300 MHz, CDCl$_3$) δ 7.62 (d, J=8.1 Hz, 2H), 7.52 (d, J=8.4 Hz, 2H), 7.45 (d, J=8.1 Hz, 2H), 7.29 (d, J=7.5 Hz, 2H), 5.17 (br s, 1H), 3.64–3.81 (m, 6H), 3.38–3.47 (m, 3H), 3.11 (m, 1H), 2.99 (s, 3H), 2.71 (q, J=7.5 Hz, 2H), 2.31 (m, 2H), 2.12–2.14 (m, 3H), 1.28 (t, J=7.5 Hz, 3H), 1.27 (d, J=5.7 Hz, 3H), 1.0 (d, J=7.2 Hz, 3H), 0.96 (d, J=6.9 Hz, 3H). APCI MS m/z: 491.3 (MH$^+$).

Using the appropriate starting materials, the following compounds were prepared according to the procedures described above.
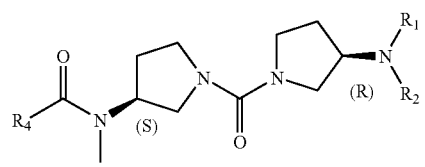
| Ex. | R₄ | NR₁R₂ | MW | MH⁺ | Rt | HPLC |
|---|---|---|---|---|---|---|
| 14-1 | | | 490.69 | 491.3 | 22.4 | E |
| 14-2 | | | 461.05 | 461.2 | 5.2 | D |
| 14-3 | | | 476.66 | 477.1 | 5.6 | D |
| 14-4 | | | 491.68 | 492.1 | 4.6 | D |
| 14-5 | | | 492.7 | 493.3 | 5.3 | D |
| 14-6 | | | 488.7 | 489.3 | 5.3 | D |
| 14-7 | | | 564.8 | 565.3 | 6.4 | D |
| 14-8 | | | 490.7 | 491.3 | 5.7 | D |
| 14-9 | | | 490.7 | 491.3 | 5.1 | D |

-continued
| Ex. | R₄ | NR₁R₂ | MW | MH⁺ | Rt | HPLC |
|---|---|---|---|---|---|---|
| 14-10 | 2-methyl-4-ethylbiphenyl | NH-CH₂CH₂-O-iPr | 506.7 | 507.3 | 5.7 | D |
| 14-11 | 2-methyl-4-ethylbiphenyl | NH-CH₂-(tetrahydrofuran-2-yl) | 504.7 | 505.3 | 5.4 | D |
| 14-12 | 2-methyl-4-ethylbiphenyl | NH-CH₂-(tetrahydrofuran-2-yl) | 504.7 | 505.3 | 5.4 | D |
| 14-13 | 4-ethylbiphenyl | pyrrolidin-1-yl | 474.65 | 475.0 | 1.6 | D |
Example 15
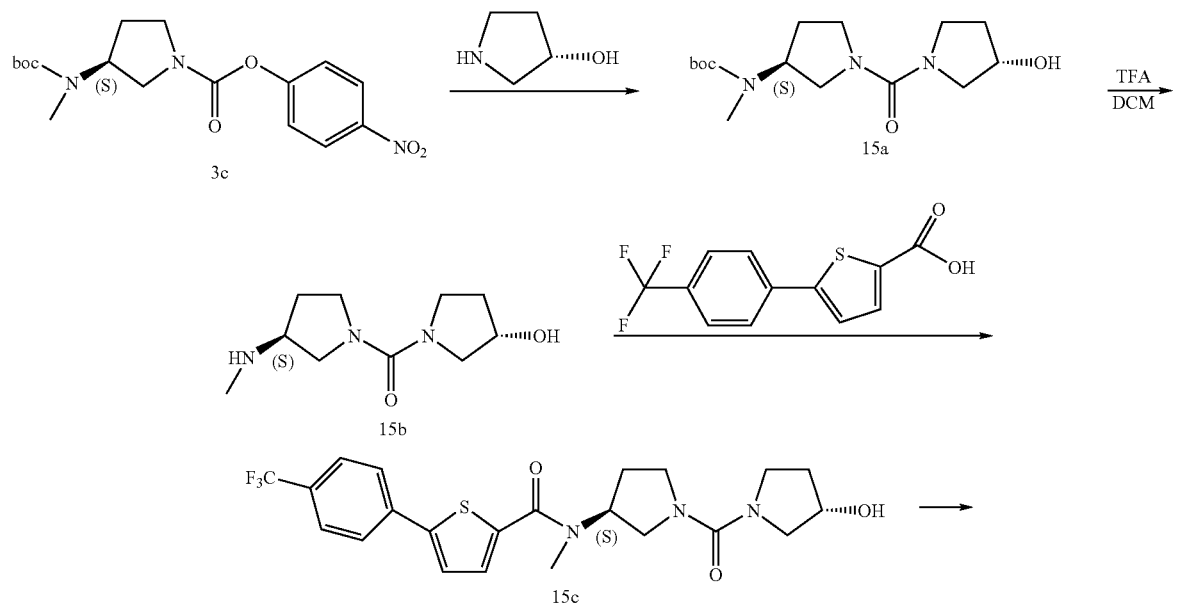

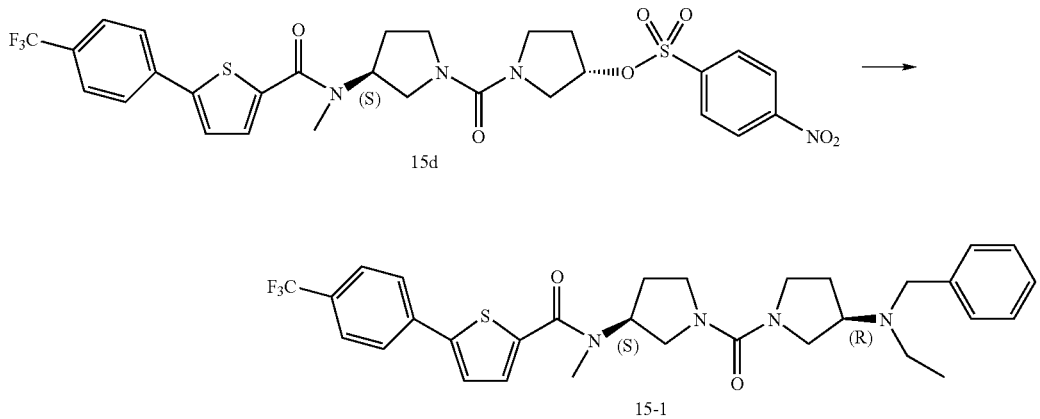

15d 15-1

Step 15A:

To a solution of 3c (5.91 g, 16.2 mmol) in DMF (50 mL), (S)-3-hydroxypyrrolidine hydrochloride (2.40 g, 19.4 mmol) and triethylamine (9.0 mL, 64.8 mmol) were added. The mixture was heated at 70° C. for 4.5 hours. The solvent was then evaporated under reduced pressure and the residue partitioned between 0.5N sodium hydroxide and 3:1 dichloromethane/isopropanol (50 mL each). The organic layer was separated and washed with 0.5N sodium hydroxide (2×50 mL). The organic layer was then dried over magnesium sulfate and the solvents were evaporated. Trituration with ether gave 15a as a tan solid (2.09 g, 41%), which was filtered, washed with ether and dried. $^1$H NMR (300 MHz, CDCl$_3$) δ 4.69 (br s, 1H), 4.45 (s, 1H), 3.34–3.62 (m, 7H), 3.26 (dd, J=10.5 7.2 Hz, 1H), 2.79 (s, 3H), 1.90–2.07 (m, 5H), 1.47 (s, 9H). APCI MS m/z: 314.2 (MH$^+$).

Step 15B:

The protected amine 15a (2.09 g, 6.58 mmol) was dissolved in dichloromethane (20 mL) and treated with TFA (20 mL). The solution was stirred at room temperature for 2 hours. The solvent was evaporated and coevaporated twice with dichloromethane. The crude, viscous oil 15b was carried to the next step without further manipulation. APCI MS m/z: 303.1 (MH+)

Step 15C:

15b (1.40 g, 6.58 mmol) was dissolved in DMF and treated with triethylamine (2.75 mL, 19.7 mmol). 4'-Trifluoromethyl-5-phenyl-thiophene-2-carboxylic acid (1.79 g, 6.58 mmol) and HOBt (1.78 g, 13.16 mmol) were added next, followed by EDC (1.39 g, 7.24 mmol). The suspension was stirred at room temperature overnight. The mixture was then partitioned between saturated bicarbonate solution and 3:1 dichloromethane/isopropanol (100 mL each). The aqueous layer was extracted with 3:1 dichloromethane/isopropanol (2×50 mL). The combined organic layers were dried over magnesium sulfate and concentrated under reduced pressure. Gradient chromatography on silica gel, using 5–10% methanol/dichloromethane afforded 15c as an off-white solid (1.56 g, 51% yield). APCI MS m/z: 468.1 (MH+)

Step 15D:

A suspension of 15c (0.70 g, 1.51 mmol), N,N-dimethyl-4-aminopyridine (0.18 g, 1.51 mmol), triethylamine (0.42 mL, 3.02 mmol) and 4-nitrobenzenesulfonyl chloride (0.50 g, 2.26 mmol) in acetonitrile (4 mL) was stirred at room temperature overnight. The resulting waxy solid was partitioned between dichloromethane and saturated sodium bicarbonate solution (50 mL each). The organic layer was separated, dried over magnesium sulfate and evaporated under reduced pressure. 1.15 g of 15d as a tan solid was obtained which was pure enough to be used without purification. $^1$H NMR (300 MHz, CDCl$_3$) δ 8.42 (d, J=8.7 Hz, 2H), 8.13 (d, J=9.3 Hz, 2H), 7.73 (d, J=8.4 Hz, 2H), 7.66 (d, J=8.7 Hz, 2H), 7.36 (d, J=3.6 Hz, 1H), 7.33 (d, J=3.9 Hz, 1H), 5.19 (m, 1H), 5.05 (m, 1H), 3.16–3.78 (m, 8H), 3.16 (s, 3H), 2.05–2.25 (m, 4H). ES MS m/z: 502.8 (MH$^+$). APCI MS m/z: 652.8 (MH$^+$).

Step 15E:

A solution of 15d (40 mg, 0.06 mmol) in N,N-dimethylacetamide (0.5 mL) was treated with 100 μL of N-ethylbenzylamine and the reaction vessel heated at 80° C. overnight. The reaction mixture was then diluted to 1.0 mL with methanol and purified on a preparative HPLC/MS system where collection was triggered by mass to give 6.5 mg (15%) of Example 15-1. $^1$H NMR (300 MHz, CDCl$_3$) δ 7.72 (d, J=8.4 Hz, 2H), 7.66 (d, J=8.7 Hz, 2H), 7.47 (s, 5H), 7.36 (d, J=4.2 Hz, 1H), 7.33 (d, J=3.9 Hz, 1H), 5.04–5.09 (m, 1H), 3.61–3.96 (m, 6H), 3.38–3.47 (m, 3H), 3.16 (s, 3H), 3.10 (q, J=7.2 Hz, 2H), 2.09–2.14 (m, 6H), 1.37 (t, J=7.5 Hz, 3H). APCI MS m/z: 585.0 (MH$^+$).

Using the appropriate starting materials, the following compounds were prepared according to the procedures described above.

| Ex. | R4 | NR1R2 | MW | MH+ | Rt | HPLC |
|---|---|---|---|---|---|---|
| 15-1 | 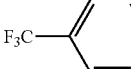 |  | 584.70 | 585.0 | 6.5 | D |
| 15-2 | 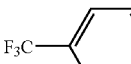 |  | 520.62 | 521.0 | 5.0 | D |
| 15-3 | 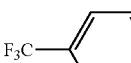 |  | 548.67 | 549.0 | 5.1 | D |
| 15-4 | 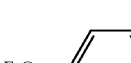 |  | 548.67 | 549.0 | 5.1 | D |
| 15-5 | 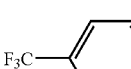 |  | 564.67 | 564.9 | 5.6 | D |
| 15-6 | 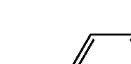 |  | 600.70 | 601.0 | 6.6 | D |
| 15-7 | 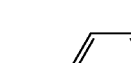 |  | 582.69 | 582.9 | 6.7 | D |
| 15-8 |  |  | 524.61 | 524.9 | 5.6 | D |
| 15-9 | 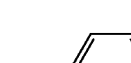 |  | 534.64 | 534.9 | 5.7 | D |

-continued
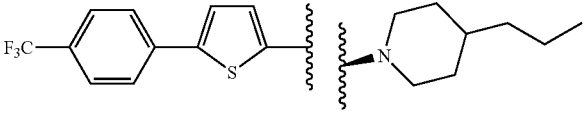
| Ex. | R₄ | NR₁R₂ | MW | MH⁺ | Rt | HPLC |
|---|---|---|---|---|---|---|
| 15-10 | 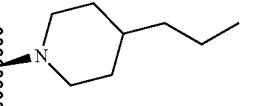 | 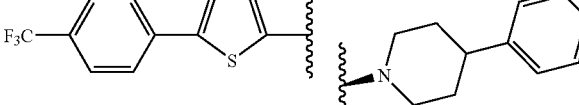 | 576.72 | 577.0 | 6.8 | D |
| 15-11 | 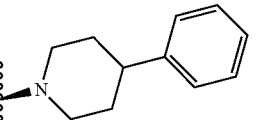 | 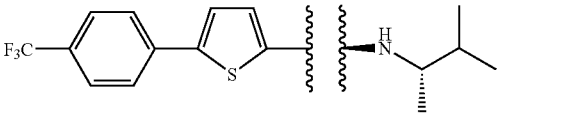 | 610.74 | 611.0 | 6.9 | D |
| 15-12 | 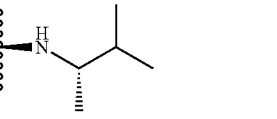 | 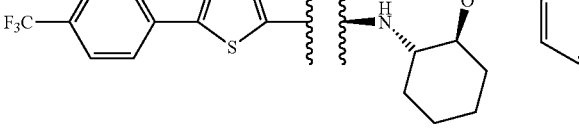 | 536.66 | 537.0 | 6.1 | D |
| 15-13 | 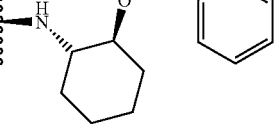 | 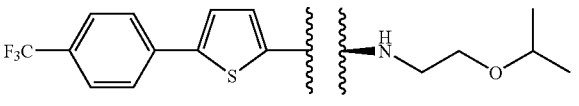 | 654.79 | 655.0 | 7.2 | D |
| 15-14 | 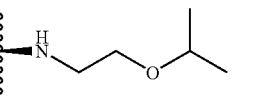 | 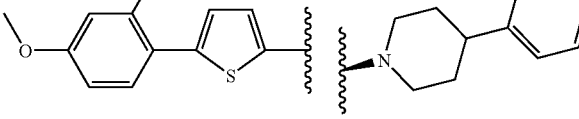 | 552.66 | 553.0 | 6.1 | D |
| 15-15 | 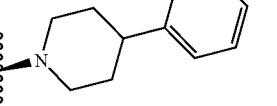 | 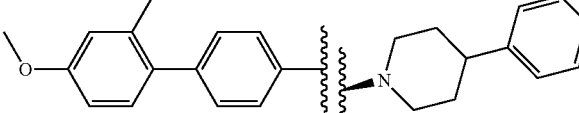 | 586.80 | 587.3 | 6.0 | D |
| 15-16 | 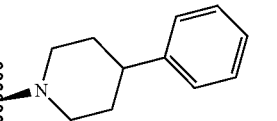 | 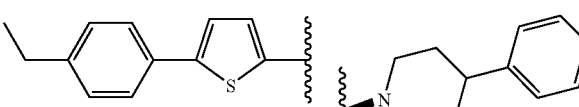 | 580.77 | 581.3 | 5.8 | D |
| 15-17 | 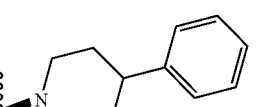 | 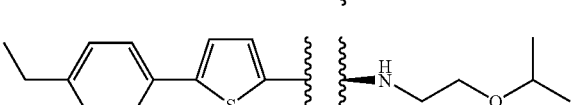 | 570.80 | 571.3 | 6.4 | D |
| 15-18 | 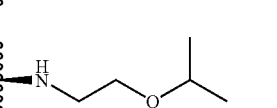 | | 512.71 | 513.3 | 5.7 | D |

Example 16

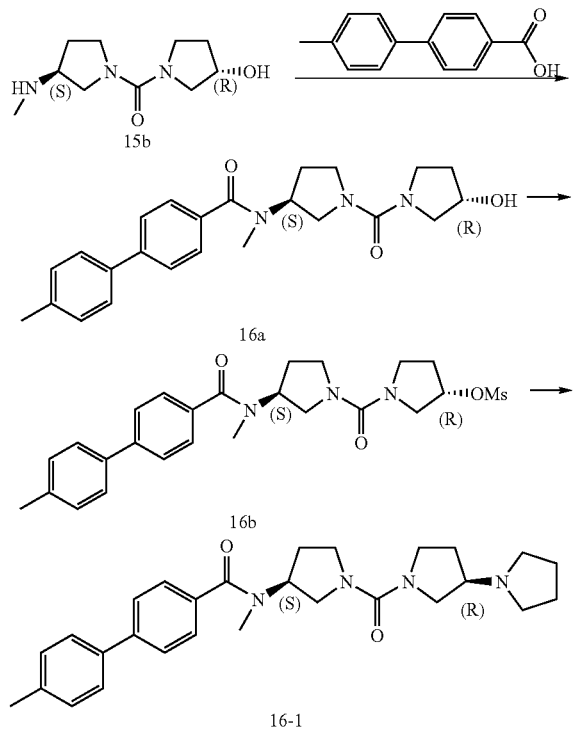

Step 16A:

To a solution of 15b (0.68 g, 3.2 mmol) in DMF (20 mL) was added 4-(4-methylphenyl)benzoic acid (0.68 g, 3.2 mmol), followed by triethylamine (1.4 mL, 9.6 mmol) and HOBt (0.86 g, 6.4 mmol). The suspension was stirred for 15 min and EDCI (0.68 g, 3.2 mmol) was added. After stirring at room temperature for 16 hours, the reaction mixture was partitioned between sat. sodium bicarbonate (100 mL) and ethyl acetate (100 mL). The aqueous phase was extracted with ethyl acetate (2×100 mL) and the combined organics were dried over magnesium sulfate, filtered and concentrated in vacuo. The crude product was purified by column chromatography eluting with 0 to 6% methanol in dichloromethane to afford 16a as a pale yellow foam (0.83 g, 63%). $^1$H NMR (300 MHz, CDCl$_3$) δ 7.62 (d, J=8.1 Hz, 2H), 7.50 (d, J=8.1 Hz, 2H), 7.45 (d, J=8.1 Hz, 2H), 7.27 (d, J=8.1 Hz, 2H), 4.46 (app qn, J=2.7 Hz, 1H), 3.40–3.70 (m, 8H), 3.01 (s, 3H), 2.41 (s, 3H), 1.85–2.15 (m, 4H), 1.59 (br s, 1H). APCI MS m/z: 408.0 (MH$^+$).

Step 16B:

To a solution of 16a (0.41 g, 1.0 mmol) in DCM (6 mL) at −40° C. under N$_2$ was added triethylamine (0.28 mL, 2.0 mmol). The solution was stirred for 15 min then methanesulfonyl chloride (85 µl, 1.1 mmol) was added in one portion. After 1 h the reaction was quenched by the addition of sat. sodium bicarbonate (20 mL) at −40° C. After warming to room temperature the layers were separated and the aqueous phase was extracted with dichloromethane (2×30 mL). The combined organics were dried over magnesium sulfate, filtered and concentrated in vacuo to afford 16b as a white solid (0.40 g, 82%). $^1$H NMR (300 MHz, CDCl$_3$) δ 7.62 (d, J=8.1 Hz, 2H), 7.50 (d, J=8.1 Hz, 2H), 7.46 (d, J=8.1 Hz, 2H), 7.28 (d, J=8.1 Hz, 2H), 5.26 (app qn, J=2.4 Hz, 1H), 3.37–3.79 (m, 8H), 3.06 (s, 3H), 3.01 (s, 3H), 2.41 (s, 3H), 2.15–2.33 (m, 4H). APCI MS m/z: 486.0 (MH$^+$).

Step 16C:

To a solution of the mesylate 16b (25 mg) in DMA (0.5 mL) was added pyrrolidine (100 µl). The reaction mixture was stirred at 80° C. overnight, filtered then purified directly by preparative HPLC collecting by mass to give Example 16-1. $^1$H NMR (300 MHz, CDCl$_3$) δ 7.62 (d, J=8.1 Hz, 2H), 7.50 (d, J=8.1 Hz, 2H), 7.45 (d, J=7.5 Hz, 2H), 7.28 (d, J=7.5 Hz, 2H), 3.3–4.00 (m, 14H), 3.00 (s, 3H), 2.41 (s, 3H), 2.03–2.20 (m, 8H). APCI MS m/z: 461.0 (MH$^+$).

Using the appropriate starting materials, the following compounds were prepared according to the procedures described above.

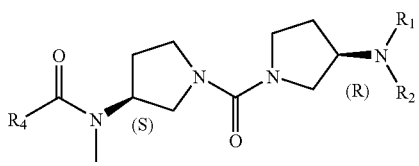

| Ex. | R$_4$ | NR$_1$R$_2$ | MW | MH$^+$ | Rt | HPLC |
|---|---|---|---|---|---|---|
| 16-1 | 4-methylphenyl-thiophene-CH$_2$ | pyrrolidine | 480.67 | 481.3 | 5.6 | D |
| 16-2 | 4-methylphenyl-thiophene-CH$_2$ | NH-CH(CH$_3$)CH$_2$OCH$_3$ | 498.69 | 499.4 | 5.0 | D |

-continued

| Ex. | R4 | NR1R2 | MW | MH+ | Rt | HPLC |
|---|---|---|---|---|---|---|
| 16-3 | 4-ethylphenyl-thiophene | piperidine | 494.70 | 495.5 | 5.0 | D |
| 16-4 | 4-ethylphenyl-thiophene | NH-CH(CH3)-iPr | 496.72 | 497.4 | 5.1 | D |
| 16-5 | 4-ethylphenyl-thiophene | NH-CH(CH3)-iPr | 496.72 | 497.4 | 5.2 | D |
| 16-6 | 4-ethylphenyl-thiophene | NH-CH2-tetrahydrofuran-2-yl | 510.70 | 511.4 | 5.0 | D |
| 16-7 | 4-ethylphenyl-thiophene | NH-CH2-tetrahydrofuran-2-yl | 510.70 | 511.4 | 5.0 | D |
| 16-8 | 4-ethylphenyl-thiophene | azepane | 508.73 | 509.4 | 5.9 | D |
| 16-9 | 4-methylphenyl-thiophene | NH-CH(Et)2 | 482.69 | 483.0 | 5.3 | D |
| 16-10 | 4-methylphenyl-thiophene | pyrrolidine | 466.65 | 467.0 | 5.0 | D |
| 16-11 | 4-methylphenyl-thiophene | azepane | 494.70 | 495.0 | 5.3 | D |
| 16-12 | 4-methylphenyl-thiophene | NH-CH(CH3)-CH2-OMe | 484.66 | 485.0 | 5.1 | D |

-continued
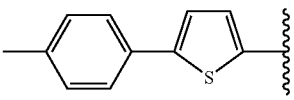
| Ex. | R₄ | NR₁R₂ | MW | MH⁺ | Rt | HPLC |
|---|---|---|---|---|---|---|
| 16-13 | 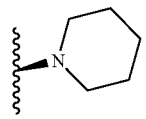 | 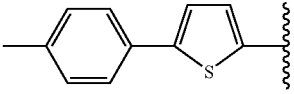 | 480.67 | 481.0 | 4.9 | D |
| 16-14 | 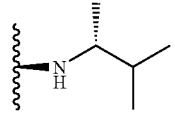 | 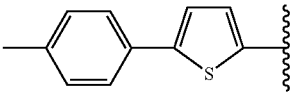 | 482.69 | 483.0 | 5.4 | D |
| 16-15 | 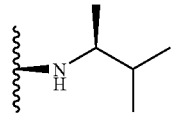 | 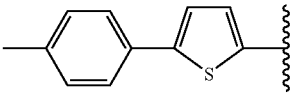 | 482.69 | 483.0 | 5.5 | D |
| 16-16 | 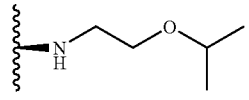 | 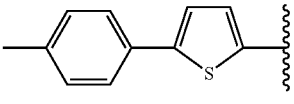 | 498.69 | 499.0 | 5.2 | D |
| 16-17 | 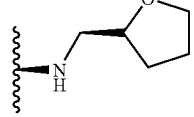 | 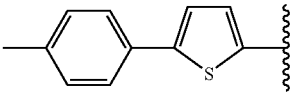 | 496.67 | 497.0 | 5.0 | D |
| 16-18 | 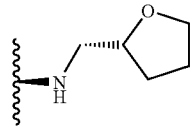 | 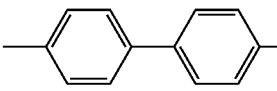 | 496.67 | 497.0 | 5.0 | D |
| 16-19 | 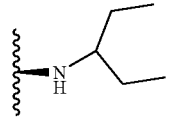 | 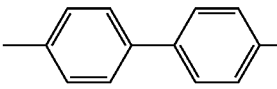 | 476.66 | 477.0 | 5.3 | D |
| 16-20 | 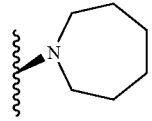 | 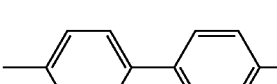 | 488.67 | 489.0 | 5.1 | D |
| 16-21 | 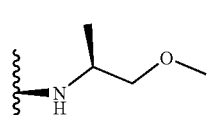 | 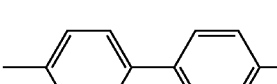 | 478.63 | 479.0 | 4.9 | D |
| 16-22 | 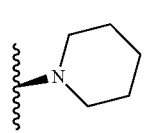 | | 474.64 | 475.0 | 5.0 | D |

-continued
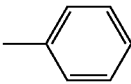
| Ex. | R₄ | NR₁R₂ | MW | MH⁺ | Rt | HPLC |
|---|---|---|---|---|---|---|
| 16-23 | 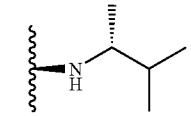 | 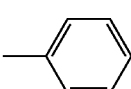 | 476.66 | 477.0 | 5.2 | D |
| 16-24 | 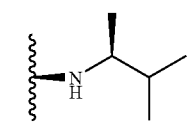 | 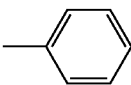 | 476.66 | 477.1 | 5.2 | D |
| 16-25 | 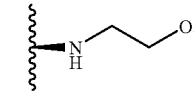 | 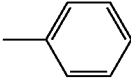 | 492.66 | 493.0 | 5.1 | D |
| 16-26 | 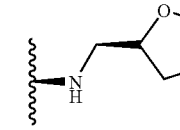 | 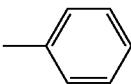 | 490.64 | 491.0 | 5.0 | D |
| 16-27 | 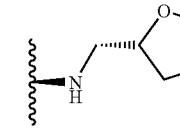 | 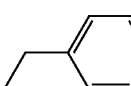 | 490.64 | 491.1 | 4.9 | D |
| 16-28 | 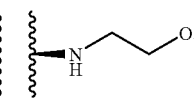 | 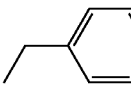 | 496.67 | 497.4 | 5.4 | D |
| 16-29 | 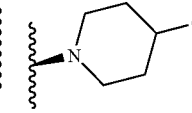 | 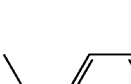 | 510.70 | 511.4 | 5.4 | D |
| 16-30 | 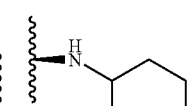 | 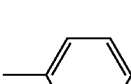 | 526.70 | 526.8 | 22.0 | H |
| 16-31 | 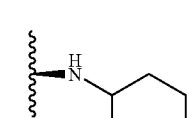 | 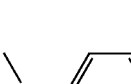 | 496.67 | 497.0 | 22.7 | H |
| 16-32 | 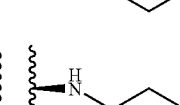 | | 512.67 | 513.0 | 21.0 | H |

-continued
| Ex. | R₄ | NR₁R₂ | MW | MH⁺ | Rt | HPLC |
|---|---|---|---|---|---|---|
| 16-33 | ethyl-phenyl-thiophene | tetrahydropyran-4-yl-NH | 510.7 | 511.4 | 4.6 | D |
Example 17
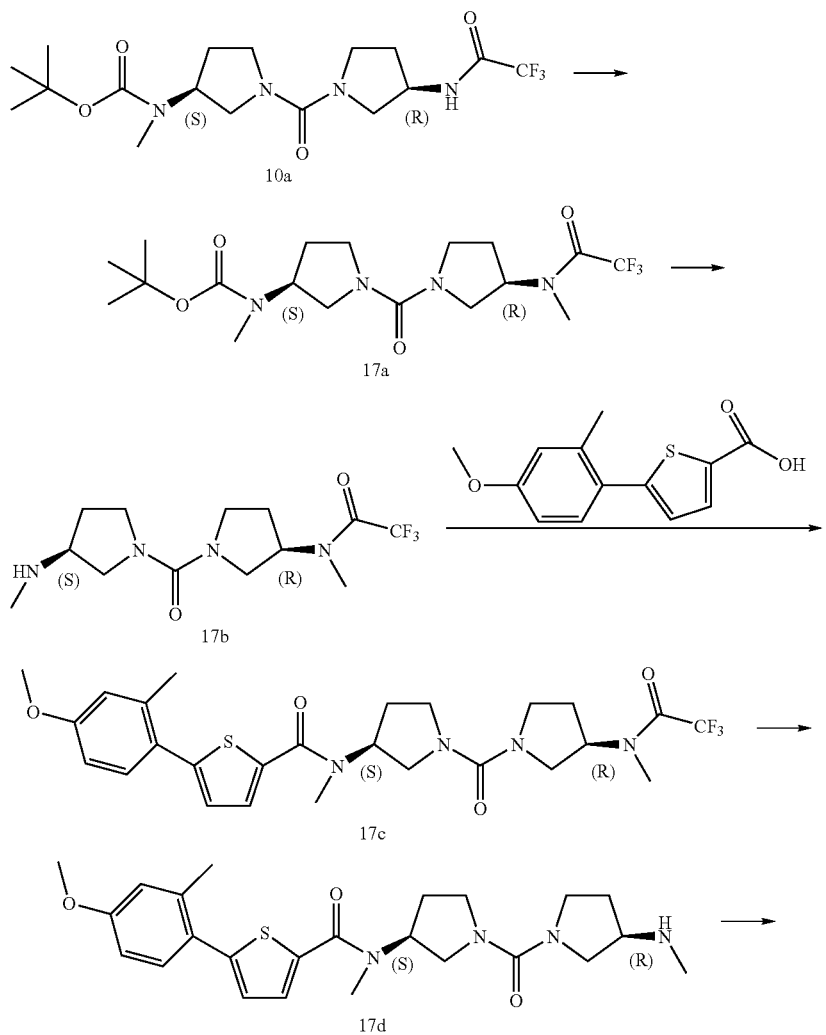

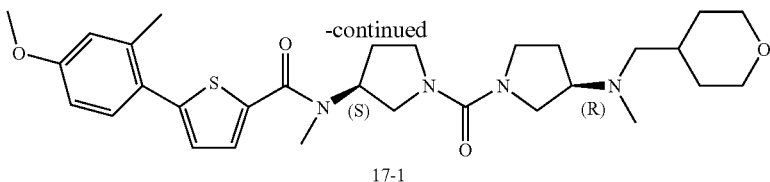

17-1

Step 17A:

To a stirred solution of 10b (2.37 g, 5.8 mmol) in DMF (65 mL) was added methyl iodide (5.4 mL, 87 mmol) followed by potassium carbonate (4 g, 29 mmol). The reaction mixture was stirred at 80° C. for 14 h then allowed to cool to room temperature. The suspension was concentrated in vacuo then partitioned between ethyl acetate (100 mL) and brine (50 mL). The aqueous phase was extracted with ethyl acetate (2×50 mL) and the combined organics dried over magnesium sulfate, filtered and concentrated in vacuo to afford 17a as a yellow oil which solidified when under high vacuum overnight (2.4 g, 98%). The compound was found to be a 2:1 mixture of amide atropisomers by $^1$H NMR. $^1$H NMR (300 MHz, CDCl3) δ 5.00 (app qn, J=6.9 Hz, 0.65H), 4.70 (br s, 1H), 4.62 (app qn, J=7.2 Hz, 0.35H), 3.26–3.77 (m, 8H), 3.07 (s, 2H), 2.98 (s, 1H), 2.80 (s, 3H), 1.94–2.42 (m, 4H), 1.47 (s, 9H). APCI MS m/z: 423.0 (MH+).

Step 17B:

17a (1.29 g, 3 mmol) in dichloromethane (10 mL) was treated with trifluoroacetic acid (10 mL). After 30 min the reaction mixture was concentrated in vacuo removing residual TFA with a fast stream of $N_2$ to afford 17b as a brown oil that was used in the next reaction without further purification. APCI MS m/z: 323.0 (MH+).

Step 17C:

Amine 17b (2 mmol) in DMF (9 mL) was treated with triethylamine (0.84 mL, indicator paper shows pH 8). 5-(2-Methyl-4-methoxyphenyl)thiophene-2-carboxylic acid (0.60 g, 2.4 mmol) was added followed by HOBt (0.54 g, 4 mmol) and EDCI (0.42 g, 2.2 mmol). The reaction mixture was stirred at room temperature overnight then partitioned between ethyl acetate (200 mL) and sat. sodium bicarbonate (aq) (100 mL). The aqueous phase was extracted with ethyl acetate (2×50 mL) and the combined organics dried over magnesium sulfate, filtered and concentrated in vacuo to afford a brown oil which was purified by column chromatography eluting with 0 to 2% methanol in dichloromethane to afford 17c a white solid (0.92 g, 88%). The compound was found to be a 2:1 mixture of amide atropisomers by $^1$H NMR. $^1$H NMR (300 MHz, CDCl3) δ 7.33 (d, J=8.4 Hz, 1H), 7.32 (d, J=3.9 Hz, 1H), 6.95 (d, J=3.9 Hz, 1H), 6.75–6.83 (m, 2H), 4.98–5.15 (m, 1.65H), 4.61 (m, 0.35H), 3.83 (s, 3H), 3.59–3.77 (m, 4H), 3.35–3.50 (m, 4H), 3.17 (s, 3H), 3.07 (d, J=1.8 Hz, 2H), 2.99 (s, 1H), 2.42 (s, 3H), 2.00–2.24 (m, 4H). APCI MS m/z: 552.9 (MH+).

Step 17D:

To a solution of the 17c (0.92 g, 1.7 mmol) in methanol (20 mL) and water (2 mL) was added potassium carbonate (1.15 g, 8.3 mmol). The mixture was heated at 80° C. for 14 h then allowed to cool to room temperature. The suspension was concentrated in vacuo then partitioned between ethyl acetate (100 mL) and water (50 mL). The aqueous phase was extracted with ethyl acetate (2×50 mL) and the combined organics dried over magnesium sulfate, filtered and concentrated in vacuo to afford a white foam, 17d, which was used without further purification (0.55 g, 71%). A small sample was purified by preparative HPLC. APCI MS m/z: 456.8 (MH$^+$).

Step 17E:

To a solution of the 17d (20 mg, 0.04 mmol) in methanol (1 mL) was added tetrahydropyranyl-4-carboxaldehyde (29 mg, 0.2 mmol) followed by sodium triacetoxyborohydride (25 mg, 0.08 mmol). The reaction mixture was stirred at room temperature, filtered, then purified directly by preparative HPLC collecting by mass to give compound Example 17-1 (20 mg, 76%). $^1$H NMR (300MHz, CDCl3) δ 7.31–7.35 (m, 2H), 6.95 (d, J=3.9 Hz, 1H), 6.76–6.83 (m, 2H), 5.06 (m, 1H), 3.86–4.01 (m, 3H), 3.83 (s, 3H), 3.59–3.77 (m, 5H), 3.35–3.52 (m, 5H), 3.17 (s, 3H), 2.85 (s, 3H), 2.41 (s, 3H), 2.32–2.40 (m, 2H), 2.10–2.21 (m, 2H), 2.32–2.40 (m, 3H), 1.64–1.80 (m, 2H), 1.35–1.48 (m, 2H). APCI MS m/z: 554.8 (MH$^+$).

Using the appropriate starting materials, the following compounds were prepared according to the procedures described above.

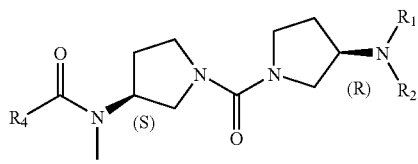

| Ex. | R$_4$ | NR$_1$R$_2$ | MW | MH$^+$ | Rt | HPLC |
|---|---|---|---|---|---|---|
| 17-1 | | | 524.73 | 525.3 | 21.1 | E |

-continued

| Ex. | R₄ | NR₁R₂ | MW | MH⁺ | Rt | HPLC |
|---|---|---|---|---|---|---|
| 17-2 | 4-ethylphenyl-thiophene | N-methyl-N-(cyclopropylmethyl) | 494.70 | 495.4 | 5.4 | D |
| 17-3 | 4-ethylphenyl-thiophene | N-methyl-N-(3-cyclopentylpropyl) | 550.81 | 551.4 | 6.5 | D |
| 17-4 | 4-ethylphenyl-thiophene | N-methyl-N-(2-(tetrahydropyran-4-yl)ethyl) | 552.78 | 553.4 | 5.6 | D |
| 17-5 | 4-ethylphenyl-thiophene | N-methyl-N-(3-cyclohexylpropyl) | 564.83 | 565.5 | 6.4 | D |
| 17-6 | 4-methoxy-2-methylbiphenyl | N-methyl-N-(cyclopropylmethyl) | 504.67 | 505.4 | 4.9 | D |
| 17-7 | 4-methoxy-2-methylbiphenyl | N-methyl-N-(3-cyclopentylpropyl) | 560.78 | 561.5 | 5.8 | D |
| 17-8 | 4-methoxy-2-methylbiphenyl | N-methyl-N-(2-(tetrahydropyran-4-yl)ethyl) | 562.75 | 563.5 | 4.9 | D |
| 17-9 | 4-methoxy-2-methylbiphenyl | N-methyl-N-(3-cyclohexylpropyl) | 574.80 | 575.5 | 6.1 | D |
| 17-10 | 4-ethylphenyl-thiophene | N-methyl-N-((tetrahydropyran-4-yl)methyl) | 538.75 | 539.0 | 5.2 | D |
| 17-11 | 4-ethylphenyl-thiophene | N-methyl-N-cyclobutyl | 494.70 | 495.0 | 5.2 | D |

| Ex. | R₄ | NR₁R₂ | MW | MH⁺ | Rt | HPLC |
|---|---|---|---|---|---|---|
| 17-12 | 2-methyl-4-methoxybiphenyl | N-methyl-(tetrahydropyran-4-yl)methyl | 548.72 | 549.1 | 4.8 | D |
| 17-13 | 2-methyl-4-methoxybiphenyl | N-methyl-cyclobutyl | 504.67 | 505.1 | 4.8 | D |
| 17-14 | 4-ethylphenyl-thiophene | N-methyl-tetrahydropyran-4-yl | 524.73 | 524.8 | 1.7 | G |
| 17-15 | 2-methyl-4-methoxyphenyl-thiophene | N-methyl-ethyl | 484.66 | 484.8 | 1.7 | G |
| 17-16 | 2-methyl-4-methoxyphenyl-thiophene | N-methyl-cyclopropylmethyl | 510.70 | 510.8 | 1.6 | G |
| 17-17 | 2-methyl-4-methoxyphenyl-thiophene | N-methyl-3-cyclopentylpropyl | 566.81 | 566.8 | 1.5 | G |
| 17-18 | 2-methyl-4-methoxyphenyl-thiophene | N-methyl-2-(tetrahydropyran-4-yl)ethyl | 568.78 | 568.8 | 1.7 | G |
| 17-19 | 2-methyl-4-methoxyphenyl-thiophene | N-methyl-3-cyclohexylpropyl | 580.83 | 580.8 | 1.5 | G |
| 17-20 | 2-methyl-4-methoxyphenyl-thiophene | N-methyl-cyclobutyl | 510.70 | 510.8 | 1.6 | G |
| 17-21 | 4-ethylphenyl-thiophene | N-methyl-ethyl | 468.66 | 468.9 | 1.7 | G |

| Ex. | R₄ | NR₁R₂ | MW | MH⁺ | Rt | HPLC |
|---|---|---|---|---|---|---|
| 17-22 | 4-methoxy-2-methylbiphenyl | N-methyl-tetrahydropyran-4-yl | 534.70 | 535.1 | 4.6 | D |
| 17-23 | 4-ethyl-2-methylbiphenyl | N-methyl-ethyl | 462.63 | 463.1 | 4.9 | D |
| 17-24 | 4-ethyl-2-methylbiphenyl | N-methyl-cyclopropylmethyl | 488.67 | 489.1 | 4.9 | D |
| 17-25 | 4-ethyl-2-methylbiphenyl | N-methyl-(tetrahydropyran-4-yl)methyl | 532.72 | 533.1 | 5.0 | D |
| 17-26 | 4-ethyl-2-methylbiphenyl | N-methyl-3-cyclopentylpropyl | 544.78 | 545.2 | 5.3 | D |
| 17-27 | 4-ethyl-2-methylbiphenyl | N-methyl-2-(tetrahydropyran-4-yl)ethyl | 546.75 | 547.2 | 4.8 | D |
| 17-28 | 4-ethyl-2-methylbiphenyl | N-methyl-3-cyclohexylpropyl | 558.81 | 559.2 | 5.4 | D |
| 17-29 | 4-ethyl-2-methylbiphenyl | N-methyl-cyclobutyl | 488.67 | 489.1 | 5.0 | D |
| 17-30 | 4-methoxy-2-methylbiphenyl | N-methyl-ethyl | 478.63 | 479.1 | 4.5 | D |

-continued

| Ex. | R₄ | NR₁R₂ | MW | MH⁺ | Rt | HPLC |
|---|---|---|---|---|---|---|
| 17-31 | 4-ethyl-2-methylbiphenyl | N-methyl-(tetrahydropyran-4-yl) | 518.70 | 519.1 | 4.8 | D |
| 17-32 | 5-(4-methoxy-2-methylphenyl)thiophen-2-yl | N-methyl-cyclopentyl | 524.73 | 525.5 | 5.1 | D |
| 17-33 | 4-ethyl-2-methylbiphenyl | N-cyclopentyl | 502.70 | 503.5 | 5.5 | D |
| 17-34 | 4-ethyl-2-methylbiphenyl | N-methyl-isopropyl | 476.66 | 477.4 | 4.7 | D |
| 17-35 | 4-methoxy-2-methylbiphenyl | N-methyl-isopropyl | 492.66 | 493.1 | 4.6 | D |
| 17-36 | 4-methoxy-2-methylbiphenyl | N-methyl-(pentan-3-yl) | 520.71 | 521.2 | 4.8 | D |
| 17-37 | 5-(4-methoxy-2-methylphenyl)thiophen-2-yl | N-methyl-isopropyl | 498.69 | 499.5 | 4.6 | D |
| 17-38 | 5-(4-methoxy-2-methylphenyl)thiophen-2-yl | N-methyl-(tetrahydropyran-4-ylmethyl) | 554.75 | 554.8 | 1.7 | G |
| 17-39 | 5-(4-ethylphenyl)thiophen-2-yl | NH-methyl | 440.61 | 441.3 | 5.0 | D |
| 17-40 | 4-methoxy-2-methylbiphenyl | NH-methyl | 450.58 | 451.3 | 4.6 | D |

-continued
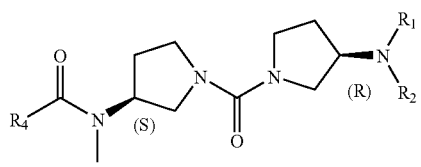
| Ex. | R₄ | NR₁R₂ | MW | MH⁺ | Rt | HPLC |
|---|---|---|---|---|---|---|
| 17-41 | methoxy-methyl-phenyl-thiophene | NHMe | 456.61 | 456.8 | 1.7 | G |
| 17-42 | ethyl-methyl-biphenyl | NHMe | 434.58 | 435.1 | 4.8 | D |
| 17-43 | ethyl-phenyl-thiophene | N(Me)cyclopentyl | 508.73 | 509.0 | 5.2 | D |
| 17-44 | methyl-phenyl-thiophene | N(Me)tetrahydropyranyl | 510.70 | 511.2 | 5.0 | D |
| 17-45 | methyl-biphenyl | N(Me)cyclopentyl | 488.67 | 488.9 | 1.7 | D |
| 17-46 | methyl-biphenyl | N(Me)isobutyl | 476.66 | 477.3 | 5.2 | D |
| 17-47 | methyl-phenyl-thiophene | N(Me)cyclopentyl | 494.70 | 495.3 | 5.2 | D |
Example 18
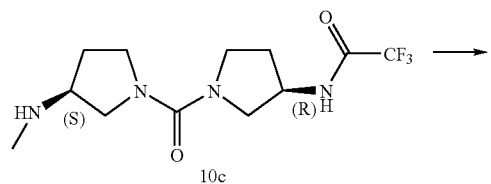
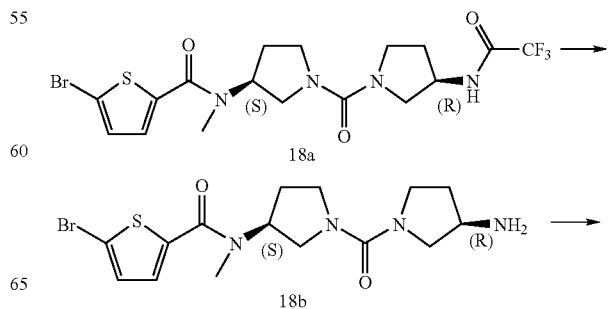

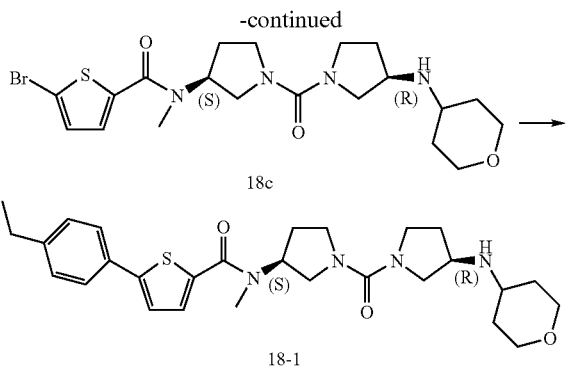

Step 18A:

To a solution of 10c (0.36 g, 1.16 mmol) in dichloromethane (15 mL) was charged 5-Bromo-2-thiophenecarboxylic acid (0.30 g, 1.57 mmol). To this solution was added triethylamine (0.5 mL, 3.58 mmol), followed by HOBt (0.22 g, 1.67 mmol). The reaction mixture was allowed to stir until all dissolved. EDC (0.32 g, 1.67 mmol) was then added and the reaction mixture was allowed to stir overnight at room temperature. After 18 h, the reaction was diluted in ethyl acetate (100 mL) and washed with sodium bicarbonate (25 mL, sat. aq.). The organic portion was separated and washed with dilute hydrochloric acid (25 mL, 1N aq.), dried over sodium sulfate, filtered and concentrated to yield a yellow solid (18a, 0.49 g, 85%). $^1$H NMR (CDCL3, 300 MHz) δ 7.19 (d, J=4 Hz, 1H), 7.02 (d, J=4 Hz, 1H), 4.87 (p, J=7 Hz, 1H), 3.87 (d, J=11 Hz, 2H), 3.48–3.72 (m, 4H), 3.18–3.43 (m, 6H), 3.05–3.11 (m, 1H), 3.12 (s, 3H), 2.65–2.79 (m, 1H). APCI MS m/z: 497 (MH$^+$).

Step 18B:

To a solution of 18a (0.45 g, 0.91 mmol) in ethanol (10 mL) was charged potassium carbonate (0.55 g, 4.0 mmol). Water (1 mL) was added, and the reaction mixture was allowed to stir overnight at 80° C. After 18 h, the reaction was filtered through a pad of Celite, which was then rinsed with ethanol (3×50 mL). The organic was concentrated to yield a yellow oil (18b, 0.33 g, 92%). The compound was used without further purification. APCI MS m/z: 401 (MH$^+$).

Step 18C:

To a solution of 18b (0.33 g, 0.84 mmol) in methanol (20 mL) was charged tetrahydropyran-4-one (0.3 g, 3.3 mmol), followed by the addition of sodium triacetoxyborohydride (0.9 g, 4.4 mmol). The reaction mixture was allowed to stir overnight at room temperature. After 18 hrs, the reaction was diluted in 4:1 dichloromethane:isopropanol (100 mL) and washed with sodium bicarbonate (25 mL, sat. aq.). The organic portion was separated and dried with sodium sulfate, filtered and concentrated to yield a yellow solid (18c, 0.28 g, 69% ). Compound was purified on silica (95:5 dichloromethane:methanol). $^1$H NMR (CDCL3, 300 MHz) δ 7.11 (d, J=3.9 Hz, 1H), 7.01 (d, J=3.9 Hz, 1H), 4.97 (p, J=7.5Hz, 1H), 3.96 (d, J=11.9 Hz, 2H), 3.51–3.66 (m, 4H), 3.32–3.48 (m, 6H), 3.06–3.11 (m, 1H), 3.09 (s, 3H), 2.66–2.76 (m, 1H), 1.97–2.12 (m, 2H), 1.65–1.77 (m, 1H), 1.30–1.45 (m, 3H). APCI MS m/z: 485 (MH$^+$).

Step 18D:

To a solution of 18c (0.28 g, 0.58 mmol) in toluene:ethanol (2:1, 30 mL) was charged 4-ethylphenyl boronic acid (0.17 g, 1.16 mmol). To this solution was added 2N sodium carbonate (10 mL, 20 mmol). The reaction mixture was degassed by bubbling nitrogen for 10 minutes. Tetrakis (triphenyphosphine)palladium(0) (0.05 g, 0.05 mmol) was then added and the reaction mixture was degassed again with nitrogen for 10 min. The reaction was sealed and allowed to stir overnight at 80° C. After 18 h, the reaction was cooled and TLC showed exhaustion of starting material. The reaction was diluted in ethyl acetate (100 mL) and washed with sodium bicarbonate (25 mL, sat. aq.). The organic portion was separated and washed with Brine (25 mL, sat. aq.). The organic portion was separated and dried with sodium sulfate, filtered and concentrated to yield a yellow solid The compound was purified on silica eluting with 95:5 dichloromethane:methanol to yield a white powder (Example 18-1, 0.11 g, 38%). $^1$H NMR (CDCl$_3$, 300 MHz), δ 7.53 (d, J=8.1 Hz, 2H), 7.32 (d, J=3.3 Hz, 1H), 7.23 (d, J=8.1 Hz, 2H), 7.20 (d, J=3.3 Hz, 1H), 5.06 (p, J=7.6 Hz, 1H), 3.97 (m, 2H), 3.53–3.71 (m, 4H), 3.34–3.49 (m, 6H), 3.14 (s, 3H), 3.07–3.13 (m, 2H), 2.70–2.77 (m, 1H), 2.67 (q, J=7.5 Hz, 2H), 1.98–2.15 (m, 2H), 1.66–1.75 (m, 1H), 1.32–1.46 (m, 3H), 1.25 (t, J=7.5 Hz, 3H). APCI MS m/z: 511 (MH$^+$).

Using the appropriate starting materials, the following compounds were prepared according to the procedures described above.

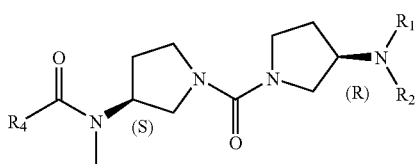

| Ex. | R$_4$ | NR$_1$R$_2$ | MW | MH$^+$ | Rt | HPLC |
|---|---|---|---|---|---|---|
| 18-1 | | | 510.70 | 511.4 | 4.6 | D |

-continued

| Ex. | R₄ | NR₁R₂ | MW | MH⁺ | Rt | HPLC |
|---|---|---|---|---|---|---|
| 18-2 | 4-(trifluoromethyl)phenyl-thiophene | NH-(4,4-dimethylcyclohexyl) | 576.72 | 576.7 | 1.6 | G |
| 18-3 | 4-(trifluoromethoxy)phenyl-thiophene | NH-(4,4-dimethylcyclohexyl) | 592.72 | 592.7 | 1.6 | G |
| 18-4 | 4-methoxy-2-methylphenyl-thiophene | NH-(4,4-dimethylcyclohexyl) | 552.78 | 552.8 | 1.7 | G |
| 18-5 | 4-(trifluoromethyl)phenyl-thiophene | NH-(4-methylcyclohexyl) | 562.70 | 562.7 | 1.7 | G |
| 18-6 | 4-(trifluoromethoxy)phenyl-thiophene | NH-(4-methylcyclohexyl) | 578.70 | 578.7 | 1.6 | G |
| 18-7 | 4-methoxy-2-methylphenyl-thiophene | NH-(4-methylcyclohexyl) | 538.75 | 538.8 | 1.7 | G |
| 18-8 | 4-chloro-2-(trifluoromethyl)phenyl-thiophene | NH-(4-methylcyclohexyl) | 597.14 | 596.7 | 1.6 | G |
| 18-9 | 4-(trifluoromethyl)phenyl-thiophene | NH-(tetrahydropyran-4-yl) | 550.64 | 550.7 | 1.8 | G |
| 18-10 | 4-(trifluoromethoxy)phenyl-thiophene | NH-(tetrahydropyran-4-yl) | 566.64 | 566.7 | 1.7 | G |

-continued
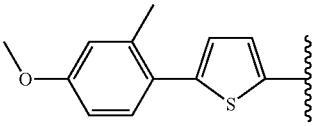
| Ex. | R₄ | NR₁R₂ | MW | MH⁺ | Rt | HPLC |
|---|---|---|---|---|---|---|
| 18-11 | 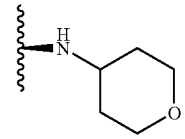 | 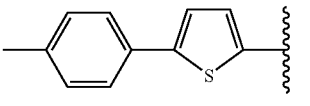 | 526.70 | 526.8 | 1.8 | G |
| 18-12 | 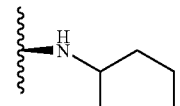 | 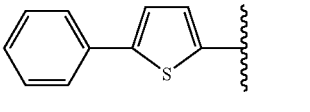 | 522.75 | 522.8 | 1.7 | G |
| 18-13 | 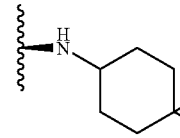 | 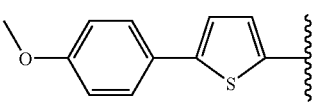 | 508.73 | 508.8 | 1.8 | G |
| 18-14 | 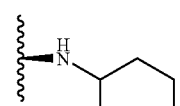 | 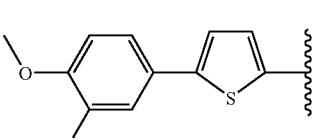 | 538.75 | 538.8 | 1.8 | G |
| 18-15 | 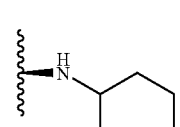 | 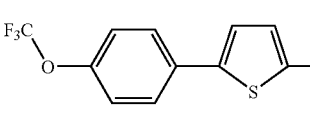 | 556.74 | 556.8 | 1.7 | G |
| 18-16 | 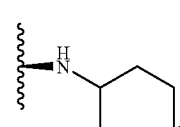 | 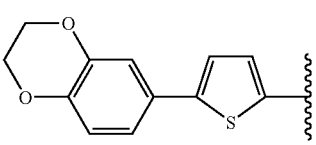 | 592.72 | 592.7 | 1.6 | G |
| 18-17 | 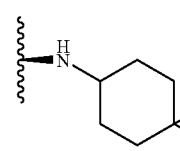 | 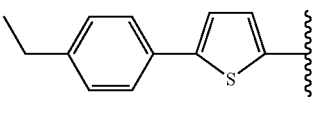 | 566.76 | 566.8 | 1.8 | G |
| 18-18 | 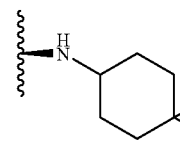 | 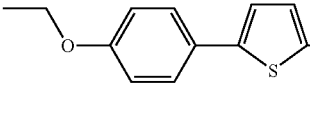 | 536.78 | 536.8 | 1.7 | G |
| 18-19 | 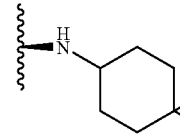 | | 552.78 | 552.8 | 1.8 | G |

-continued

| Ex. | R₄ | NR₁R₂ | MW | MH⁺ | Rt | HPLC |
|---|---|---|---|---|---|---|
| 18-20 | 4-methylphenyl-thiophene | N-tetrahydropyran-4-yl | 496.67 | 496.8 | 1.8 | G |
| 18-21 | 4-methoxyphenyl-thiophene | N-tetrahydropyran-4-yl | 512.67 | 512.8 | 1.9 | G |
| 18-22 | 3-fluoro-4-methoxyphenyl-thiophene | N-tetrahydropyran-4-yl | 530.66 | 530.8 | 1.9 | G |
| 18-23 | 4-trifluoromethoxyphenyl-thiophene | N-tetrahydropyran-4-yl | 566.64 | 566.7 | 1.8 | G |
| 18-24 | 2,3-dihydrobenzo[1,4]dioxin-6-yl-thiophene | N-tetrahydropyran-4-yl | 540.68 | 540.7 | 1.9 | G |
| 18-25 | 4-ethoxyphenyl-thiophene | N-tetrahydropyran-4-yl | 526.70 | 526.8 | 1.8 | G |
| 18-26 | 3-fluoro-4-methylphenyl-thiophene | N-tetrahydropyran-4-yl | 514.66 | 514.8 | 1.8 | G |
| 18-27 | 3-fluoro-4-methoxyphenyl-thiophene | N-tetrahydropyran-4-yl | 530.66 | 530.7 | 1.9 | G |
| 18-28 | 2,4-dimethylphenyl-thiophene | N-tetrahydropyran-4-yl | 510.70 | 510.8 | 1.8 | G |

-continued

| Ex. | R₄ | NR₁R₂ | MW | MH⁺ | Rt | HPLC |
|---|---|---|---|---|---|---|
| 18-29 | 4-isopropylphenyl-thiophene | tetrahydropyran-4-ylamino | 524.73 | 524.8 | 1.8 | G |
| 18-30 | 3-fluoro-4-methylphenyl-thiophene | (tetrahydropyran-4-ylmethyl)amino | 528.69 | 528.7 | 6.8 | I |
| 18-31 | 3-fluoro-4-methoxyphenyl-thiophene | (tetrahydropyran-4-ylmethyl)amino | 544.69 | 544.7 | 6.1 | I |
| 18-32 | 2,4-dimethylphenyl-thiophene | (tetrahydropyran-4-ylmethyl)amino | 524.73 | 524.8 | 6.9 | I |
| 18-33 | 4-isopropylphenyl-thiophene | (tetrahydropyran-4-ylmethyl)amino | 538.75 | 538.8 | 7.5 | I |

Example 19

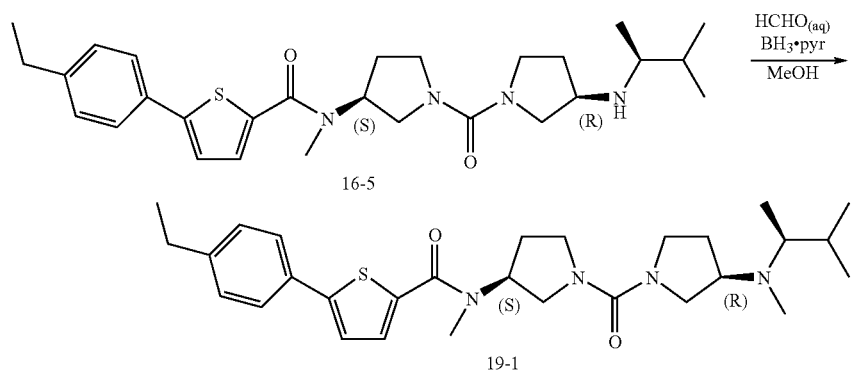

Step 19A:

To a solution of the Example 16-5 (5 mg) in methanol (0.8 mL) was added formaldehyde (37 wt. % solution in water, 50 μl) followed by borane pyridine (20 μl). The reaction mixture was stirred for 16 h at room temperature, filtered and purified directly by preparative HPLC collecting by mass threshold to give 4.3 mg (84%) of Example 19-1. APCI MS m/z: 511.4 (MH⁺).

Using the appropriate starting materials, the following compounds were prepared according to the procedures described above.

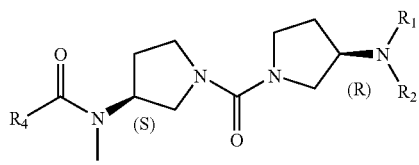

| Ex. | R₄ | NR₁R₂ | MW | MH⁺ | Rt | HPLC |
|---|---|---|---|---|---|---|
| 19-2 | (4-ethylphenyl-thienyl) | N-methyl-isobutyl | 510.74 | 511.4 | 6.1 | D |
| 19-2 | (4-ethylphenyl-thienyl) | N-methyl-methoxymethyl | 512.71 | 513.3 | 5.8 | D |
| 19-3 | (4-ethylphenyl-thienyl) | N-methyl-methoxymethyl | 510.74 | 398.3 | 6.1 | D |
| 19-4 | (4-ethylphenyl-thienyl) | N-methyl-tetrahydrofuranylmethyl | 524.73 | 525.2 | 5.8 | D |
| 19-5 | (4-ethylphenyl-thienyl) | N-methyl-tetrahydrofuranylmethyl | 524.73 | 525.4 | 5.8 | D |
| 19-6 | (4-ethylphenyl-thienyl) | N-methyl-pentan-3-yl | 510.74 | 511.1 | 5.5 | D |
| 19-7 | (4-ethylphenyl-thienyl) | N-methyl-(2-isopropoxyethyl) | 526.74 | 527.0 | 5.4 | D |
| 19-8 | (4-methylphenyl-thienyl) | N-methyl-pentan-3-yl | 496.72 | 497.1 | 5.3 | D |
| 19-9 | (4-methylphenyl-thienyl) | N-methyl-isopropyl | 468.66 | 469.0 | 5.1 | D |
| 19-10 | (4-methylphenyl-thienyl) | N-methyl-(2-isopropoxyethyl) | 512.71 | 513.1 | 5.2 | D |

-continued

| Ex. | R₄ | NR₁R₂ | MW | MH⁺ | Rt | HPLC |
|---|---|---|---|---|---|---|
| 19-11 | 4-phenylthiophen-2-yl | N-Me, CH₂-(tetrahydrofuran-2-yl) | 510.70 | 511.0 | 5.2 | D |
| 19-12 | 4-phenylthiophen-2-yl | N-Me, CH₂-(tetrahydrofuran-2-yl) (other stereo) | 510.70 | 511.1 | 5.2 | D |
| 19-13 | biphenyl-4-yl | N-Me, CH(Et)₂ | 490.69 | 491.2 | 5.3 | D |
| 19-14 | biphenyl-4-yl | N-Me, CH(Me)OMe | 492.66 | 493.1 | 5.1 | D |
| 19-15 | biphenyl-4-yl | N-Me, iPr | 462.63 | 463.5 | 5.0 | D |
| 19-16 | biphenyl-4-yl | N-Me, CH(Me)iPr | 490.69 | 491.1 | 5.3 | D |
| 19-17 | biphenyl-4-yl | N-Me, CH(Me)iPr | 490.69 | 491.1 | 5.3 | D |
| 19-18 | biphenyl-4-yl | N-Me, CH₂CH₂OiPr | 506.69 | 507.1 | 5.3 | D |
| 19-19 | biphenyl-4-yl | N-Me, CH₂-(tetrahydrofuran-2-yl) | 504.67 | 505.1 | 5.1 | D |
| 19-20 | biphenyl-4-yl | N-Me, CH₂-(tetrahydrofuran-2-yl) | 504.67 | 505.1 | 5.2 | D |
| 19-21 | 4-(4-CF₃-phenyl)thiophen-2-yl | N-Me, cyclopentyl | 548.67 | 548.7 | 1.8 | G |

-continued

| Ex. | R₄ | NR₁R₂ | MW | MH⁺ | Rt | HPLC |
|---|---|---|---|---|---|---|
| 19-22 | 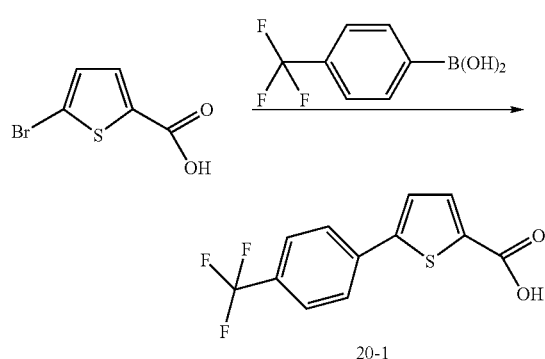 | | 562.70 | 562.7 | 1.7 | G |

Example 20

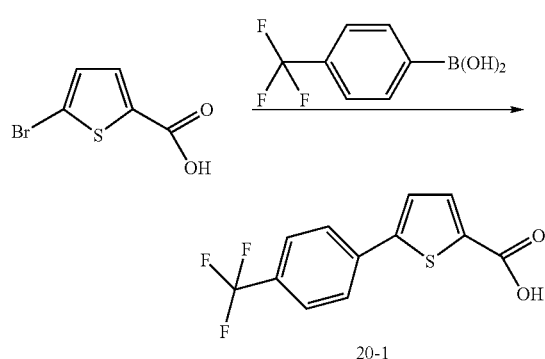

Step 20A:

To a 500 mL round bottomed flask was added 5-bromothiophene-2-carboxylic acid (14.86 g, 71.7 mmol), Na₂CO₃ (24.27 g in 250 mL H₂O, 229.0 mmol) 4-trifluoromethylphenyl boronic acid (15.0 g, 79.0 mmol), H₂O (250 mL) and Pd(OAc)₂ (185.0 mg, 0.8 mmol). The flask was equipped with a reflux condenser and the mixture was heated at 80° C. for 17 h under a balloon atmosphere of nitrogen. The solution was cooled, acidified to pH 2 and the solid filtered. The crude solid was dried overnight (high vacuum) and triturated with ethanol to give 15.2 g (78%) of pure 20-1. ¹H-NMR (300 MHz, DMSO-d₆) δ 7.95 ppm (d, 2H), 7.79 ppm (d, 2H), 7.72 ppm (dd, 2H).

Example 21

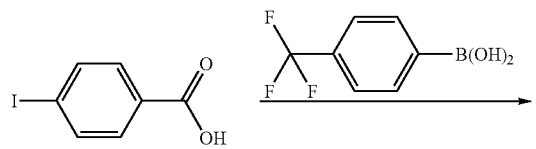

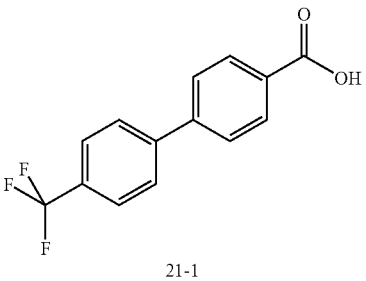

21-1

Step 21A:

To a suspension of 4-iodobenzoic acid (7.52 g, 31.9 mmol) and 4-trifluoromethylphenyl boronic acid (6.05 g, 30.0 mmol) in water (250 mL) was added Na₂CO₃ (9.65 g, 91 mmol). After stirring for 5 minutes, Pd(OAc)₂ (67.0 mg, 0.3 mmol) was added. The reaction was stirred at room temperature for 5 hours. The reaction was acidified to pH 2 and extracted with diethyl ether (3×150 mL). The combined organic layers were dried over magnesium sulfate, filtered over Celite, and concentrated. The crude product was washed with methanol (3×30 mL) to give 21-1 as a slightly purple solid. ¹H-NMR (300 MHz, DMSO-d6) δ 8.04 (d, J=8.1 Hz, 2 H), 7.95 (d, J=8.1 Hz, 2 H), 7.86 (d, J=6.3 Hz, 2H), 7.84 (d, J=6.3 Hz, 2H).

Example 22

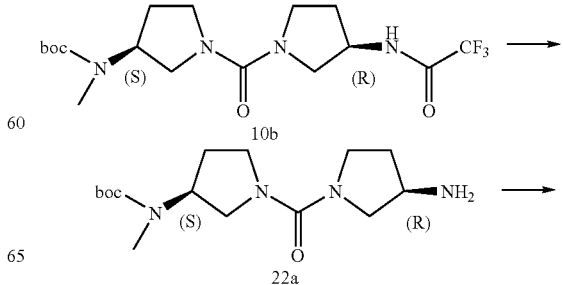

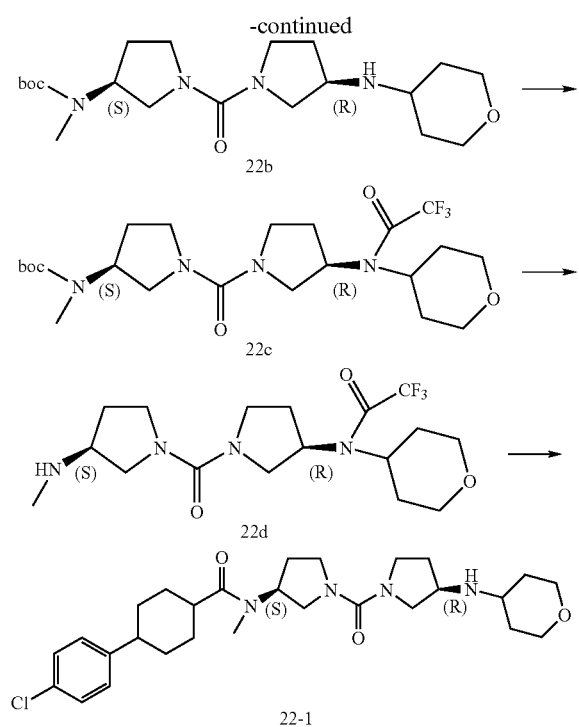

Step 22A:

Compound 10b (4.57 g, 11.2 mmol) was dissolved in a mixture of methanol (150 mL) and water (9 mL). Potassium carbonate (7.94 g, 58.0 mmol) was added and the resulting mixture was heated at 70° C. for 4 h. The mixture was cooled, filtered and the filter cake was washed with copious amounts of dichloromethane. Following concentration, the resulting solid was suspended in dichloromethane, dried over magnesium sulfate, and filtered, again washing with copious amounts of dichloromethane. Evaporation of the filtrate gave 22a as a pale yellow powder (2.93 g, 84%). APCI MS m/z: 313.0 (MH+).

Step 22B:

To a mixture of compound 22a (900 mg, 2.88 mmol) and tetrahydropyran-4-one (290 mg, 2.88 mmol) in dichloromethane (10 mL) was added sodium triacetoxyborohydride (850 mg, 4.00 mmol). The mixture was stirred for 3 h, then diluted with dichloromethane (100 mL) and washed with saturated aqueous sodium bicarbonate (50 mL). The aqueous layer was extracted with dichloromethane (2×100 mL). The combined organics were dried over magnesium sulfate and evaporated to give 22b as a yellow oil (1.15 g, 100%). APCI MS m/z: 397.0 (MH+).

Step 22C:

To a solution of crude 22b (1.15 g, 2.88 mmol) and pyridine (0.35 mL, 4.3 mmol) in dichloromethane (15 mL) at −40° C. was added dropwise, trifluoroacetic anhydride (0.44 mL, 3.1 mmol). The mixture was warmed slowly to ambient temperature overnight, then purified directly by flash column chromatography (50% ethyl acetate/dichloromethane then 4% methanol/dichloromethane) to provide 22c as a white foam (1.22 g, 86%). APCI MS m/z: 493.0 (MH+).

Step 22D:

To a solution of 22c (1.22 g, 2.48 mmol) in dichloromethane (7 mL) was added trifluoroacetic acid (5 mL). The mixture was stirred 1 h, then evaporated, quenched with triethylamine, and dissolved in dichloromethane (50 mL). The solution was washed with saturated aqueous sodium bicarbonate (25 mL), and the aqueous layer was extracted with dichloromethane (2×50 mL). The combined organics were washed with brine (50 mL), dried over magnesium sulfate and evaporated to give 22d as a pale yellow solid (0.928 g, 95%). APCI MS m/z: 393.0 (MH+).

Step 22E:

To 4-(4-chlorophenyl)cyclohexanecarboxylic acid (0.018 g, 0.074 mmol) was added 22d (0.029 g, 0.074 mmol) in DMF (0.2 mL), and HOBt (0.010 g, 0.074 mmol) in DMF (0.1 mL). The resulting mixture was stirred 10 min, then EDCl (0.014 g, 0.074 mmol) in DMF (0.2 mL) was added and stirring was continued overnight. The mixture was evaporated, dissolved in methanol (1 mL), then water (3 drops) and potassium carbonate (0.050 g, 0.36 mmol) were added. The resulting mixture was heated at 70° C. overnight, then purified directly by preparative LC-MS to give Example 22-1 as a yellow oil (0.011 g, 25%). $^{1}$H-NMR (300 MHz, CDCl$_3$) δ 7.27 (d, J=15 Hz, 2H), 7.17 (d, J=15 Hz, 2H), 4.05–4.11 (m, 2H), 3.85–3.95 (m, 2H), 3.70–3.85 (m, 4H), 3.50–3.70 (m, 4H), 3.20–3.50 (m, 8H), 3.01 (s, 3H), 2.50–2.65 (m, 2H), 2.25–2.35 (m, 2H), 1.15–2.20 (m, 8H), 0.90–1.15 (m, 2H); APCI MS m/z: 517.3 (MH+).

Using the appropriate starting materials, the following compounds were prepared according to the procedures described above.

| Ex. | R$_4$ | NR$_1$R$_2$ | MW | MH+ | Rt | HPLC |
|---|---|---|---|---|---|---|
| 22-1 | Cl-C$_6$H$_4$-cyclohexyl- | tetrahydropyran-4-yl-NH- | 517.11 | 517.3 | 5.4 | D |

-continued
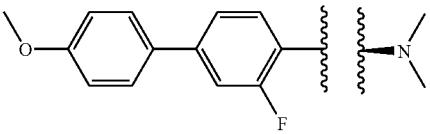
| Ex. | R4 | NR1R2 | MW | MH+ | Rt | HPLC |
|---|---|---|---|---|---|---|
| 22-2 | 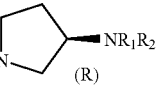 | 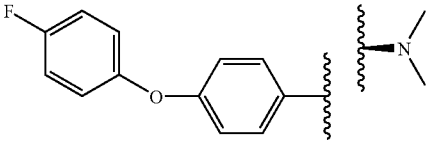 | 468.57 | 469.2 | 4.4 | D |
| 22-3 |  | 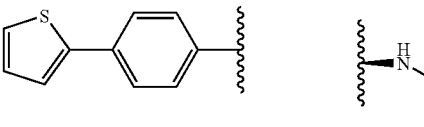 | 454.54 | 455.2 | 4.4 | D |
| 22-5 | 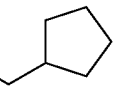 | 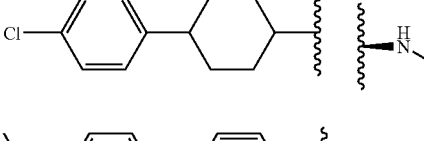 | 508.73 | 509.3 | 5.8 | D |
| 22-6 | 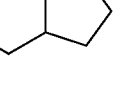 | 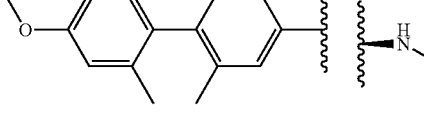 | 543.19 | 543.3 | 6.7 | D |
| 22-7 | 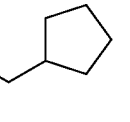 | 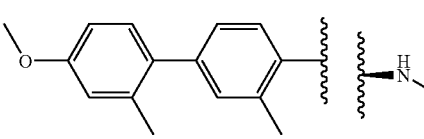 | 560.78 | 561.4 | 6.3 | D |
| 22-8 | 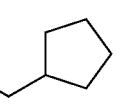 | 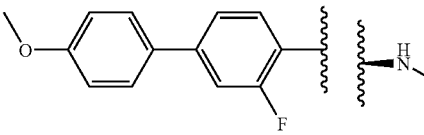 | 564.74 | 565.3 | 6.2 | D |
| 22-9 | 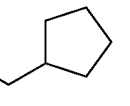 | 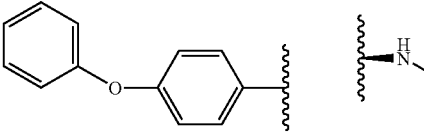 | 550.71 | 551.3 | 6.0 | D |
| 22-10 | 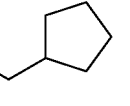 | 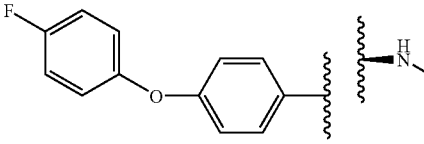 | 518.70 | 519.3 | 5.9 | D |
| 22-11 | 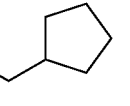 | | 536.69 | 537.3 | 6.0 | D |

-continued

| Ex. | R₄ | NR₁R₂ | MW | MH⁺ | Rt | HPLC |
|---|---|---|---|---|---|---|
| 22-12 | 6-methoxypyridin-3-yl-phenyl | tetrahydropyran-4-ylamino | 507.63 | 508.3 | 3.7 | D |
| 22-13 | 4-methoxy-2,3'-dimethylbiphenyl | tetrahydropyran-4-ylamino | 538.66 | 539.3 | 4.8 | D |
| 22-14 | 4'-methoxy-3-fluorobiphenyl | tetrahydropyran-4-ylamino | 524.63 | 525.3 | 4.6 | D |
| 22-15 | 4-(4-fluorophenoxy)phenyl | tetrahydropyran-4-ylamino | 510.61 | 511.3 | 4.6 | D |
| 22-16 | 3-(4-chlorophenyl)isoxazol-5-yl | NH₂ | 445.95 | 446.0 | — | D |

Example 23

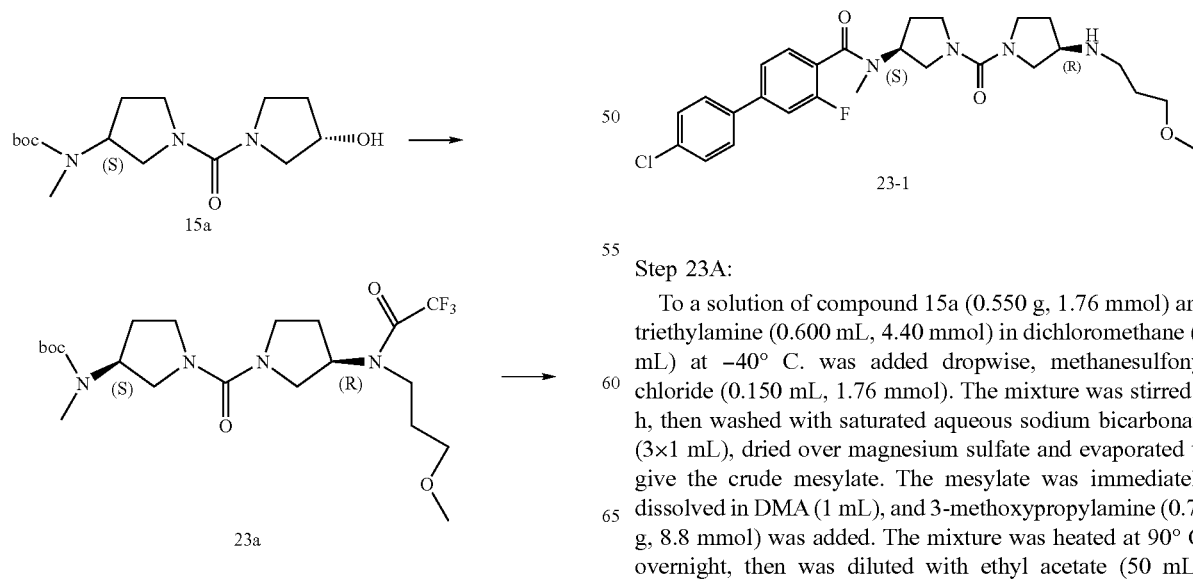

Step 23A:

To a solution of compound 15a (0.550 g, 1.76 mmol) and triethylamine (0.600 mL, 4.40 mmol) in dichloromethane (6 mL) at −40° C. was added dropwise, methanesulfonyl chloride (0.150 mL, 1.76 mmol). The mixture was stirred 2 h, then washed with saturated aqueous sodium bicarbonate (3×1 mL), dried over magnesium sulfate and evaporated to give the crude mesylate. The mesylate was immediately dissolved in DMA (1 mL), and 3-methoxypropylamine (0.77 g, 8.8 mmol) was added. The mixture was heated at 90° C. overnight, then was diluted with ethyl acetate (50 mL), washed with water (2×15 mL) and brine (15 mL), dried, and evaporated to give the crude amine. To a solution of the crude amine and pyridine (0.35 mL, 4.4 mmol) in dichloromethane (10 mL) at 0° C. was added, dropwise, trifluoroacetic anhydride (0.25 mL, 1.76 mmol). The mixture was stirred 2 h then purified directly by flash column chromatography (30% acetone/hexane) to provide 23a as a white foam (0.52 g, 62%). APCI MS m/z: 481.0 (MH$^+$).

Step 23B:

To a solution of 23a (0.50 g, 0.10 mmol) in dichloromethane (1 mL) was added trifluoroacetic acid (0.5 mL). The mixture was stirred 30 min, then evaporated, quenched with diisopropylethylamine (0.3 mL) in dichloromethane (0.5 mL), evaporated again, and dissolved in DMF (0.3 mL). A mixture of 4'-chloro-3-fluorobiphenyl-4-carboxylic acid (0.026 g, 0.10 mmol), HBTU (0.040 g, 0.10 mmol) and diisopropylethylamine (0.040 mL, 0.23 mmol) in DMF (0.5 mL) was stirred for 30 min, and the DMF solution containing the free base was added. The mixture was stirred overnight. The mixture was evaporated, dissolved in methanol (1 mL), then water (0.1 mL) and potassium carbonate (0.10 g, 0.72 mmol) were added. The resulting mixture was heated at 70° C. overnight, then purified directly by preparative LC-MS to give Example 23-1 as a yellow oil (0.039 g, 59%). APCI MS m/z: 517.1 (MH$^+$).

Using the appropriate starting materials, the following compounds were prepared according to the procedures described above.

| Ex. | R$_4$ | NR$_1$R$_2$ | MW | MH$^+$ | Rt | HPLC |
|---|---|---|---|---|---|---|
| 23-1 | 4'-Cl, 3-F biphenyl | NH-CH$_2$CH$_2$CH$_2$-OCH$_3$ | 517.04 | 517.1 | 5.9 | F |
| 23-2 | 4'-OMe, 3-F biphenyl | NH-CH$_2$CH$_2$CH$_2$-OCH$_3$ | 512.62 | 513.2 | 5.3 | F |
| 23-3 | 4'-Me, 3-F biphenyl | NH-CH$_2$CH$_2$CH$_2$-OCH$_3$ | 496.62 | 497.1 | 5.7 | F |
| 23-4 | 4'-Me, 3',3-diF biphenyl | NH-CH$_2$CH$_2$CH$_2$-OCH$_3$ | 514.61 | 515.2 | 5.9 | F |
| 23-5 | 4'-OCF$_3$, 3-F biphenyl | NH-CH$_2$CH$_2$CH$_2$-OCH$_3$ | 566.59 | 567.2 | 6.3 | F |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure:

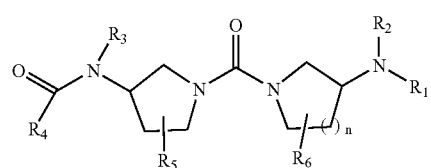

or a stereoisomer, prodrug or pharmaceutically acceptable salt thereof, wherein:
n is 0 or 1;
R$_1$ is hydrogen, alkyl, substituted alkyl, arylalkyl, substituted arylalkyl, heterocyclealkyl, substituted heterocyclealkyl, heterocycle, or substituted heterocycle;
R$_2$ is hydrogen, alkyl, substituted alkyl, —C(O)R$_7$, or —S(O)$_2$R$_8$; or
R$_1$ and R$_2$ together with the nitrogen to which they are attached form a heterocycle, optionally substituted with one or more R$_9$;
R$_3$ is hydrogen, alkyl, or substituted alkyl;
R$_4$ is alkyl, substituted alkyl, aryl, substituted aryl, heteroaryl, substituted heteroaryl, heterocycle, or substituted heterocycle;
R$_5$ is hydrogen, alkyl, or substituted alkyl;
R$_6$ is hydrogen, alkyl, or substituted alkyl;
R$_7$ is hydrogen, alkyl, substituted alkyl, hydroxy, alkoxy, aryl, substituted aryl, heterocycle, or substituted heterocycle;
R$_8$ is hydrogen, alkyl, substituted alkyl; and
R$_9$ is alkyl, substituted alkyl, aryl, substituted aryl, hydroxy, or alkoxy.

2. The compound of claim 1 wherein n is 0.
3. The compound of claim 1 wherein n is 1.
4. The compound of claim 1 wherein R$_1$ is hydrogen, alkyl, substituted alkyl, arylalkyl, substituted arylalkyl, heterocyclealkyl, substituted heterocyclealkyl, heterocycle or substituted heterocycle.
5. The compound of claim 1 wherein R$_4$ is substituted alkyl, substituted aryl, substituted heteroaryl, or substituted heterocycle.
6. The compound of claim 2 wherein R$_1$ is hydrogen, alkyl, substituted alkyl, arylalkyl, substituted arylalkyl, heterocyclealkyl, substituted heterocyclealkyl, heterocycle or substituted heterocycle.
7. The compound of claim 2 wherein R$_4$ is substituted alkyl, substituted aryl, substituted heteroaryl, or substituted heterocycle.
8. The compound of claim 3 wherein R$_1$ is hydrogen, alkyl, substituted alkyl, arylalkyl, substituted arylalkyl, heterocyclealkyl, substituted heterocyclealkyl, heterocycle or substituted heterocycle.
9. The compound of claim 8 wherein R$_2$ is hydrogen, alkyl or substituted alkyl.
10. The compound of claim 3 wherein R$_1$ and R$_2$ together with the nitrogen to which they are attached form a heterocycle, optionally substituted with one or more substituent selected from the group consisting of alkyl, substituted alkyl, aryl, substituted aryl, hydroxy and alkoxy.
11. The compound of claim 3 wherein R$_4$ is substituted alkyl, substituted aryl, substituted heteroaryl, or substituted heterocycle.
12. The compound of claim 9 wherein R$_4$ is substituted alkyl, substituted aryl, substituted heteroaryl, or substituted heterocycle.
13. The compound of claim 12 wherein R$_3$, R$_5$ and R$_6$ are the same or different and independently hydrogen, alkyl or substituted alkyl.
14. The compound of claim 13 wherein R$_5$ and R$_6$ are each hydrogen.
15. The compound of claim 14 wherein R$_3$ is lower alkyl.
16. The compound of claim 15 wherein R$_3$ is methyl.
17. The compound of claim 15 wherein R$_4$ is substituted heteroaryl.
18. The compound of claim 17 wherein R$_4$ is substituted thienyl.

19. The compound of claim 18 wherein R$_4$ is 2-[5-(4-ethylphenyl)thienyl], 2-[5-(4-trifluoromethylphenyl)thienyl], 2-[5-(4-trifluoromethoxyphenyl)thienyl], 2-[5-(2-methyl-4-methoxyphenyl)thienyl], 2-[5-(2-trifluoromethyl-4-chlorophenyl)thienyl], 2-[5-(4-methylphenyl)thienyl], 2-(5-phenylthienyl), 2-[5-(4-methoxyphenyl)thienyl], 2-[5-(3-fluoro-4-methoxyphenyl)thienyl], 2-[5-(6-1,4-benzodioxanyl)thienyl], 2-[5-(4-ethoxyphenyl)thienyl], 2-[5-(3-fluoro-4-methylphenyl)thienyl], 2-[5-(2,4-dimethylphenyl)thienyl] or 2-[5-(4-isopropylphenyl)thienyl].
20. The compound of any of the claims 17–19 wherein R$_2$ is hydrogen, alkyl or substituted alkyl.
21. The compound of claim 20 wherein R$_2$ is hydrogen, methyl and ethyl.
22. The compound of claim 21 wherein R$_1$ is hydrogen.
23. The compound of claim 20 wherein R$_1$ is cyclic alkyl or substituted cyclic alkyl.
24. The compound of claim 23 wherein R$_1$ is cyclobutyl, cyclopentyl, cyclohexyl, 4-methylcyclohexyl, 4,4-dimethylcyclohexyl, 4-trifluoromethylcyclohexyl, 2-ethylcyclohexyl, 3,4-dimethylcyclohexyl or cycloheptyl.
25. The compound of claim 21 wherein R$_1$ is heterocycle or substituted heterocycle.
26. The compound of claim 25 wherein R$_1$ is 4-tetrahydropyranyl or 4-(1-benzylpiperidinyl).
27. The compound of claim 20 wherein R$_1$ is heterocyclealkyl or substituted heterocyclealkyl.
28. The compound of claim 27 wherein R$_1$ is 4-tetrahydropyranylmethyl, 2-tetrahydrofuranylmethyl, 2-(3-tetrahydrofuranyl)ethyl, 2-(4-tetrahydropyranyl)ethyl, 2-(2-1,3-dioxolanyl)ethyl, 2-(2-1,3-dioxanyl)ethyl or 3-tetrahydrofuranylmethyl.
29. The compound of claim 20 wherein R$_1$ is alkyl or substituted alkyl.
30. The compound of claim 29 wherein R$_1$ is methyl, ethyl, isopropyl, 3-methylbutyl, 2-butyl, 3-butyl, cyclopropylmethyl, 1-(1-cyclobutyl)ethyl, 2-(1-cyclohexyl)propyl, 2-(3-methyl)butyl, 1-(2-methyl)propyl, 3-cyclopentylpropyl or 3-cyclohexylpropryl.
31. The compound of claim 29 wherein R$_1$ is alkyl substituted by alkoxy, aryl, alkylsulfonyl, alkylamino, hydroxy or arylsulfonyl.
32. The compound of claim 31 wherein R$_1$ is 3-methoxypropyl, 2-methoxyethyl, 2-methylsulfonylethyl, 2-(1-methoxyethyl), 2-isopropoxyethyl, benzyl or 1-[1-(4-methoxypheny)ethyl].
33. The compound of any of the claims 17–19 wherein R$_1$ and R$_2$ together with the nitrogen to which they are attached form a heterocycle, optionally substituted by alkyl or aryl.
34. The compound of claim 33 wherein R$_1$ and R$_2$ together with the nitrogen to which they are attached form piperidinyl, pyrrolidinyl, homopiperidinyl, 4-phenylpiperidinyl, 4-propylpiperidinyl, 4-methylpiperidinyl, 2,6-dimethylmorpholinyl, 3-hydroxypyrrolidinyl and 4-hydroxypiperidinyl.
35. The compound of claim 15 wherein R$_4$ is substituted phenyl.
36. The compound of claim 35 wherein R$_4$ is phenyl substituted with aryl or substituted aryl.
37. The compound of claim 36 wherein R$_4$ is 4-phenylphenyl, 4-(2-methyl-4-methoxyphenyl)phenyl, 4-(4-ethylphenyl)phenyl, 4-(4-methylphenyl)phenyl, 2-fluoro-4-(4-methoxyphenyl)phenyl, 2-fluoro-4-(4-methylphenyl)phenyl, 2-fluoro-4-(2-fluoro-4-methylphenyl)phenyl, 2-fluoro-4-(4-chlorophenyl)phenyl, (4-methoxyphenyl)phenyl or 2-fluoro-4-(4-trifluoromethoxyphenyl)phenyl.

38. The compound of any of the claims 35–37 wherein $R_2$ is hydrogen, alkyl or substituted alkyl.

39. The compound of any of the claims 35–37 wherein $R_2$ is hydrogen, methyl or ethyl.

40. The compound of claim 39 wherein $R_1$ is hydrogen.

41. The compound of claim 39 wherein $R_1$ is cyclic alkyl or substituted cyclic alkyl.

42. The compound of claim 41 wherein $R_1$ is cyclobutyl, cyclopentyl, cyclohexyl, 4,4-dimethylcyclohexyl or cycloheptyl.

43. The compound of claim 39 wherein $R_1$ is heterocycle or substituted heterocycle.

44. The compound of claim 43 wherein $R_1$ is 4-tetrahydropyranyl or 4-(1-benzylpiperidinyl).

45. The compound of claim 39 wherein $R_1$ is heterocyclealkyl or substituted heterocyclealkyl.

46. The compound of claim 45 wherein $R_1$ is 4-tetrahydropyranylmethyl, 2-(3-tetrahydrofuranyl)ethyl, 2-(4-tetrahydropyranyl)ethyl, 2-(2-1,3-dioxolanyl)ethyl, 2-(2-1,3-dioxanyl)ethyl, 2-tetrahydrofuranylmethyl or 3-tetrahydrofuranylmethyl.

47. The compound of claim 39 wherein $R_1$ is alkyl or substituted alkyl.

48. The compound of claim 47 wherein $R_1$ is methyl, ethyl, isopropyl, 3-methylbutyl, 2-butyl, 3-butyl, cyclopropylmethyl, 1-(1-cyclobutyl)ethyl, 2-(1-cyclohexyl)propyl, 2-(3-methyl)butyl, 1-(2-methyl)propyl, 3-cyclopentylpropyl or 3-cyclohexylpropyl.

49. The compound of claim 47 wherein $R_1$ is alkyl substituted alkoxy, alkylsulfonyl, alkylamino or hydroxy.

50. The compound of claim 49 wherein $R_1$ is 3-methoxypropyl, 2-methoxyethyl, 1-(1-methoxyethyl), 2-isopropoxyethyl or 2-N,N-dimethylaminoethyl.

51. The compound of any of claims 35–37 wherein $R_1$ and $R_2$ together with the nitrogen to which they are attached form a heterocycle, optionally substituted by alkyl or aryl.

52. The compound of claim 51 wherein $R_1$ and $R_2$ together with the nitrogen to which they are attached form piperidinyl, homopiperidinyl or 4-phenylpiperidinyl.

53. The compound of claim 15 wherein $R_4$ is substituted cyclohexyl.

54. The compound of claim 53 wherein $R_4$ is cyclohexyl substituted by aryl or substituted aryl.

55. The compound of claim 54 wherein $R_4$ is 4-chlorophenylcyclohexyl.

56. The compound of any of the claims 53–55 wherein $R_1$ and $R_2$ are the same or different and independently hydrogen or methyl.

57. A composition comprising a compound of claim 1 in combination with a pharmaceutically acceptable carrier or diluent.

58. A method for treating obesity in a subject in need thereof, comprising administering to the subject an effective amount of a compound of claim 1 or a composition of claim 57.

59. A method for treating anxiety and/or depression in a subject in need thereof, comprising administering to the subject an effective amount of a compound of claim 1 or a composition of claim 57.

* * * * *